US008007814B2

(12) United States Patent
Ginns et al.

(10) Patent No.: US 8,007,814 B2
(45) Date of Patent: *Aug. 30, 2011

(54) THERAPY FOR LYSOSOMAL ENZYME DEFICIENCIES

(75) Inventors: Edward I. Ginns, Shrewsbury, MA (US); Gary R. Ostroff, Worcester, MA (US)

(73) Assignee: University of Massachusetts, Boston, MA (US)

( * ) Notice: Subject to any disclaimer, the term of this patent is extended or adjusted under 35 U.S.C. 154(b) by 402 days.

This patent is subject to a terminal disclaimer.

(21) Appl. No.: 11/230,017

(22) Filed: Sep. 19, 2005

(65) Prior Publication Data

US 2006/0083718 A1   Apr. 20, 2006

Related U.S. Application Data

(63) Continuation-in-part of application No. 10/869,693, filed on Jun. 16, 2004, now Pat. No. 7,740,861.

(60) Provisional application No. 60/610,872, filed on Sep. 17, 2004.

(51) Int. Cl.
*A61K 36/06* (2006.01)
*A61K 9/00* (2006.01)
(52) U.S. Cl. .................... 424/195.16; 424/400
(58) Field of Classification Search ............... None
See application file for complete search history.

(56) References Cited

U.S. PATENT DOCUMENTS

| | | | |
|---|---|---|---|
| 3,737,337 A | 6/1973 | Schnoring et al. ........... 117/100 |
| 3,891,570 A | 6/1975 | Fukushima et al. .......... 252/316 |
| 4,160,452 A | 7/1979 | Theeuwes ..................... 128/260 |
| 4,256,108 A | 3/1981 | Theeuwes ..................... 128/260 |
| 4,265,874 A | 5/1981 | Bonsen et al. ................... 424/15 |
| 4,384,975 A | 5/1983 | Fong ........................ 427/213.36 |
| 4,389,330 A | 6/1983 | Tice et al. ................ 427/213.36 |
| 4,652,441 A | 3/1987 | Okada et al. ..................... 424/19 |
| 4,663,308 A | 5/1987 | Saffran et al. ..................... 514/3 |
| 4,777,049 A | 10/1988 | Magruder et al. ............ 424/457 |
| 4,810,646 A | 3/1989 | Jamas et al. .................. 435/101 |
| 4,946,778 A | 8/1990 | Ladner et al. ................ 435/69.6 |
| 4,956,778 A | 9/1990 | Naito ...................... 364/426.04 |
| 4,992,540 A | 2/1991 | Jamas et al. .................. 536/123 |
| 5,028,703 A | 7/1991 | Jamas et al. .................. 536/114 |
| 5,032,401 A | 7/1991 | Jamas et al. |
| 5,082,936 A | 1/1992 | Jamas et al. .................. 536/123 |
| 5,091,513 A | 2/1992 | Huston et al. ................. 530/387 |
| 5,132,405 A | 7/1992 | Huston et al. .............. 530/387.3 |
| 5,322,841 A | 6/1994 | Jamas et al. ..................... 514/54 |
| 5,401,727 A | 3/1995 | Rorstad et al. ................... 514/54 |
| 5,407,609 A | 4/1995 | Tice et al. ........................ 264/46 |
| 5,488,040 A | 1/1996 | Jamas et al. |
| 5,504,079 A | 4/1996 | Jamas et al. ..................... 514/54 |
| 5,532,223 A | 7/1996 | Jamas et al. |
| 5,545,806 A | 8/1996 | Lonberg et al. .................. 800/2 |
| 5,569,825 A | 10/1996 | Lonberg et al. .................. 800/2 |
| 5,607,677 A | 3/1997 | Jamas et al. |
| 5,622,939 A | 4/1997 | Jamas et al. |
| 5,622,940 A | 4/1997 | Ostroff |
| 5,633,369 A | 5/1997 | Jamas et al. |
| 5,663,324 A | 9/1997 | James et al. |
| 5,705,153 A | 1/1998 | Shorr et al. ................. 424/94.61 |
| 5,741,495 A * | 4/1998 | Jamas et al. ................ 424/278.1 |
| 5,783,569 A | 7/1998 | Jamas et al. |
| 5,811,542 A | 9/1998 | Jamas et al. |
| 5,814,318 A | 9/1998 | Lonberg et al. ............ 424/184.1 |
| 5,817,643 A | 10/1998 | Jamas et al. |
| 5,849,720 A | 12/1998 | Jamas et al. |
| 5,879,680 A | 3/1999 | Ginns et al. ................ 424/185.1 |
| 5,911,983 A | 6/1999 | Barranger et al. .......... 424/93.21 |
| 5,968,811 A | 10/1999 | Greenshields ............. 435/255.2 |
| 6,074,864 A | 6/2000 | Ginns et al. ................... 435/209 |
| 6,118,045 A | 9/2000 | Reuser et al. ................... 800/14 |
| 6,133,229 A | 10/2000 | Gibson et al. |
| 6,369,216 B1 | 4/2002 | Patchen et al. |
| 6,372,499 B1 | 4/2002 | Midoux et al. ............... 435/455 |
| 6,379,965 B1 | 4/2002 | Boutin ......................... 435/455 |
| 6,420,176 B1 * | 7/2002 | Lisziewicz et al. .......... 435/455 |
| 6,444,448 B1 | 9/2002 | Wheatcroft et al. .......... 435/101 |
| 6,476,003 B1 | 11/2002 | Jordan et al. .................... 514/54 |
| 6,495,570 B2 | 12/2002 | Jacob et al. ..................... 514/328 |
| 6,512,097 B1 | 1/2003 | Marks et al. ............... 530/391.1 |

(Continued)

FOREIGN PATENT DOCUMENTS

EP        0242135 A2    10/1987

(Continued)

OTHER PUBLICATIONS

Fabrega, S., et al., "Human Glucocerebrosidase: Heterologous Expression of Active Site Mutants in Murine Null Cells", *Glycobiology*, Vo. 10, No. 11, pp. 1217-1224, 2000.
pIRES-EGFP, Vector Information, GenBank Accession #: Submission in Progress, PT3157-5, Clontech Laboratories, Inc., 1997.
Hiraiwa, M., et al., "Isolation, Characterization, and Proteolysis of Human Prosaposin, the Precursor of Saposins (Sphingolipid Activator Proteins)", *Archives of Biochemistry and Biophysics*, vol. 304, No. 1, July, pp. 110-116, 1993.
NIH Guide: CNS Therapy Development for Lysosomal Storage Disorders, Department of Health and Human Services, Release Date: Jul. 2, 2004, PA No. PAS-04-120.
Aviner, S., et al., Case Report "Anaphylactoid Reaction to Imiglucerase, but Not to Alglucerase, in a Type I Gaucher Patient", *Blood Cells, Molecules, and Diseases* (1999), 25(5), Mar. 15: pp. 92-94.
Orvisky, E., et al., "Glucosylsphingosine Accumulation in Tissues from Patients with Gaucher Disease: Correlation with Phenotype and Genotype", *Molecular Genetics and Metabolism* 76 (2002), pp. 262-270.

(Continued)

*Primary Examiner* — Christopher R Tate
*Assistant Examiner* — Randall Winston
(74) *Attorney, Agent, or Firm* — Nelson Mullins Riley & Scarborough LLP; Debra J. Milasincic, Esq.

(57) ABSTRACT

The present invention provides a therapeutic delivery system comprising an extracted yeast cell wall comprising beta-glucan, a payload trapping molecule and a payload molecule, wherein the payload molecule and the payload trapping molecule are soluble in the same solvent system wherein the payload molecule supplements the function of the deficient lysosomal enzyme. The invention further provides methods of making and methods of using the therapeutic delivery system.

31 Claims, 19 Drawing Sheets

U.S. PATENT DOCUMENTS

| | | | |
|---|---|---|---|
| 6,696,272 | B1 | 2/2004 | Mahuran et al. ............. 435/69.1 |
| 7,022,685 | B2 | 4/2006 | Patchen et al. |
| 7,220,427 | B2 * | 5/2007 | Jordan ......................... 424/443 |
| 7,229,623 | B1 | 6/2007 | Cheever et al. |
| 2002/0032170 | A1 | 3/2002 | Jamas et al. |
| 2002/0143174 | A1 | 10/2002 | Patchen et al. |
| 2003/0216346 | A1 | 11/2003 | Sakurai et al. .................. 514/44 |
| 2004/0014715 | A1 | 1/2004 | Ostroff ............................ 514/54 |
| 2004/0116380 | A1 | 6/2004 | Jamas et al. |
| 2005/0245480 | A1 | 11/2005 | Ostroff et al. |
| 2005/0281781 | A1 | 12/2005 | Ostroff |
| 2006/0165700 | A1 | 7/2006 | Ostroff et al. |
| 2006/0247205 | A1 | 11/2006 | Patchen et al. |
| 2008/0044438 | A1 | 2/2008 | Ostroff et al. |
| 2008/0220038 | A1 | 9/2008 | Franklin et al. |

FOREIGN PATENT DOCUMENTS

| | | | |
|---|---|---|---|
| WO | WO 89/05850 A1 | 6/1989 | |
| WO | 90/15596 A1 | 12/1990 | |
| WO | 91/03248 A2 | 3/1991 | |
| WO | 91/03495 A1 | 3/1991 | |
| WO | 92/07064 A1 | 4/1992 | |
| WO | 94/04163 A1 | 3/1994 | |
| WO | 00/18411 A1 | 4/2000 | |
| WO | WO 02/12348 A2 | 2/2002 | |
| WO | 2004/014320 A2 | 2/2004 | |
| WO | WO 2004/012657 A2 | 2/2004 | |
| WO | WO 2004/021994 A2 | 3/2004 | |
| WO | 2004/037232 A1 | 5/2004 | |
| WO | 2005/014776 A2 | 2/2005 | |
| WO | WO 2006/007372 A2 | 1/2006 | |
| WO | 2006/032039 A2 | 3/2006 | |
| WO | 2007/050643 A2 | 5/2007 | |
| WO | 2007/109564 A2 | 9/2007 | |
| WO | 2009/058913 A2 | 5/2009 | |

OTHER PUBLICATIONS

Erickson, A., et al., "Biosynthesis of the Lysosomal Enzyme Glucocerebrosidase", *The Journal of Biological Chemistry*, vol. 260, No. 26, Nov. 15, pp. 14319-14324.

Bonten, E. J., et al., "Targeting Macrophages with Baculovirus-Produced Lysosomal Enzymes: Implications for Enzyme Replacement Therapy of the Glycoprotein Storage Disorder Galactosialidosis", *The FASEB Journal*, Express Article 10.1096/fj. 03-0941 fje., Published online Apr. 14, 2004.

Reichner, J. S., et al., "Receptor-Mediated Phagocytosis of Rat Macrophages is Regulated Differentially for Opsonized Particles and Non-Opsonized Particles Containing β-glucan", *Immunology*, 2001, 104, pp. 198-206.

Wilcox, W. R., MD, PhD, "Lysosomal Storage Disorders: The Need for Better Pediatric Recognition and Comprehensive Care", *The Journal of Pediatrics*, May 2004, pp. S3-S14.

Wilson, H.M., et al., "Targeting Genetically Modified Macrophages to the Glomerulus", *Nephron Experimental Nephrology, Minireview*, 2003, 94:e 113-e 118.

Eto, Y., et al., "Treatment of Lysosomal Storage Disorders: Cell Therapy and Gene Therapy", *J. Inherit. Metab. Dis.* 27 (2004), pp. 411-415.

Ribeiro, C.C., et al., "Calcium Phosphate-Alginate Microspheres as Enzyme Delivery Matrices", *Biomaterials* 25 (2004), pp. 4363-4373.

Germain, D. P., et al., "Fabry Disease: Recent Advances in Enzyme Replacement Therapy", *Expert Opinion, Investig. Drugs* (2002), pp. 1467-1476.

Cho, M. E., et al., "Fabry Disease in the Era of Enzyme Replacement Therapy: a Renal Perspective", *Pediatr Nephrol* (2004) 19:583-593.

LeBowitz, J. H., et al., "Glycosylation-Independent Targeting Enhances Delivery to Lysosomes and Decreases Storage in Mucopolysaccharidosis Type VII Mice", *PNAS*, Mar. 2, 2004, vol. 101, No. 9, pp. 3083-3088.

Sleeper, M. M., VMD et al., "Gene Therapy Ameliorates Cardiovascular Disease in Dogs with Mucopolysaccharidosis VII", *Circulation*, Aug. 17, 2004, pp. 815-820.

Burke, B., et al., "Macrophages in Gene Therapy: Cellular Delivery Vehicles and in Vivo Targets", *Journal of Leukocyte Biology*, vol. 72, Sep. 2002, pp. 417-428.

Burke, B., "Macrophages as Novel Cellular Vehicles for Gene Therapy", *Expert Opinion, Biol Ther.* (2003) 3(6), pp. 919-924.

Novelli, E. M., et al., "Gene Therapy for Lysosomal Storage Disorders", *Expert Opinion, Biol Ther.* (2001) 1(5), pp. 857-867.

Grabowski, G.A., MD, "Gaucher Disease: Lessons From a Decade of Therapy", *The Journal of Pediatrics*, May 2004, S15-S19.

Desnick, R. J., PhD, MD, et al., "Fabry Disease, an Under-Recognized Multisystemic Disorder: Expert Recommendations for Diagnosis, Management, and Enzyme Replacement Therapy", *Annuals of Internal Medicine*, vol. 138, No. 4, pp. 338-347.

Li, Y., et al., "Direct Multiplex Assay of Lysosomal Enzymes in Dried Blood Spots for Newborn Screening", *Clinical Chemistry*, 50, No. 10, 2004.

Meikle, P. J., et al., "Lysosomal Storage Disorders: Emerging Therapeutic Options Require Early Diagnosis", *Eur J Pediatr* (2003), 162: S34-S37.

D'Azzo, A., "Gene Transfer Strategies for Correction of Lysosomal Storage Disorders", *Acta Haematol* 2003; 110:71-85.

Charrow, J., MD, et al., "Enzyme Replacement Therapy and Monitoring for Children with Type 1 Gaucher Disease: Consensus Recommendations", *The Journal of Pediatrics*, Jan. 2004, pp. 112-120.

Brooks, D. A., et al., "Significance of Immune Response to Enzyme-Replacement Therapy for Patients with a Lysosomal Storage Disorder", *Trends in Molecular Medicine*, vol. 9, No. 10, Oct. 2003, pp. 450-453.

Zimmerman, J. W., et al., "A Novel Carbohydrate-Glycosphingolipid Interaction between a β-(1-3)-Glucan Immunomodulator, PGG-glucan, and Lactosylceramide of Human Leukocytes", *The Journal of Biological Chemistry*, vol. 273, No. 34, Issue of Aug. 21, pp. 22014-22020.

Shetty, K., et al., "Gene Therapy of Hepatic Diseases: Prospects for the New Millennium", *Gut* 2000; 46:136-139.

Wu, G. Y., et al., "Receptor-Mediated in Vitro Gene Transformation by a Soluble DNA Carrier System", *The Journal of Biological Chemistry*, vol. 262, No. 10, Apr. 5, pp. 4429-4432, 1987.

Curiel, D. T., et al., "Adenovirus Enhancement of Transferrin-Polylysine-Mediated Gene Delivery", *Proc. Natl. Acad. Sci. USA* 88 (1991), pp. 8850-8854.

Murphy, J. E., et al., "A Combinatorial Approach to the Discovery of Efficient Cationic Peptoid Reagents for Gene Delivery", *Proc. Natl. Acad. Sci. USA*, vol. 95, pp. 1517-1522, Feb. 1998.

Felgner, P. L., et al., "Lipofection: A Highly Efficient, Lipid-Mediated DNA-Transfection Procedure", *Proc. Natl., Acad. Sci. USA*, vol. 84, pp. 7413-7417, Nov. 1987.

Howell, M. D., et al., "Limited T-Cell Receptor β-Chain Heterogeneity Among Interleukin 2 Receptor-Positive Synovial T cells Suggests a Role for Superantigen in Rheumatoid Arthritis", *Proc. Natl. Acad. Sci. USA*, vol. 88, pp. 10921-10925, Dec. 1991.

Williams, W. V., et al., "Restricted Heterogeneity of T Cell Receptor Transcripts in Rheumatoid Synovium", *T Cell Receptors in Rheumatoid Symovium*, pp. 326-333.

Nakase, H., et al., "New Cytokine Delivery System Using Gelatin Microspheres Containing Interleukin-10 for Experimental Inflammatory Bowel Disease", *The Journal of Pharmacology and Experimental Therapeutics*, vol. 301, No. 1, pp. 59-65.

Nakase, H., et al., "Development of an Oral Drug Delivery System Targeting Immune-Regulating Cells in Experimental Inflammatory Bowel Disease: A New Therapeutic Strategy", *The Journal of Pharmacology and Experimental Therapeutics*, vol. 292, No. 1, pp. 15-21.

Bonfils, E., et al., "Drug targeting: synthesis and endocytosis of oligonucleotide-neoglycoprotein conjugates", *Nucleic Acids Research*, vol. 20, No. 17, pp. 4621-4629.

Beier, R., et al., Kinetics of particle uptake in the domes of Peyer's patches, *The American Physiological Society*, pp. G130-G137.

Fromen-Romano, C., et al., "Transformation of a non-enzymatic toxin into a toxoid by genetic engineering", *Protein Engineering*, vol. 10, No. 10, pp. 1213-1220, 1997.

Kurtzman, A. L., et al., "Advances in directed protein evolution by recursive genetic recombination: applications to therapeutic proteins", *Current Opinion in Biotechnology* 2001, 12:361-370.

Neutra, M. R., "Current Concepts in Mucosal Immunity V. Role of M cells in transepithelial transport of antigens and pathogens t the mucosal immune system", *The American Physiological Society*, G785-G791.

Dervan, P. B., "Molecular Recognition of DNA by Small Molecules", *Bioorganic & Medicinal Chemistry* 9 (2001) 2215-2235.

Chaudhary, V. K., et al., "A rapid method of cloning functional variable-region antibody genes in *Escherichia coli* as single-chain immunotoxins", *Proc. Natl. acad. Sci. USA*, vol. 87, pp. 1066-1070, Feb. 1990.

Jepson, M. A., et al., "M cell targeting by lectins: a strategy for mucosal vaccination and drug delivery", *Advanced Drug Delivery Reviews* 56 (2004) 511-525.

Clark, M. A., et al., "Exploiting M cells for drug and vaccine delivery", *Advanced Drug Delivery Reviews* 50 (2001) 81-106.

Nakase, H. et al., "Biodegradable microspheres targeting mucosal immune-regulating cells: new approach for treatment of inflammatory bowel disease", *J. Gastroenterol.* Mar. 2003; 38 Suppl 15:59-62.

van der Lubben, IM, et al., "Transport of chitosan microparticles for mucosal vaccine delivery in a human intestinal M-cell model", *J. Drug Target.*, Sep. 2002; 10(6):449-56.

Bogwald, J., et al., "Lysosomal glycosidases in mouse peritoneal macrophages stimulated in vitro with soluble and insoluble glycans", *J Leukoc Biol.* Apr. 1984;35(4):357-71.

Tsuji, S., et al., "Signal sequence and DNA-mediated expression of human lysosomal alpha-galactosidase A", *Eur J Biochem.* Jun. 1, 1987;165(2):275-80.

Martin BM, et al., "Glycosylation and processing of high levels of active human glucocerebrosidase in invertebrate cells using a baculovirus expression vector", *DNA.* Mar. 1998;7(2):99-106.

International Search Report PCT/US 2005/033300 Received Feb. 13, 2007.

Chang P L: "Microencapsulation—An alternative approach to gene therapy" Transfusion Science, vol. 17, No. 1, Mar. 1996.

First Office Action, Chinese Application for Invention No. 200580037576.4 Received Jan. 3, 2009, and English translation as provided by the Chinese foreign associate.

Champagne M.J., Lamontagne, S., Potier, M., Binding of GM1-ganglioside to a synthetic peptide derived from the lysosomal sphingolipid-activator-protein saposin B. FEBS Lett. Jun. 27, 1994;347(2-3):265-7.

Magnelli, P., Cipollo, J.F., Abeijon, C., A refined method for the determination of *Saccharomyces cerevisiae* cell wall composition and beta-1,6-glucan fine structure. 1: Anal. Biochem. Feb. 1, 2002;301(1):136-150.

Zhao, H., Liu, Z., Protein Glycoengineering, Journal of Chinese Biotechnology, 2003, 23(9): 18-20. English Abstract.

Beier, Rita et al., "Kinetics of particle uptake in the domes of Peyer's patches," Am. J. Physiol., vol. 275(1 pt. 1):G130-G137 (1998).

Bonfils, E. et al., "Drug targeting: synthesis and endocytosis of oligonucleotide-neoglycoprotein conjugates," Nucleic Acids Research, vol. 20(17):4621-4629 (1992).

Desnick, Robert J. et al., "Fabry Disease, an Under-Recognized Multisystemic Disorder: Expert Recommendations for Diagnosis, Management and Enzyme Replacement Therapy," Ann. Intern. Med., vol. 138:338-346 (2003).

Erickson, Ann H. et al., "Biosynthesis of the Lysosomal Enzyme Glucocerebrosidase," The Journal of Biological Chemistry, vol. 260(26):14319-14324 (1985).

Nakase, Hiroshi et al., "Development of an Oral Drug Delivery System Targeting Immune-Regulating Cells in Experimental Inflammatory Bowel Disease: A New Therapeutic Strategy," The Journal of Pharmacology and Experimental Therapeutics, vol. 292(1):15-21 (2000).

Nakase, Hiroshi et al., "New Cytokine Delivery System Using Gelatin Microspheres Containing Interleukin-10 for Experimental Inflammatory Bowel Disease," The Journal of Pharmacology and Experimental Therapeutics, vol. 301 (1):59-65 (2002).

Neutra, Marian R., "Current Concepts in Mucosal Immunity V. Role of M cells in transepithelial transport of antigens and pathogens to the mucosal immune system?" Am. J. Physiol., vol. 274(5 Pt. 1):G785-G791 (1998).

Williams, William V. et al., "Restricted Hetergeneity of T Cell Receptor Transcripts in Rheumatoid Synovium," J. Clin. Invest., vol. 90:326-333 (1992).

Zhao, , H. et al., "Protein Glycoengineering," Journal of Chinese Biotechnology, vol. 23(9):18-20 (2003).

Zimmerman, Janet W. et al., "A Novel Carbohydrate-Glycosphingolipid Interaction between a b-(1-3)-Glucan Immunomodulator, PGG-glucan and Lactosylceramide of Human Leukocytes," The Journal of Biological Chemistry, vol. 273(34):22014-22020 (1998).

International Search Report for Application No. PCT/US2005/021161, dated Jul. 25, 2006.

Australian Office Action for Application No. 2005284727, dated Apr. 13, 2010.

Chinese Office Action for Application No. 200580037576.4, dated Mar. 23, 2010.

\* cited by examiner

Yeast Cell Wall Particle

YGMP Beta Glucan

YGP Beta Glucan

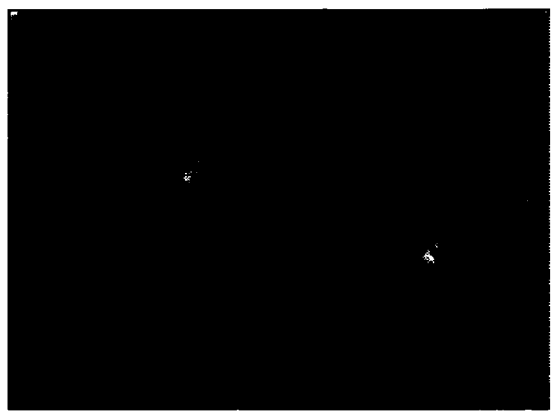
FIG. 11A
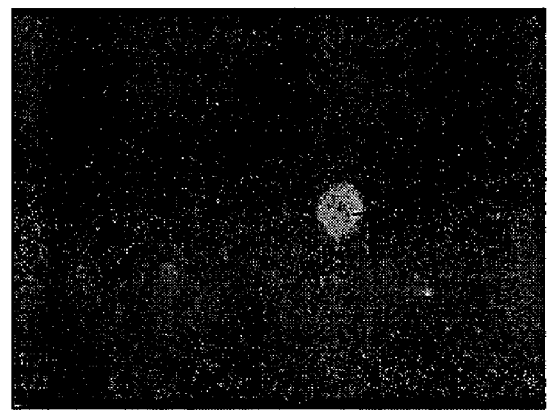
FIG. 11B — 930
FIG. 11C — 931
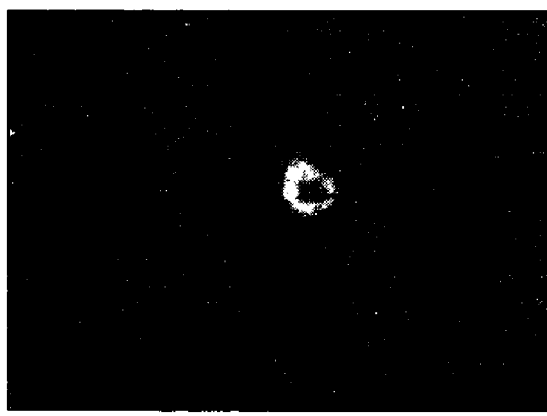
FIG. 11D — 932

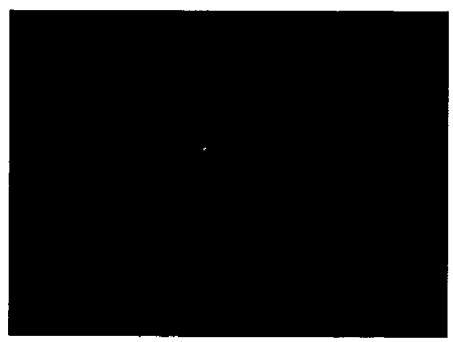
FIG. 12A
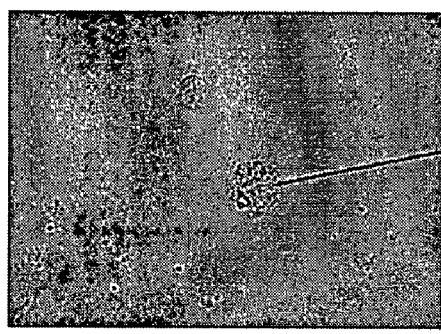
FIG. 12B — 935
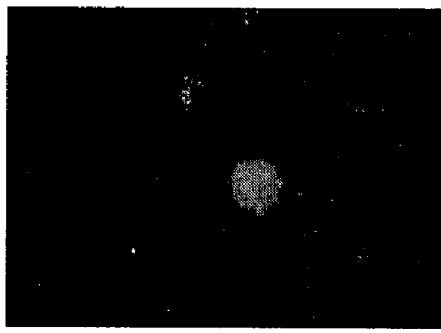
FIG. 12C — 935
FIG. 12D — 936
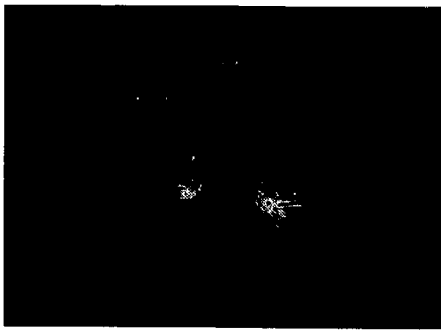
FIG. 12E — 937

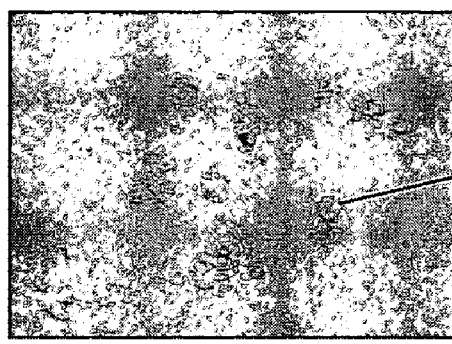
FIG. 12F — 938
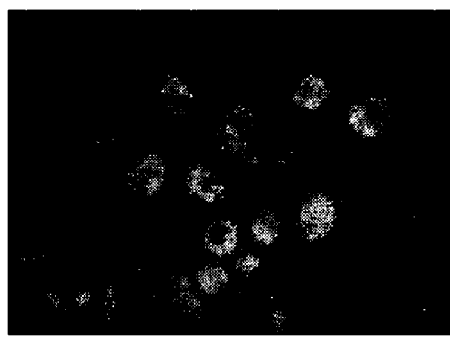
FIG. 12G — 938
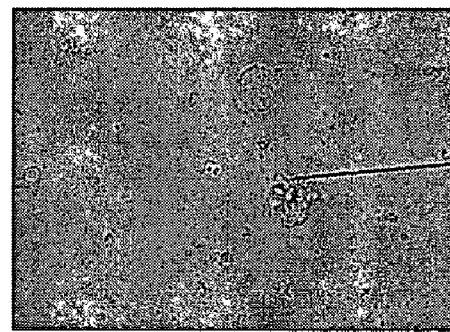
FIG. 12H — 940
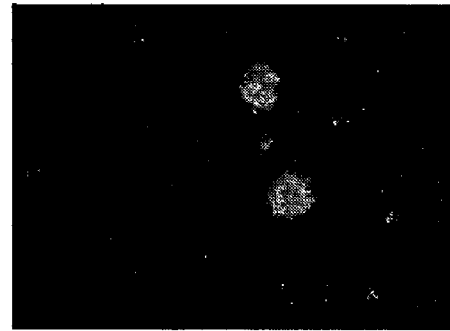
FIG. 12I — 940
FIG. 12J — 941

```
                        SEQUENCE LISTING

<160> NUMBER OF SEQ ID NOS: 14

<210> SEQ ID NO 1
<211> LENGTH: 18
<212> TYPE: DNA
<213> ORGANISM: Artificial
<220> FEATURE:
<223> OTHER INFORMATION: Synthetic oligonucleotide
<220> FEATURE:
<221> NAME/KEY: Fluorescein
<222> LOCATION: (1)..(1)

<400> SEQUENCE: 1
ttggtcatcc atggctct                                                    18

<210> SEQ ID NO 2
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: Fluorescein
<222> LOCATION: (1)..(1)
<220> FEATURE:
<221> NAME/KEY: misc_feature
<222> LOCATION: (20)..(21)
<223> OTHER INFORMATION: deoxythymidine

<400> SEQUENCE: 2
uucuccgaac gugucacgut t                                                21
```

<210> SEQ ID NO 3
<211> LENGTH: 9
<212> TYPE: DNA
<213> ORGANISM: Artificial sequence
<220> FEATURE:
<223> OTHER INFORMATION: Synthetic

<400> SEQUENCE: 3 tgacttgga                                                                9

<210> SEQ ID NO 4
<211> LENGTH: 9
<212> TYPE: DNA
<213> ORGANISM: Artificial sequence
<220> FEATURE:
<223> OTHER INFORMATION: Synthetic oligonucleotide

<400> SEQUENCE: 4 tgacccgga                                                                9

<210> SEQ ID NO 5
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 5
ctaccatctt ggccacttca g                                                 21

<210> SEQ ID NO 6
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 6
gcacaggagc gaactctttc c                                                 21

<210> SEQ ID NO 7
<211> LENGTH: 13
<212> TYPE: DNA
<213> ORGANISM: Artificial sequence
<220> FEATURE:
<223> OTHER INFORMATION: Synthetic oligonucleotide

<400> SEQUENCE: 7
gaacctcctt tac                                                          13

<210> SEQ ID NO 8
<211> LENGTH: 13
<212> TYPE: DNA
<213> ORGANISM: Artificial sequence
<220> FEATURE:
<223> OTHER INFORMATION: Synthetic oligonucleotide

<400> SEQUENCE: 8
gagcctcctg tac                                                          13

<210> SEQ ID NO 9
<211> LENGTH: 9
<212> TYPE: DNA
<213> ORGANISM: Artificial sequence
<220> FEATURE:
<223> OTHER INFORMATION: Synthetic oligonucleotide

```
<400> SEQUENCE: 9 tgacttgga                                                                 9

<210> SEQ ID NO 10
<211> LENGTH: 9
<212> TYPE: DNA
<213> ORGANISM: Artificial sequence
<220> FEATURE:
<223> OTHER INFORMATION: Synthetic oligonucleotide

<400> SEQUENCE: 10 tgacccgga                                                                 9

<210> SEQ ID NO 11
<211> LENGTH: 9
<212> TYPE: DNA
<213> ORGANISM: Artificial sequence
<220> FEATURE:
<223> OTHER INFORMATION: Synthetic oligonucleotide

<400> SEQUENCE: 11 aaccggtaa                                                                 9

<210> SEQ ID NO 12
<211> LENGTH: 9
<212> TYPE: DNA
<213> ORGANISM: Artificial sequence
<220> FEATURE:
<223> OTHER INFORMATION: Synthetic oligonucleotide

<400> SEQUENCE: 12 aactggtaa                                                                 9

<210> SEQ ID NO 13
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 13
ccagatcttc g                                                             11

<210> SEQ ID NO 14
<211> LENGTH: 11
<212> TYPE: DNA
<213> ORGANISM: Artificial sequence
<220> FEATURE:
<223> OTHER INFORMATION: Synthetic oligonucleotide

<400> SEQUENCE: 14
ccagctcttc g                                                             11
```

THERAPY FOR LYSOSOMAL ENZYME DEFICIENCIES

RELATED APPLICATIONS

This application claims benefit of U.S. Provisional Patent Application 60/610,872 filed Sep. 17, 2004, and is a continuation-in-part of co-pending application Ser. No. 10/869,693 filed Jun. 16, 2004; the entire contents of both are incorporated by reference for all purposes.

BACKGROUND OF THE INVENTION

Lysosomal storage disorders (LSDs) are a group of approximately fifty inherited metabolic diseases that result from cellular deficiencies of a specific lysosomal enzyme, receptor target, activator protein, membrane protein, or transporter that leads to pathogenic accumulation of substances in lysosomes, causing accumulation of the substrate, resulting in deterioration of cellular and tissue function. Wilcox, W. R., Lysosomal storage disorders: the need for better pediatric recognition and comprehensive care. J Pediatr. 2004 May; 144(5 Suppl):S3-14. Lysosomal storage disorders occur in approximately 1 in 5,000 live births and display considerable clinical and biochemical heterogeneity. The majority of lysosomal storage disorders are inherited as autosomal recessive conditions although two examples of X-linked are MPS II and Fabry disease.

The extent and severity of the lysosomal storage disorder depend on the type and amount of substrate that accumulates, but almost all disorders are progressive. Most disorders have both central nervous system and systemic manifestations, whereas some affect either just the central nervous system or tissues outside the nervous system. Many patients with lysosomal storage disorders die in infancy or childhood, and patients who survive to adulthood often have a decreased lifespan and significant morbidity (Wilcox, 2004). Table 1, below, is a summary of some of the lysosomal storage disorders listed by the lysosomal function that is affected.

Gaucher disease is the most prevalent lysosomal storage disorder and results from the deficiency of glucocerebrosidase (GC; EC 3.2.1.45) in all tissues. This enzyme deficiency produces accumulation of glucosylceramide in lipid laden macrophages (called Gaucher cells) in the reticulendothelial system including liver, spleen, lung, and bone marrow. Gaucher disease has been categorized into three major phenotypes: type 1, normeuronopathic; type 2, acute neuronopathic, and type 3, subacute neuronopathic. The spectrum of illness severity for type 1 Gaucher disease is diverse, where children and adults can be asymptomatic or may have severely debilitating symptoms, including skeletal degeneration, anemia, thrombocytopenia and hepatosplenomegaly. Symptoms can present at any age, and although type 1 Gaucher disease is more common among the Ashkenazi Jewish population, it occurs in all ethnic groups. Type 2 (acute neuronopathic) Gaucher disease is rapidly progressive, where by six months of age, most type 2 infants have brainstem dysfunction, and succumb to complications such as respiratory arrest or aspiration pneumonia at 18-24 months of age. Type 3 patients develop neurological abnormalities at a later age than type 2 patients; most only develop a subtle horizontal saccadic eye movement defect. Systemic complications in types 1 and 3 Gaucher patients respond to enzyme therapy.

Enzyme replacement therapy (ERT) for Gaucher disease was first approved by the FDA in 1991. Long-term ERT does improve the organomegaly and blood counts in most Gaucher patients. However, the current formulation of IV administered GC enzyme does not alter the neurological deterioration in type 2 patients or significantly reverse skeletal complications. To overcome the current limitations of ERT for Gaucher disease we propose to apply a novel technique that uses orally administered microscopic yeast cell wall particles containing DNA comprised of sequences encoding human glucocerebrosidase to more efficiently deliver normal or modified GC enzyme to macrophages. In addition to improved delivery of GC enzyme to all tissues, we expect this innovative approach will provide a more efficient and specific uptake by macrophages in bone of the particles that deliver the DNA

TABLE 1

Lysosomal storage disorders by affected lysosomal function
(Wilcox, W. R., J Pediatr. 2004 May; 144(5 Suppl): S3-14)

| Lysosomal function affected | Disorder |
| --- | --- |
| Defective metabolism of glycosaminoglycans | MPS I-IX (Hurler, Scheie, Hunter, Sanfilippo, Morquio, Maroteaux-Lamy, Sly diseases, hyaluronidase deficiency) |
| Defective degradation of glycan portion of glycoproteins | Aspartylglucosaminuria, fucosidosis, mannosidosis, Schindler disease, sialidosis type I |
| Defective degradation of glycogen | Pompe disease |
| Defective degradation of sphingolipid components | Fabry disease, Farber disease, Gaucher disease (types 1-3) GM1-gangliosidosis, GM2-gangliosidoses (Tay-Sachs disease, Sandhoff disease, GM2 activator disease), Krabbe disease, metachromatic leukodystrophy, Niemann-Pick disease (type A or B). |
| Defective degradation of polypeptides | Pycnodysostosis |
| Defective degradation or transport of cholesterol, cholesterol esters, or other complex lipids | Ceroid lipofuscinosis (multiple types with different defects, some not known yet), cholesterol ester storage disease, Niemann-Pick disease type C, Wolman disease |
| Multiple deficiencies of lysosomal enzymes | Multiple sulfatase, galactosialidosis, mucolipidosis types II, III |
| Transport and trafficking defects | Cystinosis, mucolipidosis IV, sialic acid storage disorder, chylomicron retention disease with Marinesco-Sjogren syndrome, Hermansky-Pudlak syndrome (several forms), Chediak-Higashi syndrome, and Danon disease |
| Unknown defects | Geleophysic dysplasia, Marinesco-Sjogren syndrome | encoding the normal or modified GC. This approach can lead to greater improvement in skeletal complications that are not significantly reversed by current ERT.

Extracted yeast cell wall particles are readily available, biodegradable, substantially spherical particles about 2-4 μm in diameter. Preparation of extracted yeast cell wall particles is known in the art, and is described, for example in U.S. Pat. Nos. 4,992,540; 5,082,936; 5,028,703; 5,032,401; 5,322,841; 5,401,727; 5,504,079; 5,968,811; 6,444,448 B1; 6,476,003 B1; published U.S. applications 2003/0216346 A1, 2004/0014715 A1, and PCT published application WO 02/12348 A2. A form of extracted yeast cell wall particles, referred to as "whole glucan particles," have been suggested as delivery vehicles, but have been limited either to release by simple diffusion of active ingredient from the particle or release of an agent chemically crosslinked to the whole glucan particle by biodegradation of the particle matrix. See U.S. Pat. Nos. 5,032,401 and 5,607,677.

Extracted yeast cell wall particles, primarily due to their beta-glucan content, are targeted to phagocytic cells, such as macrophages and cells of lymphoid tissue. The mucosal-associated lymphoid tissue (MALT) comprises all lymphoid cells in epithelia and in the lamina propria lying below the body's mucosal surfaces. The main sites of mucosal-associated lymphoid tissues are the gut-associated lymphoid tissues (GALT), and the bronchial-associated lymphoid tissues (BALT).

Another important component of the GI immune system is the M or microfold cell. M cells are a specific cell type in the intestinal epithelium over lymphoid follicles that endocytose a variety of protein and peptide antigens. Instead of digesting these proteins, M cells transport them into the underlying tissue, where they are taken up by local dendritic cells and macrophages.

M cells take up molecules and particles from the gut lumen by endocytosis or phagocytosis. This material is then transported through the interior of the cell in vesicles to the basal cell membrane, where it is released into the extracellular space. This process is known as transcytosis. At their basal surface, the cell membrane of M cells is extensively folded around underlying lymphocytes and antigen-presenting cells, which take up the transported material released from the M cells and process it for antigen presentation.

A study has shown that transcytosis of yeast particles (3.4+/−0.8 micron in diameter) by M cells of the Peyer's patches takes less than 1 hour (Beier, R., & Gebert, A., Kinetics of particle uptake in the domes of Peyer's patches, Am J. Physiol. 1998 July; 275(1 Pt 1):G130-7). Without significant phagocytosis by intraepithelial macrophages, the yeast particles migrate down to and across the basal lamina within 2.5-4 hours, where they quickly get phagocytosed and transported out of the Peyer's patch domes. M cells found in human nasopharyngeal lymphoid tissue (tonsils and adenoids) have been shown to be involved in the sampling of viruses that cause respiratory infections. Studies of an in vitro M cells model have shown uptake of fluorescently labeled microspheres (Fluospheres, 0.2 μm) and chitosan microparticles (0.2 μm) van der Lubben I. M., et al., Transport of chitosan microparticles for mucosal vaccine delivery in a human intestinal M-cell model, J Drug Target, 2002 September; 10(6):449-56. A lectin, *Ulex europaeus* agglutinin 1 (UEA1, specific for alpha-L-fucose residues) has been used to target either polystyrene microspheres (0.5 μm) or polymerized liposomes to M cells (0.2 μm) (Clark, M. A., et al., Targeting polymerised liposome vaccine carriers to intestinal M cells, Vaccine. 2001 Oct. 12;20(1-2):208-17). In vivo studies in mice have reported that poly-D,L-lactic acid (PDLLA) microspheres or gelatin microspheres (GM) can be efficiently taken up by macrophages and M cells. (Nakase, H., et al., Biodegradable microspheres targeting mucosal immune-regulating cells: new approach for treatment of inflammatory bowel disease, J Gastroenterol. 2003 March; 38 Suppl 15:59-62).

However, it has been reported that uptake of synthetic particulate delivery vehicles including poly(DL-lactide-co-glycolide) microparticles and liposomes is highly variable, and is determined by the physical properties of both particles and M cells. Clark, M. A., et al., Exploiting M cells for drug and vaccine delivery, Adv Drug Deliv Rev. 2001 Aug. 23;50 (1-2):81-106. The same study reported that delivery may be enhanced by coating the particles or liposomes with reagents including appropriate lectins, microbial adhesins and immunoglobulins which selectively bind to M cell surfaces. See also, Florence, A. T., The oral absorption of micro- and nano-particulates: neither exceptional nor unusual, Pharm Res. 1997 March;14(3):259-66.

Pathogen pattern recognition receptors (PRRs) recognize common structural and molecular motifs present on microbial surfaces and contribute to induction of innate immune responses. Mannose receptors and beta-glucan receptors in part participate in the recognition of fungal pathogens. The mannose receptor (MR), a carbohydrate-binding receptor expressed on subsets of macrophages, is considered one such PRR. Macrophages have receptors for both mannose and mannose-6-phosphate that can bind to and internalize molecules displaying these sugars. The molecules are internalized by endocytosis into a pre-lysosomal endosome. This internalization has been used to enhance entry of oligonucleotides into macrophages using bovine serum albumin modified with mannose-6-phosphate and linked to an oligodeoxynucleotide by a disulfide bridge to a modified 3' end; see Bonfils, E., et al., Nucl. Acids Res. 1992 20, 4621-4629. see E. Bonfils, C. Mendes, A. C. Roche, M. Monsigny and P. Midoux, Bioconj. Chem., 3, 277-284 (1992). Macrophages also express beta-glucan receptors, including CR3 (Ross, G. D., J. A. Cain, B. L. Myones, S. L. Newman, and P. J. Lachmann. 1987. Specificity of membrane complement receptor type three ($CR_3$) for β-glucans. *Complement Inflamm.* 4:61), dectin-1. (Brown, G. D. and S. Gordon. 2001. Immune recognition. A new receptor for β-glucans. *Nature* 413:36.), and lactosylceramide (Zimmerman J W, Lindermuth J, Fish P A, Palace G P, Stevenson T T, DeMong D E. A novel carbohydrate-glycosphinglipid interaction between a beta-(1-3)-glucan immunomodulator, PGG-glucan, and lactosylceramide of human leukocytes. J Biol. Chem. 1998 Aug. 21:273(34): 22014-20.). The beta-glucan receptor, $CR_3$ is predominantly expressed on monocytes, neutrophils and NK cells, whereas dectin-1 is predominantly expressed on the surface of cells of the macrophages. Lactosylceramide is found at high levels in M cells. Microglia can also express a beta-glucan receptor (Muller, C. D., et al. Functional beta-glucan receptor expression by a microglial cell line, Res Immunol. 1994 May; 145 (4):267-75).

There is evidence for additive effects on phagocytosis of binding to both mannose and beta-glucan receptors. Giaimis et al. reported observations suggesting that phagocytosis of unopsonized heat-killed yeast (*S. cerevisiae*) by murine macrophage-like cell lines as well as murine peritoneal resident macrophages is mediated by both mannose and beta-glucan receptors. To achieve maximal phagocytosis of unopsonized heat-killed yeast, coexpression of both mannose and beta-glucan receptors is required (Giaimis, J., et al., Both mannose and beta-glucan receptors are involved in phagocytosis of unopsonized, heat-killed *Saccharomyces cerevisiae* by murine macrophages, J Leukoc Biol. 1993 December; 54(6): 564-71).

SUMMARY OF THE INVENTION

Lysosomal disorders can be treated through macrophage-targeted expression of the deficient gene by oral administration using the compositions and methods of the present invention. In preferred embodiments, plasmid DNAs expressing lysosomal enzymes are incorporated into yeast glucan particles (YGP) and yeast glucan-mannan particles (YGMP) in the form of cationic polymer-DNA nanocomplexes. These YGP-DNA and YGMP-DNA microparticles are systemically, mucosally and orally bioavailable through receptor mediated uptake into tissue, mucosal and gut associated lymphatic tissue (GALT) macrophages via carbohydrate receptor binding to the particle surface glucan and mannan polysaccharides. Upon phagocytosis the particles are engulfed into an endosomal compartment where the cationic polymer releases the DNA and swells the endosome releasing the DNA into the cytoplasm. Incorporation of excipients into the YGP-DNA and YGMP-DNA formulations facilitate endosomal DNA release and nuclear uptake. The delivery of DNA expressing the deficient protein leads to the supplementation, preferably the restoration, of the activity of the deficient protein and catalyzes the breakdown of the toxic accumulated storage product.

In preferred embodiments, the present invention provides a composition, i.e., a therapeutic delivery system, comprising an extracted yeast cell wall defining an internal space and comprising beta-glucan, preferably less than about 90 weight percent beta-glucan, more preferably about 6 to about 90 weight percent beta-glucan, a payload trapping molecule and a payload molecule or molecules, wherein the payload molecule and the payload trapping molecule are soluble in the same solvent system and wherein the payload molecule supplements the function of an absent, defective or inhibited gene or gene product. Typically, the payload molecule is selected from the group consisting of a nucleic acid, a peptide, a protein and a mixture thereof, and is present in the composition in an amount effective to supplement the function of a deficient lysosomal enzyme. In certain preferred embodiments, the extracted yeast cell wall further comprises mannan, preferably more than about 30 weight percent mannan, more preferably between about 30 to about 90 weight percent mannan. In other embodiments, YCP particles have a substantially higher chitin+chitosan content compared to the other particle types, generally more than 50 weight percent, more preferably between about 50 to about 75 weight percent. In certain embodiments, the nucleic acid is selected from the group consisting of an oligonucleotide, an antisense construct, a siRNA, an enzymatic RNA, a recombinant DNA construct and a mixture thereof. In preferred embodiments, the recombinant DNA construct is an expression vector comprising a control element operatively linked to an open reading frame encoding a protein. Typically, the protein encoded by the open reading frame is a structural protein, a protein having enzymatic activity, a membrane protein, a DNA binding protein or a signaling protein or a functional equivalent thereof. Preferably, the nucleic acid comprises a nucleotide sequence that supplements the function of an absent, defective or inhibited gene. In other embodiments, the present invention provides for the use of the composition for the manufacture of a pharmaceutical composition for the treatment of a lysosomal enzyme deficiency.

In certain preferred embodiments, the protein encoded by the open reading frame is a protein that produces a therapeutic effect in a subject having a genetic disorder, in particular, a lysosomal storage disorder. In particularly preferred embodiments, the protein encoded by the open reading frame is human glucocerebrosidase or its functional equivalent.

Suitably, the genetic disorder is a defective metabolism of glycosaminoglycans, a defective degradation of the glycan portion of glycoproteins, a defective degradation of glycogen, a defective degradation of sphingolipid components, a defective degradation of polypeptides, a defective degradation or transport of cholesterol, cholesterol esters, or other complex lipids, a deficiency of multiple lysosomal enzymes, a transport defect or a intracellular trafficking defect. In preferred embodiments, the genetic disorder is Hurler disease, Scheie disease, Hunter disease, Sanfilippo disease, Morquio disease, Maroteaux-Lamy disease, Sly disease, a hyaluronidase deficiency, aspartylglucosaminuria, fucosidosis, mannosidosis, Schindler disease, sialidosis type I, Pompe disease, Fabry disease, Farber disease, Gaucher disease type 1, Gaucher disease type 2, Gaucher disease type 3, a GM1-gangliosidosis, a GM2-gangliosidosis such as Tay-Sachs disease or Sandhoff disease, a GM2 activator disease, Krabbe disease, a metachromatic leukodystrophy, Niemann-Pick disease type A, Niemann-Pick disease type B, a pycnodysostosis, a ceroid lipofuscinosis, a cholesterol ester storage disease, Niemann-Pick disease type C, Wolman disease, a multiple sulfatase disease, a galactosialidosis, mucolipidosis type II, mucolipidosis type III, a cystinosis, mucolipidosis IV, a sialic acid storage disorder, chylomicron retention disease with Marinesco-Sjögren syndrome, Hermansky-Pudlak syndrome, Chediak-Higashi syndrome, and Danon disease, geleophysic dysplasia, or Marinesco-Sjögren syndrome.

In particularly preferred embodiments, the recombinant DNA construct is an expression vector comprising a control element operatively linked to an open reading frame encoding a protein, preferably an enzyme, more preferably a lysosomal enzyme. In other preferred embodiments, the recombinant DNA construct is an expression vector comprising a control element operatively linked to an open reading frame encoding a lysosomal enzyme activator. In certain embodiments, the lysosomal enzyme activator is selected from the group consisting of saprosin A, saprosin B, saprosin C, saprosin D and a mixture thereof. In other embodiments, the lysosomal enzyme activator is $G_{M2}$ activator protein ($G_{M2}AP$), or other lysosomal protein activators.

In other embodiments, the payload molecule is a protein, preferably a lysosomal enzyme. In other embodiments, the payload molecule is a protein selected from the group consisting of saprosin A, saprosin B, saprosin C, saprosin D, $G_{M2}$ activator protein and a mixture thereof.

In other embodiments, the invention provides a pharmaceutical composition comprising the therapeutic delivery system and a pharmaceutically acceptable excipient. In preferred embodiments, the composition is suitable for oral administration. In other preferred embodiments, the composition is formulated for parenteral administration, most preferably for subcutaneous or intramuscular administration. In other preferred embodiments, the composition is formulated for mucosal administration.

The present invention also provides a method of supplementing an enzymatic or other protein deficiency in a cell including the steps of providing an effective amount of a first therapeutic delivery system comprising an extracted yeast cell wall comprising beta-glucan, a payload trapping molecule and a payload molecule, wherein the payload molecule is an expression vector comprising a control element operatively linked to an open reading frame encoding the deficient protein, such as an enzyme; and contacting a cell having such a protein or enzymatic deficiency with the first therapeutic delivery system. The step of contacting the cell can be performed in vitro or in vivo. In preferred embodiments, the first therapeutic delivery system is internalized by the cell, typically by phagocytosis. The method can further include the steps of providing an effective amount of a second therapeutic delivery system comprising an extracted yeast cell wall comprising beta-glucan, a payload trapping molecule and a payload molecule, wherein the payload molecule is an expression vector comprising a control element operatively linked to an open reading frame encoding an activator of the deficient enzyme and contacting the cell having such a protein or enzymatic deficiency with the second therapeutic delivery system.

The cell that can be suitably treated can be a macrophage, an M cell of a Peyer's patch, a monocyte, a neutrophil, a dendritic cell, a Langerhans cell, a Kupffer cell, an alveolar phagocyte, a peritoneal macrophage, a milk macrophage, a microglial cell, an eosinophil, a granulocytes, a mesengial phagocyte or a synovial A cell.

In another aspect, the present invention provides method of supplementing an protein or enzymatic deficiency in a cell including the steps of providing an effective amount of a first therapeutic delivery system comprising an extracted yeast cell wall comprising beta-molecule is a protein having the activity of the deficient enzyme; and contacting a cell having such an enzymatic or protein deficiency with the first therapeutic delivery system. The step of contacting the cell can be performed in vitro or in vivo. In preferred embodiments, the first therapeutic delivery system is internalized by the cell, typically by phagocytosis. The method can further include the steps of providing an effective amount of a second therapeutic delivery system comprising an extracted yeast cell wall comprising beta-glucan, a payload trapping molecule and a payload molecule, wherein the payload molecule is a protein having the activity of an activator of the deficient protein or enzyme and contacting the cell having such an enzymatic or protein deficiency with the second therapeutic delivery system.

In other embodiments, the present invention provides method of treating a subject having a lysosomal storage disorder including the step of administering an effective amount of a first therapeutic delivery system comprising an extracted yeast cell wall comprising beta-glucan, a payload trapping molecule and a payload molecule, wherein the payload molecule is an expression vector comprising a control element operatively linked to an open reading frame encoding the deficient lysosomal enzyme. The method can also include the step of administering an effective amount of a second therapeutic delivery system comprising an extracted yeast cell wall comprising beta-glucan, a payload trapping molecule and a payload molecule, wherein the payload molecule is an expression vector comprising a control element operatively linked to an open reading frame encoding an activator of the deficient lysosomal enzyme. The therapeutic delivery system is preferably administered orally to the subject. Alternatively, therapeutic delivery system is administered parenterally (subcutaneously, intradermally or intramuscularly or mucosally (skin, inhalation) to the subject. In other embodiments, the therapeutic delivery system of the present invention can be administered to a fetus in utero by administering the therapeutic delivery system to the mother, or by placing an effective amount of the therapeutic delivery system in the amniotic fluid.

The foregoing and other features and advantages of the particulate drug delivery system and methods will be apparent from the following more particular description of preferred embodiments of the system and method as illustrated in the accompanying drawings in which like reference characters refer to the same parts throughout the different views.

BRIEF DESCRIPTION OF THE DRAWINGS

FIG. 6A is a grayscale image of a color transmitted light photomicrograph of J774 cells, e.g., an indicated cell 510, from an untreated control culture.

FIG. 6B is a grayscale image of a color fluorescence photomicrograph of the same field of J774 cells showing a lack of fluorescently labeled cells.

FIG. 6C is a grayscale image of a color combined light and fluorescence photomicrograph of J774 cells exposed to a formulation of fluorescently labeled yeast cell wall particles (YGP-F) showing cells, e.g., cell 912, containing fluorescently labeled particles.

FIGS. 6D and 6E are grayscale images of a color transmitted light photomicrograph and color fluorescence photomicrograph, respectively, of the same field of J774 cells exposed to a formulation of yeast cell wall particles containing pMFG-GC expression vectors (YGP:pMFG-GC:PEI:CTAB) showing expression of human glucocerebrosidase (hGC) by immunoreactivity in fluorescently labeled cells, e.g., cell 914.

FIGS. 6F and 6G are grayscale images of a color transmitted light photomicrograph and color fluorescence photomicrograph, respectively, of the same field of J774 cells exposed to a formulation of yeast cell wall particles containing pMFG-GC expression vectors (YGP-CN:pMFG-GC:CTAB) showing expression of human glucocerebrosidase (hGC) by immunoreactivity in fluorescently labeled cells, e.g., cell 916.

FIGS. 11A-11D are grayscale images of a color fluorescence photomicrographs of splenic macrophage cells isolated from mice treated in vivo showing uptake of yeast cell wall particles containing pIRES expression vectors and expression of green fluorescent protein (GFP). The isolated cells were cultured to appropriate confluency, and adherent cells were formalin fixed, examined using fluorescence microscopy and photographed.

FIG. 11A is a grayscale image of a color fluorescence photomicrograph of splenic macrophage cells isolated from a wild type mouse that received oral gavage in vivo of PBS (control treatment) showing a lack of fluorescent macrophages.

FIG. 11B is a grayscale image of a color fluorescence photomicrograph of splenic macrophage cells isolated from a wild type mouse that received a subcutaneous injection in vivo of 0.1 ml of a YGP-pIRES formulation providing 100 ng of plasmid DNA per dose showing a fluorescent macrophage 930.

FIG. 11C is a grayscale image of a color fluorescence photomicrograph of splenic macrophage cells isolated from a wild type mouse that received an oral dose in vivo of 0.1 ml of a YGP-pIRES formulation providing 100 ng of plasmid DNA per dose showing a fluorescent macrophage 931.

FIG. 11D is a grayscale image of a color fluorescence photomicrograph of splenic macrophage cells isolated from a wild type mouse that received an oral dose in vivo of 0.1 ml of a YGMP-pIRES formulation providing 100 ng of plasmid DNA per dose showing a fluorescent macrophage 932.

FIGS. 12A-12M are images of photomicrographs of immunostained splenic macrophage cells isolated from mice treated in vivo showing uptake of yeast cell wall particles containing pMFG-GC expression vectors and expression of human glucocerebrosidase (hGC). The isolated cells were cultured to appropriate confluency, and adherent cells were formalin fixed. Fixed cells were processed for immunocytochemistry using a primary anti-human GC antibody (rabbit antisera), an appropriate detectable secondary antibody (goat anti-rabbit FITC conjugated antisera), examined using fluorescence microscopy and photographed.

FIG. 12A is an image of a color fluorescence photomicrograph of immunostained splenic macrophage cells isolated from a wild type mouse that received oral gavage in vivo of PBS (control treatment) showing a lack of hGC expressing fluorescent immunostained macrophages.

FIGS. 12B & 12C are images of a color transmitted light photomicrograph (12B) and a color fluorescence photomicrograph (12C) of immunostained splenic macrophage cells isolated from a wild type mouse that received a subcutaneous injection in vivo of 0.1 ml of a YGMP-pMFG-GC formulation providing 100 ng of plasmid DNA per dose showing a hGC expressing fluorescent immunostained macrophage 935.

FIG. 12D is an image of a color fluorescence photomicrograph of immunostained splenic macrophage cells isolated from a L444P −/− mutant mouse that received a subcutaneous injection in vivo of 0.1 ml of a YGP-pMFG-GC formulation providing 100 ng of plasmid DNA per dose showing a hGC expressing fluorescent immunostained macrophage 936.

FIG. 12E is an image of a color fluorescence photomicrograph of immunostained splenic macrophage cells isolated from a R463C −/− mutant mouse that received a subcutaneous injection in vivo of 0.1 ml of a YGP-pMFG-GC formulation providing 100 ng of plasmid DNA per dose showing a hGC expressing fluorescent immunostained macrophage 937.

FIGS. 12F & 12G are images of a color transmitted light photomicrograph (12F) and a color fluorescence photomicrograph (12G) of immunostained splenic macrophage cells isolated from a wild type mouse that received an oral dose in vivo of 0.1 ml of a YGP-pMFG-GC formulation providing 100 ng of plasmid DNA per dose showing hGC expressing fluorescent immunostained macrophages, e.g., macrophage 938.

FIGS. 12H & 12I are images of a color transmitted light photomicrograph (12H) and a color fluorescence photomicrograph (12I) of immunostained splenic macrophage cells isolated from a L444P −/− mutant mouse that received 30 days of treatment of an oral dose in vivo of 0.1 ml of a YGP-pMFG-GC formulation providing 100 ng of plasmid DNA per dose showing hGC expressing fluorescent immunostained macrophages, e.g., macrophage 940.

FIG. 12J is an image of a color fluorescence photomicrograph of immunostained splenic macrophage cells isolated from a R463C −/− mutant mouse that received an oral dose in vivo of 0.1 ml of a YGP-pMFG-GC formulation providing 100 ng of plasmid DNA per dose showing hGC expressing fluorescent immunostained macrophages, e.g., macrophage 941.

FIG. 12K is an image of a color fluorescence photomicrograph of immunostained splenic macrophage cells isolated from a wild type mouse that received an oral dose in vivo of 0.1 ml of a YGMP-pMFG-GC formulation providing 100 ng of plasmid DNA per dose showing hGC expressing fluorescent immunostained macrophages, e.g., macrophage 942.

FIG. 12L is an image of a color fluorescence photomicrograph of immunostained splenic macrophage cells isolated from a L444P −/− mutant mouse that received an oral dose in vivo of 0.1 ml of a YGMP-pMFG-GC formulation providing 100 ng of plasmid DNA per dose showing hGC expressing fluorescent immunostained macrophages, e.g., macrophage 943.

FIG. 12M is an image of a color fluorescence photomicrograph of immunostained splenic macrophage cells isolated from a R463C −/− mutant mouse that received an oral dose in vivo of 0.1 ml of a YGMP-pMFG-GC formulation providing 100 ng of plasmid DNA per dose showing hGC expressing fluorescent immunostained macrophages, e.g., macrophage 944.

Figure 1:
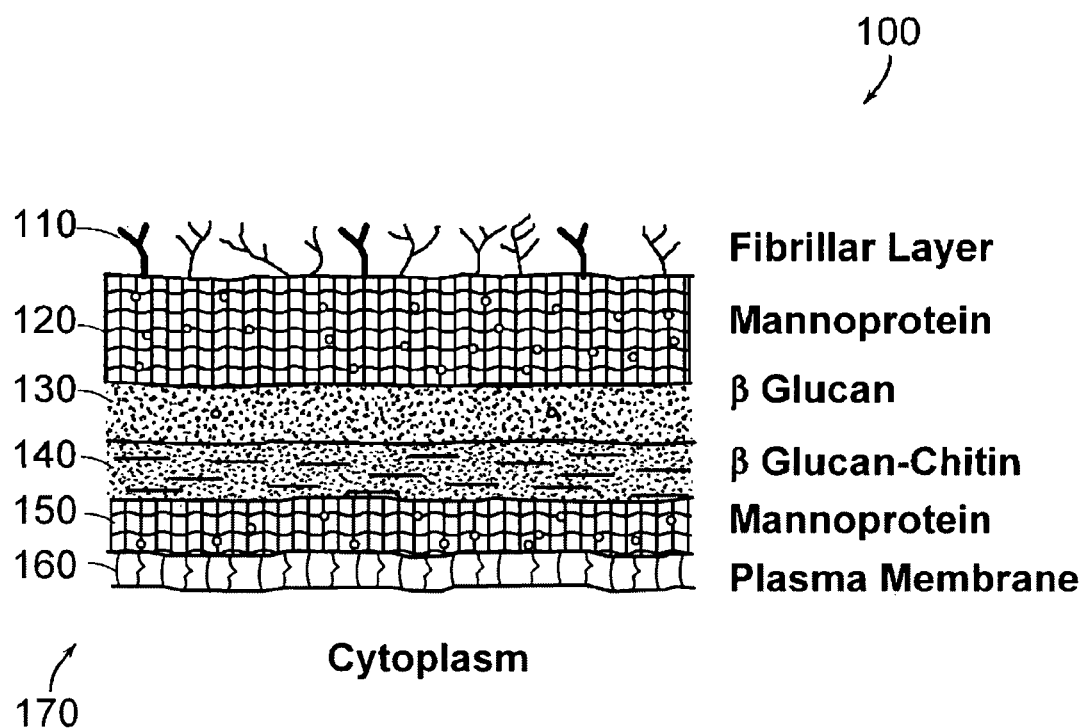
FIG. 1 is a schematic diagram 100 of a transverse section of a yeast cell wall, showing, from outside to inside, an outer fibrillar layer 110, an outer mannoprotein layer 120, a beta glucan layer 130, a beta glucan—chitin layer 140, an inner mannoprotein layer 150, the plasma membrane 160 and the cytoplasm 170.

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

The present invention provides a therapeutic delivery system comprising an extracted yeast cell wall comprising beta-glucan, a payload trapping molecule and a payload molecule, wherein the payload molecule and the payload trapping molecule are soluble in the same solvent system wherein the payload molecule supplements the function of the deficient lysosomal enzyme. The invention further provides methods of making and methods of using the therapeutic delivery system.

Advantageously, the composition and method of the present invention inherently directly targets macrophages and supplements the deficit of the lysosomal protein, such as an enzyme in the macrophages. Administering the therapeutic delivery system of the present invention by oral or mucosal or parenteral routes serves to avoid adverse effects of intravenous enzyme or protein replacement therapy. Supplementing the enzymatic or protein deficit by supplying an expression vector instead of the encoded protein itself serves to minimize or avoid antigenic reactions. The method of the present invention can also be used to normalize endogenous lysosomal enzyme activity by supplementing lysosomal enzyme activators, such as saprosin C.

Advantagously, by targeting macrophages and other phagocytic cells, the present invention provides a means of delivering the therapeutic system to a diverse range of locations such as bone, kidney, lung, gastrointestinal tract and brain. While not being held to a particular theory, it is believed that the migration of macrophages and other phagocytic cells to a site is determined in part by one or more stimuli, such as inflammation, lipid, or other physiological macrophage attractants. Under this model, it is believed that the population of phagocytic cells bearing the therapeutic delivery system of the present invention in any particular tissue is in dynamic equilibrium with similar populations in other tissues. Hence, the population of phagocytic cells bearing the therapeutic delivery system in any particular tissue, and thus the supplementation of the deficient endogenous enzyme, may fluctuate in time, responding, at least in part, to the physiological influences that act to regulate macrophage and other phagocytic cell distribution and activity.

In general, the compositions and methods of the present invention provide simple, efficacious and efficient delivery of therapeutic agents in vivo, preferably by oral administration. The compositions have improved stability compared to available compostions, and have further advantages in patient convenience (and thus, patient compliance), lower costs and decreased or reduced side effects.

Definitions

"Subject" means mammals and non-mammals. "Mammal" means any member of the class Mammalia including, but not limited to, humans, non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

A "therapeutic effect" means an amelioration of the symptoms or reduction of progression of the disease; in a lysosomal enzyme deficiency, "therapeutic effect" means a detectible supplementation of the function of the deficient gene or the function of the deficient gene product. A "therapeutically effective amount" means an amount of a compound that, when administered to a subject for treating a disease, is sufficient to effect such treatment for the disease. The "therapeutically effective amount" will vary depending on the compound, the disease state being treated, the severity or the disease treated, the age and relative health of the subject, the route and form of administration, the judgement of the attending medical or veterinary practitioner, and other factors. A "functional equivalent" of a protein means a molecule, protein or non-protein, that differs structurally from the protein but performs the same function as the protein under equivalent conditions. A "functional equivalent" of a lysosomal enzyme means a molecule, protein or non-protein, that differs structurally from the protein and catalyses the same reaction of the substrate of the native lysosomal enzyme under equivalent conditions.

The choice of the payload trapping molecule can confer specific characteristics to the particulate delivery system. In general, the preferred payload trapping molecule is biocompatible and pharmaceutically acceptable. As noted above, the payload molecule and the payload trapping molecule are soluble in the same solvent system. Suitable payload trapping molecules include natural and synthetic polymers. In certain embodiments, the physical characteristics of the payload trapping molecule, such as agarose or polyacrylamide, provide useful advantages Suitable polymers include polysaccharides. In preferred embodiments, the polysaccharide selected is from the group consisting of agarose, an alginate, a xanthan, a dextran, a chitosan, a galactomannan gum, a derivative thereof and a mixture thereof. In certain preferred embodiments, the polysaccharides have been derivatized to produce cationic or anionic characteristics at physiological pH.

In other embodiments, the payload trapping molecule is a charged molecule at physiological pH, such as a cationic polymer, an anionic polymer, a cationic detergent, an anionic detergent and a mixture thereof. Preferred cationic polymers include chitosan, poly-L-lysine and polyethylenimines (PEIs), including substantially linear polyethylenimines, such as JetPEI, a commercially available linear polyethylenimine cationic polymer transfection reagent (Qbiogene, Inc., CA). Other cationic polymer transfection reagents are also suitable, preferably CytoPure™, a proprietary, commercially available, water-soluble cationic polymer transfection reagent (Qbiogene, Inc., CA). In other preferred embodiments, suitable anionic polymers include alginates, dextrans and xanthans, including derivatized alginates, dextrans and xanthans. In further preferred embodiments, the payload trapping molecule is a cationic detergent such as hexadecyltrimethylammoniumbromide. In one preferred embodiment, a mixture of a cationic detergent, such as hexadecyltrimethylammoniumbromide, and a cationic polymer, such as a polyethylenimine, is used. In another preferred embodiment, a mixture of a cationic detergent, such as hexadecyltrimethylammoniumbromide, and a cationic polymer, such as chitosan or PEI, can be used.

While not being held to a single hypothesis, it is believed that, in addition to facilitating the retention of the payload by the yeast cell wall particles, a preferred payload trapping molecule serves to encourage the release of the payload molecule from the endosome of a phagocytic cell by acting as a detergent, by helping to swell the endosome osmotically, or by other effects.

Payload Trapping Molecules

The payload trapping molecule is preferably a pharmaceutically acceptable excipient. The payload and trapping molecule are both soluble in the solvent system; the solvent system must be absorbed through the yeast cell particle carbohydrate matrix allowing the absorption of the payload and trapping polymer. The payload and trapping molecule are preferably water soluble. In preferred embodiments, the trapping molecule is biodegradable.

The mechanism of action of the trapping reaction with a given payload dictates the choice of payload trapping molecule. For electrostatic interactions a charged payload trapping molecule of opposite charge of the payload is required. For physical entrapment, the payload trapping molecule suitably participates in the formation of a matrix that reduces the diffusion of a payload. In other embodiments, the payload trapping molecule contributes a hydrophobic binding property that contributes to the retention of the payload. In further embodiments, the payload trapping molecule selectively binds to the payload, providing an affinity interaction that contributes to the retention of the payload.

In general, polyelectrolytes can be suitable payload trapping molecules. Several suitable polyelectrolytes are disclosed in U.S. Pat. No. 6,133,229. The polyelectrolyte may be a cationic or anionic polyelectrolyte. Amphoteric polyelectrolytes may also be employed. The cationic polyelectrolyte is preferably a polymer with cationic groups distributed along the molecular chain. The cationic groups, which in certain embodiments may include quaternary ammonium-derived moieties, may be disposed in side groups pendant from the chain or may be incorporated in it. Examples of cationic polyelectrolytes include: copolymers of vinyl pyrollidone and quaternary methyl methacrylate e.g., GAFQUAT® series (755N, 734, HS-100) obtained from ISP; substituted polyacrylamides; polyethyleneimine, polypropyleneimine and substituted derivatives; polyamine homopolymers (GOLCHEM® CL118); polyamine co-polymers (e.g., condensates of epichlorohydrin and mono or dimethylamine); polydiallyl dimethyl ammonium chloride (polyDADMAC); substituted dextrans; modified guar gum (substituted with hydroxypropytrimonium chloride); substituted proteins (e.g., quaternary groups substituted on soya protein and hydrolysed collagen); polyamino acids (e.g., polylysine); low molecular weight polyamino compounds (e.g., spermine and spermidine). Natural or artificial polymers may be employed. Cationic polyelectrolytes with MW 150 to 5,000,000, preferably 5000 to 500,000, more preferably 5000 to 100,000 may be employed. An amount of 0.01 to 10% is preferred, more preferably 0.1 to 2% w/v, especially 0.05 to 5%.

The anionic polyelectrolyte is preferably a polymer with anionic groups distributed along the molecular chain. The anionic groups, which may include carboxylate, sulfonate, sulphate or other negatively charged ionisable groupings, may be disposed upon groups pendant from the chain or bonded directly to the polymer backbone. Natural or artificial polymers may be employed.

Examples of anionic polyelectrolytes include: a copolymer of methyl vinyl ether and maleic anhydride, a copolymer of methyl vinyl ether and maleic acid, (Gantrez AN-series and S-series, respectively, International Specialty Products, Wayne, N.J.); alginic acid and salts; carboxymethyl celluloses and salts; substituted polyacrylamides (eg substituted with carboxylic acid groups); polyacrylic acids and salts; polystyrene sulfonic acids and salts; dextran sulphates; substituted saccharides e.g., sucrose octosulfate; heparin. Anionic polyelectrolytes with MW of 150 to 5,000,000 may be used, preferably 5000 to 500,000, more preferably 5000 to 100,000. An amount of 0.01% to 10% is preferred especially 0.05 to 5% more especially 0.1 to 2% w/v.

Biological polymers, such as polysaccharides, are preferred trapping polymers. Preferably, the polymers are processed to an average molecular weight to less than 100,000 Daltons. The polymers are preferably derivatized to provide cationic or anionic characteristics. Suitable polysaccharides include chitosan (deacetylated chitin), alginates, dextrans, such as 2-(diethylamino) ethyl ether dextran (DEAE-dextran) and dextran sulphate, xanthans, locust bean gums and guar gums.

Two general classes of cationic molecules are suitable for use as trapping molecules with negatively charged payloads such as nucleic acids: cationic polymers and cationic lipids.

A wide variety of cationic polymers have been shown to mediate in vitro transfection, ranging from proteins [such as histones (Fritz, J. D., et al, (1996) Hum. Gene Ther. 7, 1395-1404) and high mobility group (HMG) proteins (Mistry A. R., et al. (1997) BioTechniques 22, 718-729)] and polypeptides [such as polylysine (Wu, G. Y. & Wu, C. H. (1987) J. Biol. Chem. 262, 4429-4432, Wagner, E., et al., (1991) Bioconjugate Chem. 2, 226-231, short synthetic peptides (Gottschalk, S. et al., (1996) Gene Ther. 3, 448-457; Wadhwa, M. S., et al., (1997) Bioconjugate Chem. 8, 81-88), and helical amphiphilic peptides (Legendre, J. Y., et al., (1997) Bioconjugate Chem. 8, 57-63; Wyman, T. B., et al., (1997) Biochemistry 36, 3008-3017)] to synthetic polymers [such as polyethyleneimine (Boussif, O., et al., (1996) Gene Ther. 3, 1074-1080), cationic dendrimers (Tang, M. X., et al., (1996) Bioconjugate Chem. 7, 703-714; Haensler, J. et al., (1993) Bioconjugate Chem. 4, 372-379), and glucaramide polymers (Goldman, C. K., et al., (1997) Nat. Biotech. 15, 462-466)]. Other suitable cationic polymers include N-substituted glycine oligomers (peptoids) (Murphy, J. E., et al, A combinatorial approach to the discovery of efficient cationic peptoid reagents for gene delivery, Proc Natl Acad Sci. USA, 1998 95 (4)1517-1522), poly(2-methyl-acrylic acid 2-[(2-dimethylamino)-ethyl)-methyl-amino]-ethyl ester), abbreviated as pDAMA, and poly(2-dimethylamino ethyl)-methacrylate (PDMAEMA) (Funhoff, A. M., et al., 2004 Biomacromolecules, 5, 32-39).

Cationic lipids are also known in the art to be suitable for transfection. Feigner, P.L1, et al., Lipofection: a highly efficient, lipid-mediated DNA-transfection procedure. Proc Natl Acad Sci USA. 1987 84(21):7413-7. Suitable cationic lipids include N-[1-(2,3-dioleyloxy)propyl]-N,N,N-trimethylammonium chloride (DOTMA), [N,N,N',N'-tetramethyl-N,N'-bis(2-hydroxyethyl)-2,3-di(oleoyloxy)-1,4-butanediammonium iodide] (Promega Madison, Wis., USA), dioctadecylamidoglycyl spermine (Promega Madison, Wis., USA), N-[1-(2,3-Dioleoyloxy)]-N,N,N-trimethylammonium propane methylsulfate (DOTAP), N-[1-(2,3-dioleyloxy)propyl]-N,N,N-trimethylammonium chloride, 1,2-dimyristyloxypropyl-3-dimethyl-hydroxy ethyl ammonium bromide (DMRIE), dimyristoleoyl phosphonomethyl trimethyl ammonium (DMPTA) (see Floch et al. 1997. Cationic phosphonolipids as non-viral vectors for DNA transfection in hematopoietic cell lines and CD34+ cells. Blood Cells, Molec.& Diseases 23: 69-87), 1,2-dioleoyl-sn-glycero-3-phosphoethanolamine-N-(7-nitro-2-1,3-benzoxadiazol-4-yl), ammonium salt (Avanti Polar Lipids, Inc. Alabaster, Ala., US), 1,2-dioleoyl-3-trimethylammonium-propane chloride (Avanti Polar Lipids, Inc. Alabaster, Ala., US), 1,2-dioleoyl-sn-glycero-3-phosphoethanolamine (Avanti Polar Lipids, Inc. Alabaster, Ala., US) and 1,3-dioleoyloxy-2-(6-carboxyspermyl)propylamide (DOSPER).

Polyamines suitable as cationic trapping molecules are described in U.S. Pat. Nos. 6,379,965 and 6,372,499.

Payload Molecules

The particulate delivery system of the present invention is useful for in vivo or in vitro delivery of payload molecules including, but limited to, nucleic acids such as oligonucleotides, antisense constructs, siRNA, enzymatic RNA, and recombinant DNA constructs, including expression vectors.

In other preferred embodiments, the particulate delivery system of the present invention is useful for in vivo or in vitro delivery of payload molecules such as amino acids, peptides and proteins. By "protein" is meant a sequence of amino acids for which the chain length is sufficient to produce the higher levels of tertiary and/or quaternary structure. This is to distinguish from "peptides" or other small molecular weight drugs that do not have such structure. Typically, the protein herein will have a molecular weight of at least about 15-20 kD, preferably at least about 20 kD.

Examples of proteins encompassed within the definition herein include mammalian proteins, such as, e.g., growth hormone (GH), including human growth hormone, bovine growth hormone, and other members of the GH supergene family; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor VIIIC, factor IX tissue factor, and von Willebrands factor; anti-clotting factors such as Protein C; atrial natriuretic factor; lung surfactant; a plasminogen activator, such as urokinase or tissue-type plasminogen activator (t-PA); bombazine; thrombin; alpha tumor necrosis factor, beta tumor necrosis factor; enkephalinase; RANTES (regulated on activation normally T-cell expressed and secreted); human macrophage inflammatory protein (MIP-1-alpha); serum albumin such as human serum albumin; mullerian-inhibiting substance; relaxin A-chain; relaxin B-chain; prorelaxin; mouse gonadotropin-associated peptide; DNase; inhibin; activin; vascular endothelial growth factor (VEGF); receptors for hormones or growth factors; an integrin; protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-beta; platelet-derived growth factor (PDGF); fibroblast growth factor such as aFGF and bFGF; epidermal growth factor (EGF); transforming growth factor (TGF) such as TGF-alpha and TGF-beta, including TGF-beta1, TGF-beta2, TGF-beta3, TGF-beta4, or TGF-beta5; insulin-like growth factor-I and -II (IGF-I and IGF-II); des(1-3)-IGF-I (brain IGF-D; insulin-like growth factor binding proteins; CD proteins such as CD3, CD4, CD8, CD19 and CD20; osteoinductive factors; immunotoxins; a bone morphogenetic protein (BMP); T-cell receptors; surface membrane proteins; decay accelerating factor (DAF); a viral antigen such as, for example, a portion of the AIDS envelope; transport proteins; homing receptors; addressins; regulatory proteins; immunoadhesins; antibodies; and biologically active fragments or variants of any of the above-listed polypeptides.

The members of the GH supergene family include growth hormone, prolactin, placental lactogen, erythropoietin, thrombopoietin, interleukin-2, interleukin-3, interleukin-4, interleukin-5, interleukin-6, interleukin-7, interleukin-9, interleukin-10, interleukin-11, interleukin-12 (p35 subunit), interleukin-13, interleukin-15, oncostatin M, ciliary neurotrophic factor, leukemia inhibitory factor, alpha interferon, beta interferon, gamma interferon, omega interferon, tau interferon, granulocyte-colony stimulating factor, granulocyte-macrophage colony stimulating factor, macrophage colony stimulating factor, cardiotrophin-1 and other proteins identified and classified as members of the family.

The protein payload molecule is preferably essentially pure and desirably essentially homogeneous (i.e. free from contaminating proteins etc). "Essentially pure" protein means a composition comprising at least about 90% by weight of the protein, based on total weight of the composition, preferably at least about 95% by weight. "Essentially homogeneous" protein means a composition comprising at least about 99% by weight of protein, based on total weight of the composition. Proteins may be derived from naturally occurring sources or produced by recombinant technology. Proteins include protein variants produced by amino acid substitutions or by directed protein evolution (Kurtzman, A. L., et al., Advances in directed protein evolution by recursive genetic recombination: applications to therapeutic proteins, Curr Opin Biotechnol. 2001 12(4): 361-70) as well as derivatives, such as PEGylated proteins.

In certain embodiments, the protein is an antibody. The antibody may bind to any of the above-mentioned molecules, for example. Exemplary molecular targets for antibodies encompassed by the present invention include CD proteins such as CD3, CD4, CD8, CD19, CD20 and CD34; members of the HER receptor family such as the EGF receptor, HER2, HER3 or HER4 receptor; cell adhesion molecules such as LFA-1, Mol, p150,95, VLA-4, ICAM-1, VCAM and alphav/beta3 integrin including either alpha or beta subunits thereof (e.g., anti-CD11a, anti-CD18 or anti-CD11b antibodies); growth factors such as VEGF; IgE; blood group antigens; flk2/flt3 receptor; obesity (OB) receptor; protein C, etc.

In addition to peptides, polypeptides and nucleic acids, the particulate delivery system of the present invention is suitable for the delivery of smaller molecules, preferably for the delivery of pharmaceutically active agent, more preferably therapeutic small molecules. Suitable small molecule payloads for the delivery system of the present invention include contraceptive agents such as diethyl stilbestrol, 17-beta-estradiol, estrone, ethinyl estradiol, mestranol, and the like; progestins such as norethindrone, norgestryl, ethynodiol diacetate, lynestrenol, medroxyprogesterone acetate, dimethisterone, megestrol acetate, chlormadinone acetate, norgestimate, norethisterone, ethisterone, melengestrol, norethynodrel and the like; and spermicidal compounds such as nonylphenoxy-polyoxyethylene glycol, benzethonium chloride, chlorindanol and the like. Preferably, for such steroidal payloads, a mixture of trapping molecules is used, comprising a sufficient amount of a detergent to solubilize the payload and a polymer to retain the payload within the yeast cell wall particle.

Other active agents that can be incorporated in the delivery system of the present invention include gastrointestinal therapeutic agents such as aluminum hydroxide, calcium carbonate, magnesium carbonate, sodium carbonate and the like; non-steroidal antifertility agents; parasympathomimetic agents; psychotherapeutic agents; major tranquilizers such as chloropromazine HCl, clozapine, mesoridazine, metiapine, reserpine, thioridazine and the like; minor tranquilizers such as chlordiazepoxide, diazepam, meprobamate, temazepam and the like; rhinological decongestants; sedative-hypnotics such as codeine, phenobarbital, sodium pentobarbital, sodium secobarbital and the like; other steroids such as testosterone and testosterone propionate; sulfonamides; sympathomimetic agents; vaccines; vitamins and nutrients such as the essential amino acids, essential fats and the like; antimalarials such as 4-aminoquinolines, 8-aminoquinolines, pyrimethamine and the like; anti-migraine agents such as mazindol, phentermine and the like; anti-Parkinson agents such as L-dopa; anti-spasmodics such as atropine, methscopolamine bromide and the like; antispasmodics and anticholinergic agents such as bile therapy, digestants, enzymes and the like; antitussives such as dextromethorphan, noscapine and the like; bronchodilators; cardiovascular agents such as anti-hypertensive compounds, *Rauwolfia* alkaloids, coronary vasodilators, nitroglycerin, organic nitrates, pentaerythritotetranitrate and the like; electrolyte replacements such as potassium chloride; ergotalkaloids such as ergotamine with and without caffeine, hydrogenated ergot alkaloids, dihydroergocristine methanesulfate, dihydroergocomine methanesulfonate, dihydroergokrouyptine methanesulfate and combinations thereof; alkaloids such as atropine sulfate, Belladonna, hyoscine hydrobromide and the like; analgesics; narcotics such as codeine, dihydrocodienone, meperidine, morphine and the like; non-narcotics such as salicylates, aspirin, acetaminophen, d-propoxyphene and the like.

In preferred embodiments, the system of the present invention is used to deliver antibiotics such as the cephalosporins, chloramphenical, gentamicin, kanamycin A, kanamycin B, the penicillins, ampicillin, streptomycin A, antimycin A, chloropamtheniol, metronidazole, oxytetracycline penicillin G, the tetracyclines, and the like. In preferred embodiments, the ability of the body's macrophages to inactivate pathogens is enhanced by the delivery of antibiotics, such as tetracycline, to the macrophages.

In other preferred embodiments, the present invention provides a system to deliver anti-cancer agents; anti-convulsants such as mephenyloin, phenobarbital, trimethadione; anti-emetics such as thiethylperazine; antihistamines such as chlorophinazine, dimenhydrinate, diphenhydramine, perphenazine, tripelennamine and the like; anti-inflammatory agents such as hormonal agents, hydrocortisone, prednisolone, prednisone, non-hormonal agents, allopurinol, aspirin, indomethacin, phenylbutazone and the like; prostaglandins; cytotoxic drugs such as thiotepa, chlorambucil, cyclophosphamide, melphalan, nitrogen mustard, methotrexate and the like.

Vaccines

In preferred embodiments, the particulate delivery system of the present invention is useful in providing oral delivery of vaccines. In preferred embodiments, the system is used to deliver antigens, such as antigens of such microorganisms as *Neisseria gonorrhea, Mycobacterium tuberculosis,* Herpes virus (humonis, types 1 and 2), *Candida albicans, Candida tropicalis, Trichomonas vaginalis, Haemophilus vaginalis,* Group B *Streptococcus* sp., *Microplasma hominis, Hemophi-* lus ducreyi, Granuloma inguinale, Lymphopathia venereum, Treponema pallidum, Brucella abortus. Brucella melitensis, Brucella suis, Brucella canis, Campylobacter fetus, Campylobacter fetus intestinalis, Leptospira pomona, Listeria monocytogenes, Brucella ovis, equine herpes virus 1, equine arteritis virus, IBR-IBP virus, BVD-MB virus, Chlamydia psittaci, Trichomonas foetus, Toxoplasma gondii, Escherichia coli, Actinobacillus equuli, Salmonella abortus ovis, Salmonella abortus equi, Pseudomonas aeruginosa, Corynebacterium equi, Corynebacterium pyogenes, Actinobaccilus seminis, Mycoplasma bovigenitalium, Aspergillus fumigatus, Absidia ramosa, Trypanosoma equiperdum, Babesia caballi, Clostridium tetani, Clostridium botulinum and the like. In other embodiments, the system can be used to deliver neutralizing antibodies that counteract the above microorganisms.

In other embodiments, the system can be used to deliver enzymes such as ribonuclease, neuramidinase, trypsin, glycogen phosphorylase, sperm lactic dehydrogenase, sperm hyaluronidase, adenossinetriphosphatase, alkaline phosphatase, alkaline phosphatase esterase, amino peptidase, trypsin chymotrypsin, amylase, muramidase, acrosomal proteinase, diesterase, glutamic acid dehydrogenase, succinic acid dehydrogenase, beta-glycophosphatase, lipase, ATP-ase alpha-peptate gamma-glutamylotranspeptidase, sterol-3-beta-ol-dehydrogenase, DPN-di-aprorase.

In preferred embodiments, the system can deliver antigens of bioterrorism critical biological agents, including Category A agents such as variola major (smallpox), Bacillus anthracis (anthrax), Yersinia pestis (plague), Clostridium botulinum toxin (botulism), Francisella tularensis (tularaemia), filoviruses (Ebola hemorrhagic fever, Marburg hemorrhagic fever), arenaviruses (Lassa (Lassa fever), Junin (Argentine hemorrhagic fever) and related viruses); Category B agents such as Coxiella burnetti (Q fever), Brucella species (brucellosis), Burkholderia mallei (glanders), alphaviruses (Venezuelan encephalomyelitis, eastern & western equine encephalomyelitis), ricin toxin from Ricinus communis (castor beans), epsilon toxin of Clostridium perfringens; Staphylococcus enterotoxin B, Salmonella species, Shigella dysenteriae, Escherichia coli strain O157:H7, Vibrio cholerae, Cryptosporidium parvum; and Category C agents such as nipah virus, hantaviruses, tickbome hemorrhagic fever viruses, tickbome encephalitis viruses, yellow fever, and multidrug-resistant tuberculosis.

In preferred embodiments, the system can be used to deliver inactivated antigenic toxins, such as anatoxin antigens, including toxoids (inactivated but antigenic toxins), and toxoid conjugates. In preferred embodiments, the toxoid is an inactivated microbial toxin. In other embodiments, the toxoid is an inactivated plant toxin. In further embodiments, the toxoid is an inactivated animal toxin. In certain embodiments, the system can be used to deliver toxoids such as pertussis toxoid, Corynebacterium diphtheriae toxoid, tetanus toxoid, Haemophilus influenzae type b-tetanus toxoid conjugate, Clostridium botulinum D toxoid, Clostridium botulinum E toxoid, toxoid produced from Toxin A of Clostridium difficile, Vibrio cholerae toxoid, Clostridium perfringens Types C and D toxoid, Clostridium chauvoei toxoid, Clostridium novyi (Type B) toxoid, Clostridium septicum toxoid, recombinant HIV tat IIIB toxoid, Staphylococcus toxoid, Actinobacillus pleuropneumoniae Apx I toxoid, Actinobacillus pleuropneumoniae Apx II toxoid, Actinobacillus pleuropneumoniae Apx III toxoid, Actinobacillus pleuropneumoniae outer membrane protein (OMP) toxoid, Pseudomonas aeruginosa elastase toxoid, snake venom toxoid, ricin toxoid, Mannheimia haemolytica toxoid, Pasteurella multocida toxoid, Salmonella typhimurium toxoid, Pasteurella multocida toxoid, and Bordetella bronchiseptica toxoid.

Techniques of making a toxoid from a corresponding toxin, e.g., chemical treatment with formaldehyde or aluminum salts or gamma irradiation, are known in the art. Recombinant methods of converting a toxin to a toxoid are also known (Fromen-Romano, C., et al., Transformation of a non-enzymatic toxin into a toxoid by genetic engineering, Protein Engineering vol. 10 no. 10 pp. 1213-1220, 1997). In preferred embodiments, the system of the present invention can be used to deliver a recombinant toxoid. In other preferred embodiments, the system of the present invention can be used to deliver an expression vector encoding a recombinant toxoid.

In order to produce a genetic vaccine to protect against pathogen infection, genetic material which encodes immunogenic proteins against which a protective immune response can be mounted, must be included in the nucleic acid composition. Whether the pathogen infects intracellularly, for which the present invention is particularly useful, or extracellularly, it is unlikely that all pathogen antigens will elicit a protective response. Because DNA and RNA are both relatively small and can be produced relatively easily, the present invention provides the additional advantage of allowing for vaccination with multiple pathogen antigens. The nucleic acid composition used in the genetic vaccine can include genetic material that encodes many pathogen antigens. For example, several viral genes may be included in a single construct, thereby providing multiple targets. In addition, multiple inoculants which can be delivered to different cells in an individual can be prepared to collectively include, in some cases, a complete or, more preferably, an incomplete, e.g., nearly complete set of genes in the vaccine. For example, a complete set of viral genes may be administered using two constructs which each contain a different half of the genome which are administered at different sites. Thus, an immune response may be invoked against each antigen without the risk of an infectious virus being assembled. This allows for the introduction of more than a single antigen target and can eliminate the requirement that protective antigens be identified.

In accordance with the present invention there is also provided a method of conferring a broad based protective immune response against hyperproliferating cells that are characteristic of hyperproliferative diseases, as well as a method of treating individuals suffering from hyperproliferative diseases. As used herein, the term "hyperproliferative diseases" is meant to refer to those diseases and disorders characterized by hyperproliferation of cells. Examples of hyperproliferative diseases include all forms of cancer and psoriasis.

It has been discovered that introduction of a nucleic acid composition that includes a nucleotide sequence which encodes an immunogenic "hyperproliferating cell"-associated protein into the cells of an individual, results in the production of those proteins in the vaccinated cells of an individual. As used herein, the term "hyperproliferative-associated protein" is meant to refer to proteins that are associated with a hyperproliferative disease. To immunize against hyperproliferative diseases, a nucleic acid composition that includes a nucleotide sequence which encodes a protein that is associated with a hyperproliferative disease is administered to an individual.

In order for the hyperproliferative-associated protein to be an effective immunogenic target, it must be a protein that is produced exclusively or at higher levels in hyperproliferative cells as compared to normal cells. Target antigens include such proteins, fragments thereof and peptides which comprise at least an epitope found on such proteins. In some cases, a hyperproliferative-associated protein is the product of a mutation of a gene that encodes a protein. The mutated gene encodes a protein which is nearly identical to the normal protein except it has a slightly different amino acid sequence which results in a different epitope not found on the normal protein. Such target proteins include those which are proteins encoded by oncogenes such as myb, myc, fyn, and the translocation genes bcr/abl, ras, src, P53, neu, trk and EGRF. In addition to oncogene products as target antigens, target proteins for anti-cancer treatments and protective regimens include variable regions of antibodies made by B cell lymphomas, and variable regions of T cell receptors of T cell lymphomas which, in some embodiments, are also used as target antigens for autoimmune diseases. Other tumor-associated proteins can be used as target proteins, such as proteins which are found at higher levels in tumor cells, including the protein recognized by monoclonal antibody 17-1A and folate binding proteins.

While the present invention may be used to immunize an individual against one or more of several forms of cancer, the present invention is particularly useful to prophylactically immunize an individual who is predisposed to develop a particular cancer or who has had cancer and is therefore susceptible to a relapse. Developments in genetics and biotechnology, as well as epidemiology, allow for the determination of probability and risk assessment for the development of cancer in an individual. Using genetic screening and/or family health histories, it is possible to predict the probability that a particular individual has for developing any one of several types of cancer.

Similarly, those individuals who have already developed cancer and who have been treated to remove the cancer, or are otherwise in remission, are particularly susceptible to relapse and reoccurrence. As part of a treatment regimen, such individuals can be immunized against the cancer that they have been diagnosed as having had in order to combat such a recurrence. Thus, once it is known that individuals have had a type of cancer and are at risk of a relapse, they can be immunized in order to prepare their immune systems to combat any future appearance of the cancer.

The present invention also provides a method of treating individuals suffering from hyperproliferative diseases. In such methods, the introduction of peptide, protein, carbohydrate or nucleic acid compositions and combinations thereof serves as an immunotherapeutic, directing and promoting the immune system of the individual to combat hyperproliferative cells that produce the target protein.

The present invention provides a method of treating individuals suffering from autoimmune diseases and disorders by conferring a broad based protective immune response against targets that are associated with autoimmunity, including cell receptors and cells which produce "self"-directed antibodies.

T cell mediated autoimmune diseases include Rheumatoid arthritis (RA), multiple sclerosis (MS), Sjogren's syndrome, sarcoidosis, insulin dependent diabetes mellitus (IDDM), autoimmune thyroiditis, reactive arthritis, ankylosing spondylitis, scleroderma, polymyositis, dermatomyositis, psoriasis, vasculitis, Wegener's granulomatosis, Crohn's disease and ulcerative colitis. Each of these diseases is characterized by T cell receptors that bind to endogenous antigens and initiate the inflammatory cascade associated with autoimmune diseases. Vaccination against the variable region of the T cells would elicit an immune response including CTLs to eliminate those T cells.

In RA, several specific variable regions of T cell receptors (TCRs) which are involved in the disease have been characterized. These TCRs include $V\beta$-3, $V\beta$-14, $V\beta$-17 and $V\alpha$-17. Thus, vaccination with a composition composed of peptide, protein, carbohydrate or nucleic acid compositions and combinations thereof that delivers or encodes at least one of these proteins will elicit an immune response that will target T cells involved in RA. See: Howell, M. D., et al., 1991 Proc. Natl. Acad. Sci. USA 88:10921-10925; Paliard, X., et al., 1991 Science 253:325-329; Williams, W. V., et al., 1992 J. Clin. Invest. 90:326-333; each of which is incorporated herein by reference.

In MS, several specific variable regions of TCRs which are involved in the disease have been characterized. These TCRs include $V\beta$-7 and $V\alpha$-10. Thus, vaccination with a composition composed of peptide, protein, carbohydrate or nucleic acid compositions and combinations thereof that delivers or encodes at least one of these proteins will elicit an immune response that will target T cells involved in MS. See: Wucherpfennig, K. W., et al., 1990 Science 248:1016-1019; Oksenberg, J. R., et al., 1990 Nature 345:344-346; each of which is incorporated herein by reference.

In scleroderma, several specific variable regions of TCRs which are involved in the disease have been characterized. These TCRs include $V\beta$-6, $V\beta$-8, $V\beta$-14 and $V\alpha$-16, $V\alpha$-3C, $V\alpha$-7, $V\alpha$-14, $V\alpha$-15, $V\alpha$-16, $V\alpha$-28 and $V\alpha$-12. Thus, vaccination with a composition composed of peptide, protein, carbohydrate or nucleic acid compositions and combinations thereof that delivers or encodes for at least one of these proteins will elicit an immune response that will target T cells involved in scleroderma.

In order to treat subjects suffering from a T cell mediated autoimmune disease, particularly those for which the variable region of the TCR has yet to be characterized, a synovial biopsy can be performed. Samples of the T cells present can be taken and the variable region of those TCRs identified using standard techniques. Vaccines can be prepared using this information.

B cell mediated autoimmune diseases include Lupus (SLE), Grave's disease, myasthenia gravis, autoimmune hemolytic anemia, autoimmune thrombocytopenia, asthma, cryoglobulinemia, primary biliary sclerosis and pernicious anemia. Each of these diseases is characterized by antibodies which bind to endogenous antigens and initiate the inflammatory cascade associated with autoimmune diseases. Vaccination against the variable region of such antibodies would elicit an immune response including CTLs to eliminate those B cells that produce the antibody.

In order to treat subjects suffering from a B cell mediated autoimmune disease, the variable region of the antibodies involved in the autoimmune activity must be identified. A biopsy can be performed and samples of the antibodies present at a site of inflammation can be taken. The variable region of those antibodies can be identified using standard techniques. Vaccines can be prepared using this information.

In the case of SLE, one antigen is believed to be DNA. Thus, in subjects to be immunized against SLE, their sera can be screened for anti-DNA antibodies and a vaccine can be prepared which includes nucleic acid compositions that encode the variable region of such anti-DNA antibodies found in the sera.

Common structural features among the variable regions of both TCRs and antibodies are well known. The DNA sequence encoding a particular TCR or antibody can generally be found following well known methods such as those described in Kabat, et al. 1987 Sequence of Proteins of Immunological Interest U.S. Department of Health and Human Services, Bethesda Md., which is incorporated herein by reference. In addition, a general method for cloning functional variable regions from antibodies can be found in Chaudhary, V. K., et al., 1990 Proc. Natl. Acad. Sci. USA 87:1066, which is incorporated herein by reference.

Gene Therapy

In preferred embodiments, the present invention provides compositions and methods for the treatment of genetic disorders or conditions having a genetic component. In further preferred embodiments, the present invention provides compositions useful for the manufacture of pharmaceutical products for the treatment of genetic disorders or conditions having a genetic component.

The Human Genome Project has increased our knowledge of the genetic basis of disease. See, generally, http://www.oml.gov/sci/techresources/Human_Genome/medicine/assist.shtml.

Both environmental and genetic factors have roles in the development of any disease. A genetic disorder is a disease caused by abnormalities in an individual's genetic material (genome). There are four different types of genetic disorders: (1) single-gene, (2) multifactorial, (3) chromosomal, and (4) mitochondrial.

(1) Single-gene (also called Mendelian or monogenic)—This type is caused by changes or mutations that occur in the DNA sequence of one gene. Genes code for proteins, the molecules that carry out most of the work, perform most life functions, and even make up the majority of cellular structures. When a gene is mutated so that its protein product can no longer carry out its normal function, a disorder can result. There are more than 6,000 known single-gene disorders, which occur in about 1 out of every 200 births. Some examples are cystic fibrosis, sickle cell anemia, Marfan syndrome, Huntington's disease, and hereditary hemochromatosis.

(2) Multifactorial (also called complex or polygenic)—This type is caused by a combination of environmental factors and mutations in multiple genes. For example, different genes that influence breast cancer susceptibility have been found on chromosomes 6, 11, 13, 14, 15, 17, and 22. Its more complicated nature makes it much more difficult to analyze than single-gene or chromosomal disorders. Some of the most common chronic disorders are multifactorial disorders. Examples include heart disease, high blood pressure, Alzheimer's disease, arthritis, diabetes, cancer, and obesity. Multifactorial inheritance also is associated with heritable traits such as fingerprint patterns, height, eye color, and skin color.

(3) Chromosomal—Chromosomes, distinct structures made up of DNA and protein, are located in the nucleus of each cell. Because chromosomes are carriers of genetic material, such abnormalities in chromosome structure as missing or extra copies or gross breaks and rejoinings (translocations), can result in disease. Some types of major chromosomal abnormalities can be detected by microscopic examination. Down syndrome or trisomy 21 is a common disorder that occurs when a person has three copies of chromosome 21.

(4) Mitochondrial—This relatively rare type of genetic disorder is caused by mutations in the nonchromosomal DNA of mitochondria. Mitochondria are small round or rod-like organelles that are involved in cellular respiration and found in the cytoplasm of plant and animal cells. Each mitochondrion may contain 5 to 10 circular pieces of DNA.

In preferred embodiments, the particulate delivery system of the present invention is used to administer at least one nucleic acid comprising a compensating gene. In other preferred embodiments, the particulate delivery system of the present invention is used to administer at least one nucleic acid encoding a gene product of a missing gene, wherein the expression of the gene product is useful in the treatment of the genetic disorder or the genetic component of a condition. In preferred embodiments, the particulate delivery system of the present invention including the desired payload molecule is useful for the manufacture of a pharmaceutical product for the treatment of genetic disorder or the genetic component of a condition. Such pharmaceutical products are suitably administered orally, rectally, parenterally, (for example, intravenously, intramuscularly, or subcutaneously) intracistemally, intravaginally, intraperitoneally, intravesically, locally (for example, powders, ointments or drops), or as a buccal or nasal spray. The pharmaceutical products are preferably administered orally, buccally, and parenterally, more preferably orally. Particles loaded with different payloads, e.g., a nucleic acid, a nucleic acid expression vector or a small molecule therapeutic can be mixed in the appropriate proportions and administered together, e.g., in a capsule, for combination therapy.

In aspects of the present invention that relate to gene therapy, the nucleic acid compositions contain either compensating genes or genes that encode therapeutic proteins. Examples of compensating genes include a gene that encodes dystrophin or a functional fragment, a gene to compensate for the defective gene in subjects suffering from cystic fibrosis, a gene to compensate for the defective gene in subjects suffering from ADA, and a gene encoding Factor VIII. Examples of genes encoding therapeutic proteins include genes which encodes erythropoietin, interferon, LDL receptor, GM-CSF, IL-2, IL-4 and TNF. Additionally, nucleic acid compositions which encode single chain antibody components which specifically bind to toxic substances can be administered. In some preferred embodiments, the dystrophin gene is provided as part of a mini-gene and used to treat individuals suffering from muscular dystrophy. In some preferred embodiments, a mini-gene which contains coding sequence for a partial dystrophin protein is provided. Dystrophin abnormalities are responsible for both the milder Becker's Muscular Dystrophy (BMD) and the severe Duchenne's Muscular Dystrophy (DMD). In BMD dystrophin is made, but it is abnormal in either size and/or amount. The subject is mild to moderately weak. In DMD no protein is made and the subject is wheelchair-bound by age 13 and usually dies by age 20. In some subjects, particularly those suffering from BMD, partial dystrophin protein produced by expression of a mini-gene delivered according to the present invention can provide improved muscle function.

In preferred embodiments, the particulate delivery system of the present invention provides compositions and methods for the treatment of genetic disorders and conditions believed to have a genetic component, such as Aarskog-Scott syndrome, Aase syndrome, achondroplasia, acrodysostosis, addiction, adreno-leukodystrophy, albinism, ablepharon-macrostomia syndrome, alagille syndrome, alkaptonuria, alpha-I antitrypsin deficiency, Alport's syndrome, Alzheimer's disease, asthma, autoimmune polyglandular syndrome, androgen insensitivity syndrome, Angelman syndrome, ataxia, ataxia telangiectasia, atherosclerosis, attention deficit hyperactivity disorder (ADHD), autism, baldness, Batten disease, Beckwith-Wiedemann syndrome, Best disease, bipolar disorder, brachydactyly, breast cancer, Burkitt lymphoma, chronic myeloid leukemia, Charcot-Marie-Tooth disease, Crohn's disease, cleft lip, Cockayne syndrome, Coffin Lowry Syndrome, colon cancer, congenital adrenal hyperplasia (CAH), Comelia de Lange Syndrome, Costello Syndrome, Cowden Syndrome, Craniofrontonasal Dysplasia, Crigler-Najjar Syndrome, Creutzfeldt-Jakob Disease (CJD), cystic fibrosis, deafness, depression, diabetes, diastrophic dysplasia, DiGeorge Syndrome, Down's Syndrome, dyslexia, Duchenne muscular dystrophy, Dubowitz Syndrome, ectodermal dysplasia, Ellis-van Creveld syndrome, Ehlers-Danlos, Epidermolysis Bullosa (EB), epilepsy, essential tremor, familial hypercholesterolemia, familial Mediterranean fever, Fragile X Syndrome, Friedreich's ataxia, Gaucher disease, glaucoma, glucose galactose malabsorption, glutaricaciduria, gyrate atrophy, Goldberg Shprintzen Syndrome (velocardiofacial syndrome), Gorlin Syndrome, Hailey-Hailey Disease, hemihypertrophy, hemochromatosis, hemophilia, hereditary motor and sensory neuropathy (HMSN), hereditary non polyposis colorectal cancer (HNPCC), Huntington's disease, immunodeficiency with hyper-IgM, juvenile onset diabetes, Klinefelter's Syndrome, Kabuki Syndrome, Leigh's Disease (or Syndrome), Long QT Syndrome, lung cancer, malignant melanoma, manic depression, Marfan Syndrome, Menkes syndrome, miscarriage, mucopolysaccharide disease, multiple endocrine neoplasia, multiple sclerosis, muscular dystrophy, myotrophic lateral sclerosis, myotonic dystrophy, neurofibromatosis, Niemann-Pick disease, Noonan Syndrome, obesity, ovarian cancer, p53 tumor suppressor, pancreatic cancer, Parkinson disease, paroxysmal nocturnal hemoglobinuria, Pendred syndrome, peroneal muscular atrophy, phenylketonuria (PKU), polycystic kidney disease, Prader-Willi Syndrome, primary biliary cirrhosis, prostate cancer, REAR Syndrome, Refsum disease, retinitis pigmentosa, retinoblastoma, Rett Syndrome, Sanfilippo Syndrome, schizophrenia, severe combined immunodeficiency, sickle cell anemia, spina bifida, spinal muscular atrophy, spinocerebellar atrophy, SRY: sex determination, Sudden Adult Death Syndrome, Tangier disease, Tay-Sachs disease, thrombocytopenia absent radius syndrome, Townes-Brocks Syndrome, tuberous sclerosis, Turner syndrome, Usher syndrome, von Hippel-Lindau syndrome, Waardenburg syndrome, Weaver syndrome, Werner syndrome, Williams syndrome, Wilson's Disease, xeroderma pigmentosum and Zellweger syndrome.

In other preferred embodiments, the particulate delivery system of the present invention provides compositions and methods for the treatment of genetic disorders and conditions believed to have a genetic component that are manifested as metabolic disorders, such as protein-related disorders, including Sickle-Cell Anemia and beta-Thalassemias, alpha-Thalassemias, Marfan's Syndrome, Ehlers-Danlos Type I, Ehlers-Danlos Type II, Ehlers-Danlos Type III, Ehlers-Danlos Type IV autosomal dominant, Ehlers-Danlos Type IV autosomal recessive, Ehlers-Danlos Type IV-D, Ehlers-Danlos Type V, Ehlers-Danlos Type VI, Ehlers-Danlos Type VII autosomal dominant, Ehlers-Danlos Type VII autosomal recessive, Ehlers-Danlos Type VIII. Ehlers-Danlos with Platelet Dysfunction, Cutis Laxa, Cutis Laxa recessive Type I, Occipital Horn Syndrome Cutis Laxa, X-linked, Osteogenesis Imperfecta Type I, Osteogenesis Imperfecta Type I-C, Osteogenesis Imperfecta Silent Type II/III, Osteogenesis Imperfecta Type IV, Osteogenesis Imperfecta Neonatal Lethal form, and Osteogenesis Imperfecta progressively deforming.

In further preferred embodiments, the particulate delivery system of the present invention provides compositions and methods for the treatment of genetic disorders of the clotting system, such as afibrinogenemia, complete loss of fibrinogen, Factor I; dysfibrinogenemia dysfunctional fibrinogen, Factor I; Factor II disorders; tissue factor deficiency; Factor V deficiency, labile Factor deficiency, Factor VII deficiency, Factor VIII deficiency (Hemophilia A), Factor IX deficiency (Hemophilia B), Factor X deficiency, Factor XI deficiency, Rosenthal Syndrome, Plasma Thromboplastin Antecedent (PTA) deficiency, Factor XII deficiency, Hageman factor deficiency, Factor XIII deficiency, Factor V & VIII Combined deficiency, Factor VIII & IX combined deficiency, Factor IX & XI Combined deficiency, Protein C deficiency, Protein S deficiency, thrombophilia, antithrombin III deficiency, giant platelet syndrome, platelet glycoprotein Ib deficiency, von Willebrand disease, Fletcher Factor deficiency and prekallikrein deficiency.

In further preferred embodiments, the particulate delivery system of the present invention provides compositions and methods for the treatment of glycogen storage disorders, such as Type 0, Type I (von Gierke's disease), Type Ib, Type Ic, Type II (Pompe disease), Type IIb (Danon disease), Type III (Cori disease or Forbes disease), Type IV (Andersen disease), Type V (McArdle disease), Type VI (Hers disease), Type VII (Tarui disease), Type VIII, Type IX, and Type XI (Fanconi-Bickel syndrome).

In yet further preferred embodiments, the particulate delivery system of the present invention provides compositions and methods for the treatment of defects in fructose, galactose and glycerol metabolism, such as hereditary fructose intolerance, aldolase B deficiency; fructosuria, hepatic fructokinase deficiency; classic galactosemia, galactose epimerase deficiency; galactokinase deficiency; hyperglycerolemia and glycerol kinase deficiency.

In yet further preferred embodiments, the particulate delivery system of the present invention provides compositions and methods for the treatment of defects in cholesterol and lipoprotein metabolism, such as apolipoprotein(a)—Lp(a), hyperlipoproteinemia Type I; hyperlipoproteinemia Type Ib; apolipoprotein C-II deficiency; hyperlipoproteinemia Type Ic, chylomicronemia; familial hypercholesterolemia, Type II hyperlipoproteinemia; hyperlipoproteinemia Type II, familial hyperbetalipoproteinemia; hyperlipoproteinemia Type III, apolipoprotein E deficiency; hyperlipoproteinemia Type IV; hyperlipoproteinemia Type V; familial LCAT deficiency; Wolman disease; lipoprotein lipase deficiency; familial hypertriglyceridemia; hyperlipidemia Type V; hyperlipidemia Type VI; familial ligand-defective apo-B; familial hyperalphalipoproteinemia; hypobetalipoproteinemia, apolipoprotein B-100 deficiency; abetalipoproteinemia, Kornzweig syndrome; and Tangier Disease, familial high-density lipoprotein deficiency.

In yet further preferred embodiments, the particulate delivery system of the present invention provides compositions and methods for the treatment of mucopolysaccharide and glycolipid disorders, such as Type I H mucopolysaccharidosis (Hurler syndrome), Type I S mucopolysaccharidosis (Scheie syndrome), Type I H/S mucopolysaccharidosis (Hurler/Scheie syndrome), Type II mucopolysaccharidosis (Hunter's syndrome), Type III mucopolysaccharidoses (Sanfilippo Type A, Sanfilippo Type B, Sanfilippo Type C, Sanfilippo Type D), Type IV mucopolysaccharidosis (Morquio's Type A, Morquio's Type B), Type VI mucopolysaccharidosis (Maroteaux-Lamy Syndrome) and Type VII mucopolysaccharidosis (Sly Syndrome).

In other preferred embodiments, the particulate delivery system of the present invention provides compositions and methods for the treatment of disorders of glycosphingolipid metabolism, such as GM1 gangliosidoses, including generalized GM1 Type II, juvenile form; generalized GM1 Type III, adult form; GM2 gangliosidosis, Sandhoff-Jatzkewitz disease; GM3 gangliosidoses, Tay-Sachs disease, Tay-Sachs AB variant, Gaucher disease, Niemann-Pick Disease, Types A, B, C1, C2 and D, Schindler disease, Fabry disease, lactosylceramidosis, Farber disease, Krabbe disease, multiple sulfatase deficiency, Austin disease, metachromic leukodystrophy, and sulfatide lipodosis.

In other preferred embodiments, the particulate delivery system of the present invention provides compositions and methods for the treatment of oligosaccharidoses such as fucosidosis, mucolipodosis VI, sialolipidosis, alpha-mannosidosis, beta-mannosidosis, sialidoses Types I and II, galactosialidosis, Goldberg syndrome and aspartylglucosaminuria.

In other preferred embodiments, the particulate delivery system of the present invention provides compositions and methods for the treatment of disorders of lysosomal enzyme transport such as mucolipidosis I, sialidosis; mucolipodosis II, I-cell disease; and mucolipodosis III, pseudo-Hurler polydystrophy.

In other preferred embodiments, the particulate delivery system of the present invention provides compositions and methods for the treatment of defects in amino acid and organic acid metabolism such as phenylketonuria; Type I tyrosinemia, tyrosinosis; Type II tyrosinemia, Richner-Hanhart syndrome; Type III tyrosinemia; alcaptonuria; homocystinuria; histidinemia; maple syrup urine disease (MSUD); MSUD Type Ib, MSUD type II; methylmalonic aciduria; non-ketonic hyperglycinemia Type I (NKHI) and hyperlysinemia.

In other preferred embodiments, the particulate delivery system of the present invention provides compositions and methods for the treatment of urea cycle defects such as hyperammonemias; carbamoyl phosphate synthetase I (CPS-I) deficiency; ornithine transcarbamylase (OTC) deficiency; N-acetylglutamate synthetase deficiency; argininosuccinic aciduria, argininosuccinate lyase deficiency; hyperargininemia, arginase deficiency; citrullinemia, argininosuccinate synthetase deficiency and ornithine aminotransferase deficiency. In other preferred embodiments, the particulate delivery system of the present invention provides compositions and methods for the treatment of defects in amino acid transport such as cystinuria Type I; cystinuria Type III; Hartnup disease and hyperammonemia-hyperomithinemia-homocitrullinuria (HHH) syndrome. In other preferred embodiments, the particulate delivery system of the present invention provides compositions and methods for the treatment of porphyrias and bilirubinemias such as congenital erythropoietic porphyria (CEP); erythropoietic protoporphyria (EPP); ALA dehydratase deficiency porphyria (ADP); acute intermittent porphyria (AIP); hereditary coproporphyria (HCP); variegate porphyria (VP); porphyria cutanea tarda (PCT); hepatoerythropoietic porphyria (HEP); Gilbert Syndrome; Crigler-Najjar Syndrome, Types I and I; Dubin-Johnson syndrome and Rotor syndrome.

In other preferred embodiments, the particulate delivery system of the present invention provides compositions and methods for the treatment of errors in fatty acid metabolism such as very-long-chain acyl-CoA dehydrogenase deficiency (VLCAD); long-chain acyl-CoA dehydrogenase deficiency (LCAD); medium-chain acyl-CoA dehydrogenase deficiency (MCAD); short-chain acyl-CoA dehydrogenase deficiency (SCAD; carnitine translocase deficiency; carnitine palmitoyltransferase I (CPT I) deficiency and carnitine palmitoyltransferase II (CPT II) deficiency. In other preferred embodiments, the particulate delivery system of the present invention provides compositions and methods for the treatment of defects in nucleotide metabolism such as Lesch-Nyhan syndrome; Severe Combined Immunodeficiency Disease (SCID), due to adenosine deaminase (ADA) deficiency; gout; renal lithiasis, due to adenine phosphoribosyltransferase (APRT) deficiency; xanthinuria, due to xanthine oxidase deficiency; orotic aciduria, Types I & I and ornithine transcarbamoylase deficiency.

In other preferred embodiments, the particulate delivery system of the present invention provides compositions and methods for the treatment of disorders in metal metabolism and transport such as Wilson disease, Menkes disease, occipital horn syndrome and hemochromatosis. In other preferred embodiments, the particulate delivery system of the present invention provides compositions and methods for the treatment of disorders in peroxisomes such as Zellweger syndrome, X-linked adreoleukodystrophy, neonatal adrenoleukodystophy (NALD), rhizomelic chondrodysplasia punctata (RCDP) and infantile Refsum's disease (IRD). In other preferred embodiments, the particulate delivery system of the present invention provides compositions and methods for the treatment of disorders associated with defective DNA repair such as ataxia telangiectasia (AT), xeroderma pigmentosum (XP), Cockayne syndrome, Bloom syndrome and Fanconi anemia.

Routes of Administration

Routes of administration include but are not limited to oral; buccal, sublingual, pulmonary, transdermal, transmucosal, as well as subcutaneous, intraperitoneal, intravenous, and intramuscular injection. Preferred routes of administration are oral; buccal, sublingual, pulmonary and transmucosal.

The particulate delivery system of the present invention is administered to a subject in a therapeutically effective amount. The particulate delivery system can be administered alone or as part of a pharmaceutically acceptable composition. In addition, a compound or composition can be administered all at once, as for example, by a bolus injection, multiple times, such as by a series of tablets, or delivered substantially uniformly over a period of time, as for example, using a controlled release formulation. It is also noted that the dose of the compound can be varied over time. The particulate delivery system can be administered using an immediate release formulation, a controlled release formulation, or combinations thereof. The term "controlled release" includes sustained release, delayed release, and combinations thereof.

A pharmaceutical composition of the invention can be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient that would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the human treated and further depending upon the route by which the composition is to be administered. By way of example, the composition can comprise between 0.1% and 100% (w/w) active ingredient. A unit dose of a pharmaceutical composition of the invention will generally comprise from about 100 milligrams to about 2 grams of the active ingredient, and preferably comprises from about 200 milligrams to about 1.0 gram of the active ingredient.

In addition, a particulate delivery system of the present invention can be administered alone, in combination with a particulate delivery system with a different payload, or with other pharmaceutically active compounds. The other pharmaceutically active compounds can be selected to treat the same condition as the particulate delivery system or a different condition.

If the subject is to receive or is receiving multiple pharmaceutically active compounds, the compounds can be administered simultaneously or sequentially in any order. For example, in the case of tablets, the active compounds may be found in one tablet or in separate tablets, which can be administered at once or sequentially in any order. In addition, it should be recognized that the compositions can be different forms. For example, one or more compounds may be delivered via a tablet, while another is administered via injection or orally as a syrup.

Another aspect of the invention relates to a kit comprising a pharmaceutical composition of the invention and instructional material. Instructional material includes a publication, a recording, a diagram, or any other medium of expression which is used to communicate the usefulness of the pharmaceutical composition of the invention for one of the purposes set forth herein in a human. The instructional material can also, for example, describe an appropriate dose of the pharmaceutical composition of the invention. The instructional material of the kit of the invention can, for example, be affixed to a container which contains a pharmaceutical composition of the invention or be shipped together with a container which contains the pharmaceutical composition. Alternatively, the instructional material can be shipped separately from the container with the intention that the instructional material and the pharmaceutical composition be used cooperatively by the recipient.

The invention also includes a kit comprising a pharmaceutical composition of the invention and a delivery device for delivering the composition to a human. By way of example, the delivery device can be a squeezable spray bottle, a metered-dose spray bottle, an aerosol spray device, an atomizer, a dry powder delivery device, a self-propelling solvent/powder-dispensing device, a syringe, a needle, a tampon, or a dosage-measuring container. The kit can further comprise an instructional material as described herein.

For example, a kit may comprise two separate pharmaceutical compositions comprising respectively a first composition comprising a particulate delivery system and a pharmaceutically acceptable carrier; and composition comprising second pharmaceutically active compound and a pharmaceutically acceptable carrier. The kit also comprises a container for the separate compositions, such as a divided bottle or a divided foil packet. Additional examples of containers include syringes, boxes, bags, and the like. Typically, a kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

An example of a kit is a blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and a sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen that the tablets or capsules so specified should be ingested. Another example of such a memory aid is a calendar printed on the card, e.g., as follows "First Week, Monday, Tuesday, . . . etc. . . . Second Week, Monday, Tuesday," etc. Other variations of memory aids will be readily apparent. A "daily dose" can be a single tablet or capsule or several pills or capsules to be taken on a given day. Also, a daily dose of a particulate delivery system composition can consist of one tablet or capsule, while a daily dose of the second compound can consist of several tablets or capsules and vice versa. The memory aid should reflect this and assist in correct administration.

In another embodiment of the present invention, a dispenser designed to dispense the daily doses one at a time in the order of their intended use is provided. Preferably, the dispenser is equipped with a memory aid, so as to further facilitate compliance with the dosage regimen. An example of such a memory aid is a mechanical counter, which indicates the number of daily doses that have been dispensed. Another example of such a memory aid is a battery-powered microchip memory coupled with a liquid crystal readout, or audible reminder signal which, for example, reads out the date that the last daily dose has been taken and/or reminds one when the next dose is to be taken.

A particulate delivery system composition, optionally comprising other pharmaceutically active compounds, can be administered to a subject either orally, rectally, parenterally, (for example, intravenously, intramuscularly, or subcutaneously) intracisternally, intravaginally, intraperitoneally, intravesically, locally (for example, powders, ointments or drops), or as a buccal or nasal spray.

Parenteral administration of a pharmaceutical composition includes any route of administration characterized by physical breaching of a tissue of a human and administration of the pharmaceutical composition through the breach in the tissue. Parenteral administration thus includes administration of a pharmaceutical composition by injection of the composition, by application of the composition through a surgical incision, by application of the composition through a tissue-penetrating non-surgical wound, and the like. In particular, parenteral administration includes subcutaneous, intraperitoneal, intravenous, intraarterial, intramuscular, or intrasternal injection and intravenous, intraarterial, or kidney dialytic infusion techniques.

Compositions suitable for parenteral injection comprise the active ingredient combined with a pharmaceutically acceptable carrier such as physiologically acceptable sterile aqueous or nonaqueous solutions, dispersions, suspensions, or emulsions, or may comprise sterile powders for reconstitution into sterile injectable solutions or dispersions. Examples of suitable aqueous and nonaqueous carriers, diluents, solvents, or vehicles include water, isotonic saline, ethanol, polyols (propylene glycol, polyethylene glycol, glycerol, and the like), suitable mixtures thereof, triglycerides, including vegetable oils such as olive oil, or injectable organic esters such as ethyl oleate. Proper fluidity can be maintained, for example, by the use of a coating such as lecithin, by the maintenance of the required particle size in the case of dispersions, and/or by the use of surfactants. Such formulations can be prepared, packaged, or sold in a form suitable for bolus administration or for continuous administration. Injectable formulations can be prepared, packaged, or sold in unit dosage form, such as in ampules, in multi-dose containers containing a preservative, or in single-use devices for auto-injection or injection by a medical practitioner.

Formulations for parenteral administration include suspensions, solutions, emulsions in oily or aqueous vehicles, pastes, and implantable sustained-release or biodegradable formulations. Such formulations can further comprise one or more additional ingredients including suspending, stabilizing, or dispersing agents. In one embodiment of a formulation for parenteral administration, the active ingredient is provided in dry (i.e. powder or granular) form for reconstitution with a suitable vehicle (e.g., sterile pyrogen-free water) prior to parenteral administration of the reconstituted composition. The pharmaceutical compositions can be prepared, packaged, or sold in the form of a sterile injectable aqueous or oily suspension or solution. This suspension or solution can be formulated according to the known art, and can comprise, in addition to the active ingredient, additional ingredients such as the dispersing agents, wetting agents, or suspending agents described herein. Such sterile injectable formulations can be prepared using a non-toxic parenterally-acceptable diluent or solvent, such as water or 1,3-butanediol, for example. Other acceptable diluents and solvents include Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer system. Compositions for sustained release or implantation can comprise pharmaceutically acceptable polymeric or hydrophobic materials such as an emulsion, an ion exchange resin, a sparingly soluble polymer, or a sparingly soluble salt.

These compositions may also contain adjuvants such as preserving, wetting, emulsifying, and/or dispersing agents. Prevention of microorganism contamination of the compositions can be accomplished by the addition of various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents capable of delaying absorption, for example, aluminum monostearate and/or gelatin.

Dosage forms can include solid or injectable implants or depots. In preferred embodiments, the implant comprises an aliquot of the particulate delivery system and a biodegradable polymer. In preferred embodiments, a suitable biodegradable polymer can be selected from the group consisting of a polyaspartate, polyglutamate, poly(L-lactide), a poly(D,L-lactide), a poly(lactide-co-glycolide), a poly($\epsilon$-caprolactone), a polyanhydride, a poly(beta-hydroxy butyrate), a poly(ortho ester) and a polyphosphazene.

Solid dosage forms for oral administration include capsules, tablets, powders, and granules. In such solid dosage forms, the particulate delivery system is optionally admixed with at least one inert customary excipient (or carrier) such as sodium citrate or dicalcium phosphate or (a) fillers or extenders, as for example, starches, lactose, sucrose, mannitol, or silicic acid; (b) binders, as for example, carboxymethylcellulose, alginates, gelatin, polyvinylpyrrolidone, sucrose, or acacia; (c) humectants, as for example, glycerol; (d) disintegrating agents, as for example, agar-agar, calcium carbonate, potato or tapioca starch, alginic acid, certain complex silicates, or sodium carbonate; (e) solution retarders, as for example, paraffin; (f) absorption accelerators, as for example, quaternary ammonium compounds; (g) wetting agents, as for example, cetyl alcohol or glycerol monostearate; (h) adsorbents, as for example, kaolin or bentonite; and/or (i) lubricants, as for example, talc, calcium stearate, magnesium stearate, solid polyethylene glycols, sodium lauryl sulfate, or mixtures thereof. In the case of capsules and tablets, the dosage forms may also comprise buffering agents.

A tablet comprising the particulate delivery system can, for example, be made by compressing or molding the active ingredient, optionally with one or more additional ingredients. Compressed tablets can be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets can be made by molding, in a suitable device, a mixture of the active ingredient, a pharmaceutically acceptable carrier, and at least sufficient liquid to moisten the mixture. Pharmaceutically acceptable excipients used in the manufacture of tablets include inert diluents, granulating and disintegrating agents, binding agents, and lubricating agents. Known dispersing agents include potato starch and sodium starch glycolate. Known surface active agents include sodium lauryl sulfate. Known diluents include calcium carbonate, sodium carbonate, lactose, microcrystalline cellulose, calcium phosphate, calcium hydrogen phosphate, and sodium phosphate. Known granulating and disintegrating agents include corn starch and alginic acid. Known binding agents include gelatin, acacia, pre-gelatinized maize starch, polyvinylpyrrolidone, and hydroxypropyl methylcellulose. Known lubricating agents include magnesium stearate, stearic acid, silica, and talc.

Tablets can be non-coated or they can be coated using known methods to achieve delayed disintegration in the gastrointestinal tract of a human, thereby providing sustained release and absorption of the particulate delivery system, e.g., in the region of the Peyer's patches in the small intestine. By way of example, a material such as glyceryl monostearate or glyceryl distearate can be used to coat tablets. Further by way of example, tablets can be coated using methods described in U.S. Pat. Nos. 4,256,108; 4,160,452; and 4,265,874 to form osmotically-controlled release tablets. Tablets can further comprise a sweetening agent, a flavoring agent, a coloring agent, a preservative, or some combination of these in order to provide pharmaceutically elegant and palatable preparation.

Solid dosage forms such as tablets, dragees, capsules, and granules can be prepared with coatings or shells, such as enteric coatings and others well known in the art. They may also contain opacifying agents, and can also be of such composition that they release the particulate delivery system in a delayed manner. Examples of embedding compositions that can be used are polymeric substances and waxes. The active compounds can also be in micro-encapsulated form, if appropriate, with one or more of the above-mentioned excipients.

Solid compositions of a similar type may also be used as fillers in soft or hard filled gelatin capsules using such excipients as lactose or milk sugar, as well as high molecular weight polyethylene glycols, and the like. Hard capsules comprising the particulate delivery system can be made using a physiologically degradable composition, such as gelatin. Such hard capsules comprise the particulate delivery system, and can further comprise additional ingredients including, for example, an inert solid diluent such as calcium carbonate, calcium phosphate, or kaolin. Soft gelatin capsules comprising the particulate delivery system can be made using a physiologically degradable composition, such as gelatin. Such soft capsules comprise the particulate delivery system, which can be mixed with water or an oil medium such as peanut oil, liquid paraffin, or olive oil.

Oral compositions can be made, using known technology, which specifically release orally-administered agents in the small or large intestines of a human subject. For example, formulations for delivery to the gastrointestinal system, including the colon, include enteric coated systems, based, e.g., on methacrylate copolymers such as poly(methacrylic acid, methyl methacrylate), which are only soluble at pH 6 and above, so that the polymer only begins to dissolve on entry into the small intestine. The site where such polymer formulations disintegrate is dependent on the rate of intestinal transit and the amount of polymer present. For example, a relatively thick polymer coating is used for delivery to the proximal colon (Hardy et al., 1987 Aliment. Pharmacol. Therap. 1:273-280). Polymers capable of providing site-specific colonic delivery can also be used, wherein the polymer relies on the bacterial flora of the large bowel to provide enzymatic degradation of the polymer coat and hence release of the drug. For example, azopolymers (U.S. Pat. No. 4,663, 308), glycosides (Friend et al., 1984, J. Med. Chem. 27:261- 268) and a variety of naturally available and modified polysaccharides (see PCT application PCT/GB89/00581) can be used in such formulations.

Pulsed release technology such as that described in U.S. Pat. No. 4,777,049 can also be used to administer the particulate delivery system to a specific location within the gastrointestinal tract. Such systems permit delivery at a predetermined time and can be used to deliver the particulate delivery system, optionally together with other additives that my alter the local microenvironment to promote stability and uptake, directly without relying on external conditions other than the presence of water to provide in vivo release.

Liquid dosage forms for oral administration include pharmaceutically acceptable emulsions, solutions, suspensions, syrups, and elixirs. In addition to the active compounds, the liquid dosage form may contain inert diluents commonly used in the art, such as water or other solvents, isotonic saline, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, almond oil, arachis oil, coconut oil, cottonseed oil, groundnut oil, corn germ oil, olive oil, castor oil, sesame seed oil, MIGLYOL™, glycerol, fractionated vegetable oils, mineral oils such as liquid paraffin, tetrahydrofurfuryl alcohol, polyethylene glycols, fatty acid esters of sorbitan, or mixtures of these substances, and the like. Besides such inert diluents, the composition can also include adjuvants, such as wetting agents, emulsifying and suspending agents, demulcents, preservatives, buffers, salts, sweetening, flavoring, coloring and perfuming agents. Suspensions, in addition to the active compound, may contain suspending agents, as for example, ethoxylated isostearyl alcohols, polyoxyethylene sorbitol or sorbitan esters, microcrystalline cellulose, hydrogenated edible fats, sodium alginate, polyvinylpyrrolidone, gum tragacanth, gum acacia, agar-agar, and cellulose derivatives such as sodium carboxymethylcellulose, methylcellulose, hydroxypropylmethylcellulose, aluminum metahydroxide, bentonite, or mixtures of these substances, and the like. Liquid formulations of a pharmaceutical composition of the invention that are suitable for oral administration can be prepared, packaged, and sold either in liquid form or in the form of a dry product intended for reconstitution with water or another suitable vehicle prior to use.

Known dispersing or wetting agents include naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include lecithin and acacia. Known preservatives include methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

In other embodiments, the pharmaceutical composition can be prepared as a nutraceutical, i.e., in the form of, or added to, a food (e.g., a processed item intended for direct consumption) or a foodstuff (e.g., an edible ingredient intended for incorporation into a food prior to ingestion). Examples of suitable foods include candies such as lollipops, baked goods such as crackers, breads, cookies, and snack cakes, whole, pureed, or mashed fruits and vegetables, beverages, and processed meat products. Examples of suitable foodstuffs include milled grains and sugars, spices and other seasonings, and syrups. The particulate delivery systems described herein are preferably not exposed to high cooking temperatures for extended periods of time, in order to minimize degradation of the compounds.

Compositions for rectal or vaginal administration can be prepared by mixing a particulate delivery system with suitable non-irritating excipients or carriers such as cocoa butter, polyethylene glycol or a suppository wax, which are solid at ordinary room temperature, but liquid at body temperature, and therefore, melt in the rectum or vaginal cavity and release the particulate delivery system. Such a composition can be in the form of, for example, a suppository, a retention enema preparation, and a solution for rectal or colonic irrigation. Suppository formulations can further comprise various additional ingredients including antioxidants and preservatives. Retention enema preparations or solutions for rectal or colonic irrigation can be made by combining the active ingredient with a pharmaceutically acceptable liquid carrier. As is known in the art, enema preparations can be administered using, and can be packaged within, a delivery device adapted to the rectal anatomy of a human. Enema preparations can further comprise various additional ingredients including antioxidants and preservatives.

A pharmaceutical composition of the invention can be prepared, packaged, or sold in a formulation suitable for pulmonary administration via the buccal cavity. Such compositions are conveniently in the form of dry powders for administration using a device comprising a dry powder reservoir to which a stream of propellant can be directed to disperse the powder or using a self-propelling solvent/powder-dispensing container such as a device comprising the particulate delivery system suspended in a low-boiling propellant in a sealed container. Dry powder compositions may include a solid fine powder diluent such as sugar and are conveniently provided in a unit dose form. Low boiling propellants generally include liquid propellants having a boiling point below 65 degrees F. at atmospheric pressure. Generally the propellant can constitute 50 to 99.9% (w/w) of the composition, and the active ingredient can constitute 0.1 to 20% (w/w) of the composition. The propellant can further comprise additional ingredients such as a liquid non-ionic or solid anionic surfactant or a solid diluent (preferably having a particle size of the same order as particles comprising the particulate delivery system).

Pharmaceutical compositions of the invention formulated for pulmonary delivery can also provide the active ingredient in the form of droplets of a suspension. Such formulations can be prepared, packaged, or sold as aqueous or dilute alcoholic suspensions, optionally sterile, comprising the particulate delivery system, and can conveniently be administered using any nebulization or atomization device. Such formulations can further comprise one or more additional ingredients including a flavoring agent such as saccharin sodium, a volatile oil, a buffering agent, a surface active agent, or a preservative such as methylhydroxybenzoate.

The formulations described herein as being useful for pulmonary delivery are also useful for intranasal delivery of a pharmaceutical composition of the invention. Another formulation suitable for intranasal administration is a coarse powder comprising the particulate delivery system. Such a formulation is administered in the manner in which snuff is taken i.e. by rapid inhalation through the nasal passage from a container of the powder held close to the nares.

A pharmaceutical composition of the invention can be prepared, packaged, or sold in a formulation suitable for buccal administration. Such formulations can, for example, be in the form of tablets or lozenges made using conventional methods, and can, for example, comprise 0.1 to 20% (w/w) particulate delivery system, the balance comprising an orally dissolvable or degradable composition and, optionally, one or more of the additional ingredients described herein. Alternately, formulations suitable for buccal administration can comprise a powder or an aerosolized or atomized solution or suspension comprising the particulate delivery system.

Antibodies

As used herein, the term "antibody" (Ab) or "monoclonal antibody" (Mab) is meant to include intact molecules as well as antibody fragments (such as, for example, Fab and F(ab')2 fragments) which are capable of specifically binding to protein. Fab and F(ab')2 fragments lack the Fc fragment of intact antibody, clear more rapidly from the circulation, and may have less non-specific tissue binding than an intact antibody. Thus, these fragments are preferred, as well as the products of a Fab or other immunoglobulin expression library. Moreover, antibodies of the present invention include chimeric, single chain, and humanized antibodies.

Antibodies can be prepared using any number of techniques known in the art. Suitable techniques are discussed briefly below. The antibody may be polyclonal or monoclonal. Polyclonal antibodies can have significant advantages for initial development, including rapidity of production and specificity for multiple epitopes, ensuring strong immunofluorescent staining and antigen capture. Monoclonal antibodies are adaptable to large-scale production; preferred embodiments include at least one monoclonal antibody specific for an epitope of the target antigen. Because polyclonal preparations cannot be readily reproduced for large-scale production, another embodiment uses a cocktail of at least four monoclonal antibodies.

A single chain Fv ("scFv" or "sFv") polypeptide is a covalently linked $V_H$:$V_L$ heterodimer which may be expressed from a nucleic acid including $V_H$- and $V_L$-encoding sequences either joined directly or joined by a peptide-encoding linker. Huston, et al. Proc. Nat. Acad. Sci. USA, 85: 5879-5883 (1988). A number of structures for converting the naturally aggregated, but chemically separated, light and heavy polypeptide chains from an antibody V region into a scFv molecule which folds into a three dimensional structure substantially similar to the structure of an antigen-binding site. See, e.g., U.S. Pat. Nos. 6,512,097, 5,091,513 and 5,132,405 and 4,956,778.

In one class of embodiments, recombinant design methods can be used to develop suitable chemical structures (linkers) for converting two naturally associated, but chemically separate, heavy and light polypeptide chains from an antibody variable region into a sFv molecule which folds into a three-dimensional structure that is substantially similar to native antibody structure. Design criteria include determination of the appropriate length to span the distance between the C-terminal of one chain and the N-terminal of the other, wherein the linker is generally formed from small hydrophilic amino acid residues that do not tend to coil or form secondary structures. Such methods have been described in the art. See, e.g., U.S. Pat. Nos. 5,091,513 and 5,132,405 to Huston et al.; and U.S. Pat. No. 4,946,778 to Ladner et al.

In this regard, the first general step of linker design involves identification of plausible sites to be linked. Appropriate linkage sites on each of the $V_H$ and $V_L$ polypeptide domains include those which result in the minimum loss of residues from the polypeptide domains, and which necessitate a linker comprising a minimum number of residues consistent with the need for molecule stability. A pair of sites defines a "gap" to be linked. Linkers connecting the C-terminus of one domain to the N-terminus of the next generally comprise hydrophilic amino acids which assume an unstructured configuration in physiological solutions and preferably are free of residues having large side groups which might interfere with proper folding of the $V_H$ and $V_L$ chains. Thus, suitable linkers under the invention generally comprise polypeptide chains of alternating sets of glycine and serine residues, and may include glutamic acid and lysine residues inserted to enhance solubility. Nucleotide sequences encoding such linker moieties can be readily provided using various oligonucleotide synthesis techniques known in the art.

Alternatively, a humanized antibody fragment may comprise the antigen binding site of a murine monoclonal antibody and a variable region fragment (lacking the antigen binding site) derived from a human antibody. Procedures for the production of chimeric and further engineered monoclonal antibodies include those described in Riechmann et al. (Nature 332: 323,1988), Liu et al. (PNAS 84: 3439,1987), Larrick et al. (Bio Technology 7: 934,1989), and Winter and Harris (TIPS 14: 139, May, 1993).

One method for producing a human antibody comprises immunizing a nonhuman animal, such as a transgenic mouse, with a target antigen, whereby antibodies directed against the target antigen are generated in said animal. Procedures have been developed for generating human antibodies in non-human animals. The antibodies may be partially human, or preferably completely human. Non-human animals (such as transgenic mice) into which genetic material encoding one or more human immunoglobulin chains has been introduced may be employed. Such transgenic mice may be genetically altered in a variety of ways. The genetic manipulation may result in human immunoglobulin polypeptide chains replacing endogenous immunoglobulin chains in at least some (preferably virtually all) antibodies produced by the animal upon immunization. Antibodies produced by immunizing transgenic animals with a target antigen are provided herein.

Mice in which one or more endogenous immunoglobulin genes are inactivated by various means have been prepared. Human immunoglobulin genes have been introduced into the mice to replace the inactivated mouse genes. Antibodies produced in the animals incorporate human immunoglobulin polypeptide chains encoded by the human genetic material introduced into the animal. Examples of techniques for production and use of such transgenic animals are described in U.S. Pat. Nos. 5,814,318, 5,569,825, and 5,545,806, which are incorporated by reference herein.

Monoclonal antibodies may be produced by conventional procedures, e.g., by immortalizing spleen cells harvested from the transgenic animal after completion of the immunization schedule. The spleen cells may be fused with myeloma cells to produce hybridomas, by conventional procedures.

A method for producing a hybridoma cell line comprises immunizing such a transgenic animal with a immunogen comprising at least seven contiguous amino acid residues of a target antigen; harvesting spleen cells from the immunized animal; fusing the harvested spleen cells to a myeloma cell line, thereby generating hybridoma cells; and identifying a hybridoma cell line that produces a monoclonal antibody that binds a target antigen. Such hybridoma cell lines, and monoclonal antibodies produced therefrom, are encompassed by the present invention. Monoclonal antibodies secreted by the hybridoma cell line are purified by conventional techniques.

In another embodiment, antibody fragments are produced by selection from a nonimmune phage display antibody repertoire against one set of antigens in the presence of a competing set of antigens (Stausbol-Grøn, B., et al., De novo identification of cell-type specific antibody-antigen pairs by phage display subtraction. Isolation of a human single chain antibody fragment against human keratin 14. Eur J Biochem 2001 May; 268(10):3099-107). This approach can be used to produce phage antibodies directed against target antigens. The protocol in general is based on that described by Stausbol-Grøn, B., et al., 2001. Briefly, a nonimmunized semisynthetic phage display antibody repertoire is used. The repertoire is a single chain Fv (scFv) phagemid repertoire constructed by recloning the heavy and light chain regions from the lox library (Griffiths, A. D., et al. (1994) Isolation of high affinity human antibodies directly from large synthetic repertoires. EMBO J. 13, 3245-3260.). *Escherichia coli* TG1 (supE hsdD5 Δ(lac-proAB) thi F'{traD36 proAB+lacI$^q$ lacZΔM15]) is an amber suppressor strain (supE) and is used for propagation of phage particles. *E. coli* HB2151 (ara A(lac-proAB) thi F'{proAB+lacI$^q$ lacZΔM15]) is a nonsuppressor strain and is used for expression of soluble scFv. In another embodiment, a human single-chain Fv (scFv) library can be amplified and rescued, as described (Gao, at al., Making chemistry selectable by linking it to infectivity, Proc. Natl. Acad. Sci. USA, Vol. 94, pp. 11777-11782, October 1997). The library is panned against target antigens suspended in PBS (10 mM phosphate, 150 mM NaCl, pH 7.4) and the positive scFv-phage are selected by enzyme-linked immunosorbent assay (ELISA).

In other preferred embodiments, an antibody is supplied by providing an expression vector encoding a recombinant antibody, preferably a single chain Fv antibody.

EXAMPLE 1

FIG. 1 is a schematic diagram 100 of a transverse section of a yeast cell wall, showing, from outside to inside, an outer fibrillar layer 110, an outer mannoprotein layer 120, a beta glucan layer 130, a beta glucan layer—chitin layer 140, an inner mannoprotein layer 150, the plasma membrane 160 and the cytoplasm 170.

Preparation of WGP Particles

Whole Glucan Particles (WGP, Lot WO282) were previously obtained from Alpha-Beta Technology. In general, whole glucan particles are prepared from yeast cells by the extraction and purification of the alkali-insoluble glucan fraction from the yeast cell walls. The yeast cells are treated with an aqueous hydroxide solution without disrupting the yeast cell walls, which digests the protein and intracellular portion of the cell, leaving the glucan wall component devoid of significant protein contamination, and having substantially the unaltered cell wall structure of β(1-6) and β(1-3) linked glucans. Yeast cells (*S. cerevisae* strain R4) were grown to midlog phase in minimal media under fed batch fermentation conditions. Cells (~90 g dry cell weight/L) were harvested by batch centrifugation at 2000 rpm for 10 minutes. The cells were then washed once in distilled water and then resuspended in 1 liter of 1M NaOH and heated to 90 degrees Celsius. The cell suspension was stirred vigorously for 1 hour at this temperature. The insoluble material, containing the cell walls, was recovered by centrifuging at 2000 rpm for 10 minutes. This material was then suspended in 1 liter, 1M NaOH and heated again to 90 degrees Celsius. The suspension was stirred vigorously for 1 hour at this temperature. The suspension was then allowed to cool to room temperature and the extraction was continued for a further 16 hours. The insoluble residue was recovered by centrifugation at 2000 rpm for 10 minutes. This material was finally extracted in 1 liter, water brought to pH 4.5 with HCl, at 75 degrees Celsius for 1 hour. The insoluble residue was recovered by centrifugation and washed three times with 200 milliliters water, four times with 200 milliliters isopropanol and twice with 200 milliliters acetone. The resulting slurry was placed in glass trays and dried at 55 degrees Celsius under reduced pressure to produce 7.7 g of a fine white powder.

A more detailed description of whole glucan particles and a process of preparing them can be found in U.S. Pats. Nos. 4,810,646; 4,992,540; 5,028,703; 5,607,677 and 5,741,495, the teachings of which are incorporated herein by reference. For example, U.S. Pat. No. 5,028,703 discloses that yeast WGP particles can be produced from yeast cells in fermentation culture. The cells were harvested by batch centrifugation at 8000 rpm for 20 minutes in a Sorval RC2-B centrifuge. The cells were then washed twice in distilled water in order to prepare them for the extraction of the whole glucan. The first step involved resuspending the cell mass in 1 liter 4% w/v NaOH and heating to 100 degrees Celsius. The cell suspension was stirred vigorously for 1 hour at this temperature. The insoluble material containing the cell walls was recovered by centrifuging at 2000 rpm for 15 minutes. This material was then suspended in 2 liters, 3% w/v NaOH and heated to 75 degrees Celsius. The suspension was stirred vigorously for 3 hours at this temperature. The suspension was then allowed to cool to room temperature and the extraction was continued for a further 16 hours. The insoluble residue was recovered by centrifugation at 2000 rpm for 15 minutes. This material was finally extracted in 2 liters, 3% w/v NaOH brought to pH 4.5 with HCl, at 75 degrees Celsius for 1 hour. The insoluble residue was recovered by centrifugation and washed three times with 200 milliliters water, once with 200 milliliters dehydrated ethanol and twice with 200 milliliters dehydrated ethyl ether. The resulting slurry was placed on petri plates and dried.

Preparation of YGMP Particles

*S. cerevisiae* (100 g Fleishmans Bakers yeast) was suspended in 1 liter 1M NaOH and heated to 55 degrees Celsius. The cell suspension was mixed for 1 hour at this temperature. The insoluble material containing the cell walls was recovered by centrifuging at 2000 rpm for 10 minutes. This material was then suspended in 1 liter of water and brought to pH 4-5 with HCl, and incubated at 55 degrees Celsius for 1 hour. The insoluble residue was recovered by centrifugation and washed once with 1000 milliliters water, four times with 200 milliliters dehydrated isopropanol and twice with 200 milliliters acetone. The resulting slurry was placed in a glass tray and dried at room temperature to produce 12.4 g of a fine, slightly off-white, powder.

Preparation of YGMP Particles

*S. cerevisiae* (75 g SAF-Mannan) was suspended in 1 liter water and adjusted to pH 12-12.5 with 1M NaOH and heated to 55 degrees Celsius. The cell suspension was mixed for 1 hour at this temperature. The insoluble material containing the cell walls was recovered by centrifuging at 2000 rpm for 10 minutes. This material was then suspended in 1 liter of water and brought to pH 4-5 with HCl, and incubated at 55 degrees Celsius for 1 hour. The insoluble residue was recovered by centrifugation and washed once with 1000 milliliters water, four times with 200 milliliters dehydrated isopropanol and twice with 200 milliliters acetone. The resulting slurry was placed in a glass tray and dried at room temperature to produce 15.6 g of a fine slightly off-white powder.

Preparation of YCP Particles

Yeast cells (*Rhodotorula* sp.) derived from cultures obtained from the American Type Culture Collection (ATCC, Manassas, Va.) were aerobically grown to stationary phase in YPD at 30 degrees Celsius. *Rhodotorula* sp. cultures available from ATCC include Nos. 886, 917, 9336, 18101, 20254, 20837 and 28983. Cells (1L) were harvested by batch centrifugation at 2000 rpm for 10 minutes. The cells were then washed once in distilled water and then resuspended in water brought to pH 4.5 with HCl, at 75 degrees Celsius for 1 hour. The insoluble material containing the cell walls was recovered by centrifuging at 2000 rpm for 10 minutes. This material was then suspended in 1 liter, 1M NaOH and heated to 90 degrees Celsius for 1 hour. The suspension was then allowed to cool to room temperature and the extraction was continued for a further 16 hours. The insoluble residue was recovered by centrifugation at 2000 rpm for 15 minutes and washed twice with 1000 milliliters water, four times with 200 milliliters isopropanol and twice with 200 milliliters acetone. The resulting slurry was placed in glass trays and dried at room temperature to produce 2.7 g of a fine light brown powder.

Figure 2A:
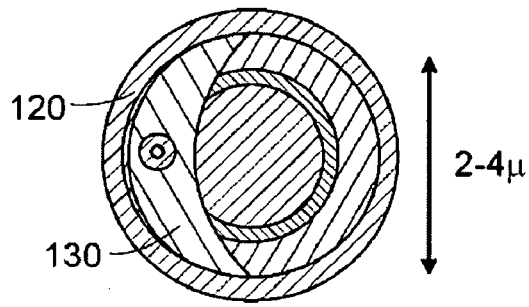
FIG. 2A is a diagram of the structure of a yeast cell wall particle.
Figure 2B:
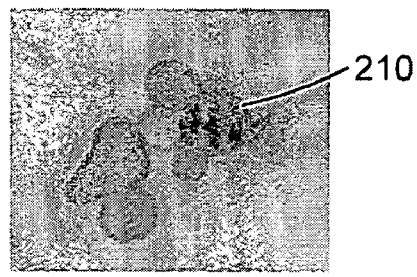
FIG. 2B is a reversed contrast (negative) grayscale image of a color fluorescence photomicrograph showing staining of the mannan component of the yeast cell wall particles by concanavalin-A-FITC (con-A-fluorescein isothiocyanate, Sigma Chemical, St. Louis, Mo.) showing substantially completely stained yeast cell wall particles 210.
Figure 2C:
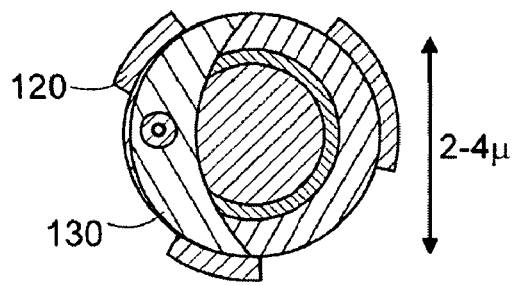
FIG. 2C is a diagram of the structure of a YGMP beta glucan-mannan particle.
Figure 2D:
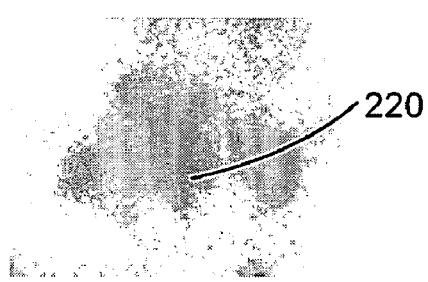
FIG. 2D is a reversed contrast (negative) grayscale image of a color fluorescence photomicrograph showing patchy con-A-FITC staining of a YGMP beta glucan-mannan particle 220.
Figure 2E:
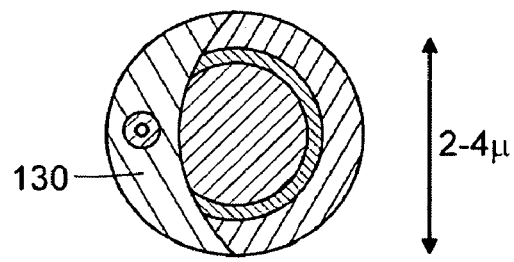
FIG. 2E is a diagram of the structure of a YGP beta glucan particle and FIG. 2F is a reversed contrast (negative) grayscale image of a color fluorescence micrograph showing the absence of con-A-FITC staining.
Figure 2F:
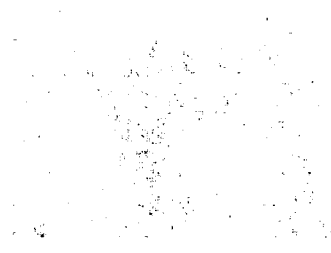

FIG. 2A is a diagram of the structure of a yeast cell wall particle; FIG. 2B is a fluorescence photomicrograph showing concanavalin-A-FITC (con-A-fluorescein isothiocyanate, Sigma Chemical, St. Louis, Mo.) staining of the mannan component of the yeast cell wall particles; FIG. 2C is a diagram of the structure of a YGMP beta glucan-mannan particle, FIG. 2D is a fluorescence photomicrograph showing punctuate con-A-FITC staining of a YGMP beta glucan-mannan particle; FIG. 2E is a diagram of the structure of a YGP beta glucan particle and FIG. 2F is a fluorescence micrograph showing the absence of con-A-FITC staining of a YGP beta glucan particle.

Concanavalin-A is a lectin that binds selectively to mannose. Concanavalin-A-FITC binding was evaluated by fluorescence microscopy in order to observe the amount and distribution pattern of mannan on the surface of various yeast cell wall preparations. Suspensions of Baker's yeast (Fleishmans Bakers yeast), YGMP and YGP in PBS+1 MM $MgCl_2$+1 mM $CaCl_2$ were prepared at a density of $1 \times 10^8$ particles/ml. Con-A-FITC stock was 1 mg/ml concanavalin-A-FITC in PBS+1 mM $MgCl_2$+1 mM $CaCl_2$. Labeling mixtures were prepared in microcentrifuge tubes consisting of:

100 µl PBS+1 mM $MgCl_2$+1 mM $CaCl_2$
2.5 µl yeast cell wall particle suspension
2.5 µl con-A-FITC stock solution.

The microcentrifuge tubes containing the labeling mixtures were incubated in the dark at room temperature for one hour. Yeast cell wall particles were collected by centrifugation (10,000 rpm for 10 minutes) followed by washing the pellet with 100 µl PBS three times. The washed yeast cell wall particles were resuspended in 100 µl PBS and transferred to a 96 well plate for examination with a fluorescence microscope. Photographs of exemplary fields are shown in FIGS. 2B, 2D and 2F.

Table 2 summarizes the results of analyses of the chemical composition of WGP particles, YGP particles, YGMP particles and YCP particles that were prepared as described above. Note that YGP particles and YGMP particles have lower beta-glucan content, generally between about 6 to about 90 weight percent, and higher protein content compared to the prior art WGP particles. YGMP particles have a substantially higher mannan content, generally more than about 30 weight percent, more preferably between about 30 to about 90 weight percent mannan, compared to the other particle types. YCP particles have a substantially higher chitin+chitosan content compared to the other particle types, generally more than 50 weight percent, more preferably between about 50 to about 75 weight percent.

TABLE 2

Chemical Composition of Yeast Cell Wall Materials

| Analyte | Method | WGP *S. cerevisiae* | YGMP *S. cerevisiae* | YGP *S. cerevisiae* | YCP *Rhodotorula* |
|---|---|---|---|---|---|
| Macromolecular Composition* | | | | | |
| Protein | Kjeldal | <1 | 4.5 | 4.9 | — |
| Fat | Base hydrolysis, Soxhlet extraction | <1 | 1.6 | 1.4 | — |
| Ash | Combustion | 1.2 | 1.9 | 1.6 | — |
| Carbohydrate Composition** | | | | | |
| Beta-Glucan | Enzymatic Hydrolysis | 90.3 | 41.9 | 77 | 6.5 |
| Chitin + chitosan (as glucosamine, n-acetyl glucosamine) | Monosac Analysis-Dionex | 2.1 | 2.3 | 2.4 | 68 |

TABLE 2-continued

Chemical Composition of Yeast Cell Wall Materials

| Analyte | Method | WGP S. cerevisiae | YGMP S. cerevisiae | YGP S. cerevisiae | YCP Rhodotorula |
|---|---|---|---|---|---|
| Mannan (as mannose) | Monosac Analysis-Dionex | <1 | 36.9 | 0.47 | 1.3 |
| Other Glucans (as non beta 1,3-glucose and other unmeasured sugars) | Monosac Analysis-Dionex | 6.2 | 10.9 | 11.2 | 0.2 |

*Results are reported % w/w of dry analyzed materials
**Results are reported % w/w carbohydrate
WGP—Whole Glucan Particle - Prior Art Technology;
YGMP—Yeast Glucan-Mannan Particle;
YGP—Yeast Glucan Particle;
YCP—Yeast Chitin Particle

EXAMPLE 2

Hydrodynamic Volume of Yeast Cell Wall Particles

The hydrodynamic volume of yeast cell wall particles was determined as a measure of the payload capacity of the particles. A 1 g aliquot of yeast cell wall particles was weighed in a tared 15 ml centrifuge tube to determine the weight of the dry particles. Water (12.5 ml) was added to the tube, and the tube was vortexed to mix the suspension of yeast cell wall particles. The particles were allowed to swell and absorb water for 30 minutes. The particle suspension was centrifuged at 2000 rpm for 10 minutes. The water was removed, the tube was weighed, and the weight of water absorbed was calculated. The hydrodynamic volume was calculated as the ratio of the weight of the water absorbed to the weight of the dry particles. Table 3 presents the results for two preparations of the prior art WGP and the YGP and YGMP of the present invention.

TABLE 3

Hydrodynamic Volume of Exemplary Yeast Cell Wall Preparations

| Yeast Cell Wall Particle | Hydrodynamic Volume (g water/g particles) |
|---|---|
| WGP Prep 1 | 9.7 |
| WGP Prep 2 | 6.9 |
| YGP | 8.3 |
| YGMP | 6.7 |

The lower hydrodynamic volume of WGP Prep 2 may be due to an increased number of fragmented particles in this preparation. With respect to the other particles, the "purer" YGP had a higher hydrodynamic volume than the YGMP.

In general, the payload volume was limited to <66% hydrodynamic volume to ensure quantitative absorption of the payload by the yeast cell wall particles. By this rule, <5.5 µl payload would be loaded per mg YGP particles and <4.4 µl payload would be loaded per mg YGMP particles.

EXAMPLE 3

Oral Bioavailability of YGP and YGMP

Fluorescently labeled yeast glucan particles (YGP-F) and fluorescently labeled yeast glucan-mannan particles (YGMP-F) were prepared for an uptake study. Starting materials were: 5 ml YGP (5 mg/ml in 0.1M borate buffer, pH 8), 5 ml YGMP (5 mg/ml in 0.1M borate buffer, pH8), dichlorotriazinyl aminofluorescein (DTAF), 20 mg/ml in DMSO, freshly prepared and 0.1M borate buffer, pH 8.

Labeling reactions were carried out at a 25 mg scale. Aliquots of 25 mg particles were suspended in 5 ml 0.1M borate buffer, pH 8 and sonicated to reduce clumps of particles to single particles. The particles were centrifuged and resuspended in 5 ml 0.1M borate buffer, pH 8. DTAF (0.5 ml 20 mg/ml) was added to the resuspended particles and incubated 2 days at 37 degrees Celsius. At the end of the incubation, 5 ml 1 M Tris buffer, pH 8.3, was added and the mixture was incubated 30 minutes to quench DTAF. The incubated particles were centrifuged and washed in PBS until the supernatants were no longer fluorescent. The washed particles were resuspended in PBS at 5 mg/ml. The number of particles in a 1:100 dilution of an aliquot was counted. Results: intensely fluorescent yeast cell wall particles were produced, at concentrations of $1.8 \times 10^9$ particles per ml YGP-F and $2.1 \times 10^9$ particles per ml YGMP-F.

The influence of the surface carbohydrate composition on the oral bioavailability of yeast glucan particles was studied to determine if the phagocytic particle uptake of a payload could be targeted via the mannose receptor as well as by the CR3/dectin-1 beta glucan receptors. The ability to target either or both receptors can expand the target population of cells beyond macrophages and dendritic cells.

The treatment groups are summarized in Table 4, below. Starting materials included: FITC-labeled yeast glucan particles (YGP-F), FITC-labeled yeast glucan-mannan particles (YGMP-F), a group of seven C57Black mice and a group of seven C57/B16 mice. Doses of YGP-F (1 mg/ml) and YGMP-F (3.7 mg/ml) were prepared to deliver equivalent number of particles in 0.1 ml PBS and administered by oral gavage to one mouse from each group daily for five days. The same dose was administered by subcutaneous injection of 0.1 ml to one mouse from each group daily for five days. On day four the cages were changed and fresh bedding was provided. Fecal pellets were collected on day 5 from each group into 15 ml conical tubes and frozen for processing later. The fecal pellets were processed by adding 5 ml water and holding at 4 degrees Celsius for 2 hours. The hydrated fecal pellets were homogenized using a Polytron homogenizer. Dilutions of homogenized feces were placed in a 96-well microtiter plate and microscopically examined under fluorescent and transmitted white light conditions for the presence of fluorescent particles. Aliquots having fluorescent particles were further diluted and the number of fluorescent particles/ml was counted with a hematocytometer.

Mice were sacrificed on day 7, and the spleen was removed from each animal and placed into separate tubes containing PBS on ice. The spleens were macerated with scissors and pressed through 70 micron screens to produce single cell suspensions. Aliquots of the single cell suspensions were retained and fixed in 1% formalin in PBS for quantifying the fraction of cells labeled with fluorescent particles using FACS. Cell suspensions are stained using a phycoerythrin (PE) labeled-antibody against macrophage marker, preferably murine Emr-1 (F4/80), which stains splenic red pulp macrophages, Kupffer cells, microglia and Langerhans cells.

Cell suspensions were plated at a density of $10^7$ cells per 60 mm petri dish in DMEM containing 10% fetal calf serum (JRH Scientific), penicillin-streptomycin and glutamine (Gibco) and incubated for 24 hours at 37 degrees Celsius under 5% $CO_2$ to allow for attachment. After the incubation, any unattached lymphocytes were washed away. The attached splenic macrophage cells were typsinized, fixed and scored for the fraction of adherent cells having fluorescent particles using a fluorescence microscope.

The administration of the fluorescent particles was well tolerated. Analysis of adherent splenic macrophages demonstrated the presence of fluorescent yeast cell wall particles in all fluorescent particle treated animals. These results demonstrate that both YGP-F and YGMP-F are orally bioavailable and can be systemically distributed by macrophages. The analysis of feces demonstrated the presence of fluorescent particles, indicating that oral absorption was incomplete at the dosage levels used. C57/B16 mice were able to absorb YGP-F and YGMP-F administered orally. The number of fluorescent particles in feces was quantified as an estimate of uptake efficiency.

TABLE 4

| Route | Treatment | Dose | mg/ml | # part./ml | # part./dose | Presence of Fluorescent Particles Splenic Macrophages | Feces |
|---|---|---|---|---|---|---|---|
| | Control | PBS control | — | — | — | | |
| SQ | YGP-F | 100 μg | 1 | $1 \times 10^9$ | $1 \times 10^8$ | + | − |
| Oral | YGP-F | 100 μg | 1 | $1 \times 10^9$ | $1 \times 10^8$ | + | + |
| Oral | YGP-F | 33 μg | 0.33 | $3.3 \times 10^8$ | $3.3 \times 10^7$ | + | + |
| SQ | YGPM-F | 370 μg | 3.7 | $1 \times 10^9$ | $1 \times 10^8$ | + | − |
| Oral | YGPM-F | 370 μg | 3.7 | $1 \times 10^9$ | $1 \times 10^8$ | + | + |
| Oral | YGPM-F | 110 μg | 1.1 | $3.3 \times 10^8$ | $3.3 \times 10^7$ | + | + |
| Untreated Control | — | — | — | — | — | − | − |

EXAMPLE 4

Preparation of Chitosan Loaded YGP Particles

YGP particles were prepared with a cationic trapping polymer, chitosan. 1% w/v chitosan solutions were prepared in 0.1M acetic acid using either High Molecular Weight (HMW) chitosan (~70,000 Mw, Sigma Chemical St. Louis, Mo.) or Low Molecular Weight (HMW) chitosan (~10,000 Mw, Sigma Chemical St. Louis, Mo.). Both 1% w/v HMW and LMW chitosan solutions were prepared in 0.1M acetic acid. Four ml HMW or LMW chitosan solution was added to 2 g YGP in a 50 ml conical centrifuge tube and mixed until a smooth paste was formed. The mixture was incubated for 1 hour at room temperature to allow the liquid to be absorbed. NaOH (40 ml, 0.1M) was added to each tube, which was vortexed immediately to precipitate the chitosan inside the YGP. The YGP:chitosan suspension was passed through an 18 gauge needle to produce a fine suspension of YGP:chitosan particles. The YGP:chitosan particles were collected by centrifugation (2,000 rpm for 10 minutes) followed by washing the pellet with deionized water until the pH of the supernatant was 7-8. The YGP:chitosan particles were then washed four times with two pellet volumes of isopropanol and then washed twice with two pellet volumes of acetone. The YGP:chitosan particles were then dried at room temperature in a hood. The procedure yielded 1.2 g YGP:LMW chitosan particles and 1.4 g YGP:HMW chitosan particles.

EXAMPLE 5

Preparation of CytoPure™ Loaded YGP Particles

YGP particles were prepared with a biodegradable cationic trapping polymer, CytoPure™, a proprietary, commercially available, water-soluble cationic polymer transfection reagent (Qbiogene, Inc., CA). Twenty μl CytoPure™ was diluted in 0.5 ml deionized water and added to 0.5 g YGP in a 50 ml conical centrifuge tube and mixed until a smooth paste was formed. The mixture was incubated for 15 minutes at 4 degrees Celsius to allow the liquid to be absorbed. Twenty-five ml ethanol was added to each tube, which was vortexed immediately to precipitate the CytoPure™ inside the YGP. The YGP:CytoPure™ suspension was sonicated to produce a fine suspension of YGP:CytoPure™ particles. The YGP:CytoPure™ particles were collected by centrifugation (2,000 rpm for 10 minutes) followed by washing the pellet four times with two pellet volumes of isopropanol and then washed twice with two pellet volumes of acetone. The YGP:CytoPure™ particles were then dried at room temperature in a hood. The procedure yielded 0.45 g YGP:CytoPure™ particles.

EXAMPLE 6

Preparation of Polyethylenimine Loaded YGP Particles

YGP particles were prepared with polyethylenimine (PEI) as a cationic trapping polymer. A 0.5 ml aliquot of a 2% w/v PEI (50,000 Mw, Sigma Chemical Co., St. Louis, Mo.) solution in water was added to 0.5 g YGP in a 50 ml conical centrifuge tube and mixed until a smooth paste was formed. The mixture was incubated for one hour at room temperature to allow the liquid to be absorbed. Twenty-five ml ethanol was added to each tube, which was vortexed immediately to precipitate the PEI inside the YGP. The YGP:PEI suspension was passed through an 18 gauge needle to produce a fine suspension of YGP:PEI particles. The YGP:PEI particles were collected by centrifugation (2,000 rpm for 10 minutes) followed by washing the pellet four times with two pellet volumes of isopropanol and then washed twice with two pellet volumes of acetone. The YGP:PEI particles were then dried at room temperature in a hood. The procedure yielded 0.48 g YGP:PEI particles.

EXAMPLE 7

Preparation of Alginate Loaded YGP Particles

YGP particles were prepared with alginate (F200 or F200L, Multi-Kem Corp., Ridgefield, N.J.) as an anionic trapping polymer. A 2 ml aliquot of a 1% w/v alginate solution in water was added to 1 g YGP in a 50 ml conical centrifuge tube and mixed to form a smooth paste. The mixture was incubated for one hour at room temperature to allow the liquid to be absorbed. The mixture was diluted with 40 ml of a 1% w/v calcium chloride aqueous solution. The YGP:alginate suspension was passed through an 18 gauge needle to produce a fine suspension of YGP:alginate particles. The YGP:alginate particles were collected by centrifugation (2,000 rpm for 10 minutes. The YGP:alginate particles were washed four times with two pellet volumes of isopropanol and then washed twice with two pellet volumes of acetone. The YGP:alginate particles were then dried at room temperature in a hood. The procedure yielded 0.95 g YGP:F200 alginate particles and 0.86 g YGP:F200L alginate particles.

EXAMPLE 8

Preparation of Poly-L-Lysine Loaded YGP and YGMP Particles

YGP and YGMP particles were prepared with Poly-L-lysine (PLL) as a trapping polymer. A 4 ml aliquot of a 1% w/v PLL (Sigma Chemical Co., St. Louis, Mo.) solution in water was added to 1 g YGP or YGMP in a 50 ml conical centrifuge tube. The mixture was incubated for 30 minutes at 55 degrees Celsius to allow the liquid to be absorbed. Ten ml ethanol was added to each tube, which was homogenized (Polytron homogenizer) to produce a fine suspension of YGP:PLL or YGMP:PLL particles. The YGP:PLL or YGMP:PLL particles were collected by centrifugation (2,000 rpm for 10 minutes. The YGP:PLL or YGMP:PLL were washed four times with two pellet volumes of isopropanol and then washed twice with two pellet volumes of acetone. The YGP:PLL or YGMP:PLL particles were then dried at room temperature in a hood. The procedure yielded 1.3 g YGP:PLL particles and 1.1 g YGMP:PLL particles. Microscopic evaluation showed no free PLL aggregates, only YGP:PLL or YGMP:PLL particles.

EXAMPLE 9

Preparation of Xanthan Loaded YGP and YGMP Particles

YGP and YGMP particles were prepared with xanthan as an anionic trapping polymer. A 4 ml aliquot of a 1% w/v xanthan solution in water was heated to 55 degrees Celsius to reduce viscosity and added to 1 g YGP or YGMP in a 50 ml conical centrifuge tube. The mixture was incubated for 30 minutes at 55 degrees Celsius. Ten ml ethanol was added to each tube, which was homogenized (Polytron homogenizer) to produce a fine suspension of YGP:xanthan or YGMP:xanthan particles. The YGP:xanthan or YGMP:xanthan particles were collected by centrifugation (2,000 rpm for 10 minutes). The YGP:xanthan or YGMP:xanthan particles were washed four times with two pellet volumes of isopropanol and then washed twice with two pellet volumes of acetone. The YGP:xanthan or YGMP:xanthan particles were then dried at room temperature in a hood. The procedure yielded 1.2 g YGP:xanthan particles and 1.1 g YGMP:xanthan particles. Microscopic evaluation showed no free xanthan aggregates, only YGP:xanthan or YGMP:xanthan particles.

EXAMPLE 10

Evaluation of Ability of YGP:Chitosan and YGP:Alginate To Bind Charged Dyes

YGP:Chitosan and YGP:Alginate particles were prepared as described in Examples 7 & 9 above. 0.1% w/v aqueous solutions of trypan blue (Benzamine blue; CI 23850), an anionic dye and xylene cyanol (acid blue, a cationic dye) were prepared. A 50 µl aliquot of a 0.1% w/v aqueous dye solution was added to 10 mg YGP, YGP:Chitosan or YGP:Alginate in microcentrifuge tubes and the mixture was incubated for 1 hour at room temperature. The pellets were washed with deionized water until the supernatant solutions were no longer colored. The color of the pellet was evaluated; the results are presented in Table 5, below.

TABLE 5

| | Pellet Color | |
|---|---|---|
| YGP Formulation | Trypan blue | Xylene cyanol |
| YGP | Tan | Tan |
| YGP: Chitosan | Blue | Tan |
| YGP: Alginate | Tan | Green |

Electrostatic interactions between insoluble trapping polymers inside YGP were capable of binding to oppositely charged low molecular weight model dye payloads.

EXAMPLE 11

Use of YGP:Agarose to Trap Molecules by Physical Entrapment

YGP:Agarose was prepared to evaluate physical entrapment as a means to trap a payload in YGP. A 2% w/v solution of agarose (Sigma Chemical Co., St. Louis, Mo.) was prepared in TE, and cooled to 50 degrees Celsius. A 1 mg/ml stock solution of salmon sperm DNA in TE was diluted to 0.5 mg/ml DNA in TE or in 1% agarose at 50 degrees Celsius. A 500 mg aliquot of YGP was mixed with 500 µl of DNA in TE or 500 µl of DNA in agarose at 50 degrees Celsius and the mixture was incubated 1 hour at 50 degrees Celsius. The mixture was then cooled for 1 hour in a refrigerator to solidify the agarose. After 1 hour, 10 mls of TE was added and the mixture was incubated overnight in refrigerator. The mixture was then centrifuged, and DNA in the supernatant was measured by absorption at 260 nm. About >80% of the applied DNA was retained by YGP:Agarose compared to <1% retained by the YGP:TE control. These results indicate that agarose effectively traps DNA inside YGP by physical entrapment.

EXAMPLE 12

Use of YGP:Polyacrylamide to Trap Molecules by Physical Entrapment

YGP:Polyacrylamide was prepared to evaluate physical entrapment as a means to trap a payload in YGP. A 1 mg/ml stock solution of salmon sperm DNA in TE was diluted to 0.5 mg/ml DNA in TE or in 30% polyacrylamide/bis (Sigma Chemical Co., St. Louis, Mo.). TEMED (N,N,N',N'-Tetramethylethylenediamine) was added to each DNA mixture (1 µl TEMED to 5 mls of DNA solution), and a 2 ml aliquot of each solution was added to 1 g YGP. The result was mixed to form a uniform suspension and incubated 3 hours at room temperature. After the 3 hour incubation, 10 ml of TE was added and the mixture was incubated overnight in a refrigerator. The mixture was then centrifuged, and DNA in the supernatant was measured by absorption at 260 nm. About >95% of the applied DNA was retained by YGP:Polyacrylamide compared to <1% retained by the YGP:TE control. These results indicate that polyacrylamide is an effective trapping polymer to use to trap DNA inside YGP by physical entrapment.

EXAMPLE 13

Loading YGP With A Small Molecule, Tetracycline

The antibiotic tetracycline (tet) was loaded into YGP using the relative insolubility of the tetracycline-calcium salt. Yeast cell wall particles used were YGP, YGP:F200 alginate and YGP: F200L alginate prepared as described above. Stock solutions were 1 M $CaCl_2$ and 100 mg/ml tetracycline HCl (Sigma Chemical Co., St. Louis, Mo.). The loading mixtures were set up as summarized in Table 6, below.

The mixtures were incubated for 30 minutes at room temperature and then deionized water or 1 M $CaCl_2$ was added as indicated. After 60 minutes at room temperature, the mixtures were sonicated and were incubated for at least an additional 30 minutes at room temperature. The mixtures were then centrifuged (2,000 rpm for 10 minutes) and the presence of tetracycline was indicated by the yellow color of the pellet and that of the initial supernatant. The amount of tetracycline loading into the yeast cell wall particles was calculated from the loss of absorption at 355 nm, the peak of the tetracycline absorption spectrum. A dilution of 4 µl of the 100 mg/ml tetracycline HCl stock solution in 200 µl deionized water had an absorbance at 355 nm of 0.538 compared to a deionized water blank. Release of tetracycline from the loaded yeast cell wall particles into PBS or 0.1M HCl was also measured spectrophotometrically.

The results are summarized in Table 6, above. In general, while YGP:F200 alginate and YGP:F200L alginate pellets were yellow after washing, YGP pellets were not yellow, indicating little, if any, tetracycline loading either as the hydrochloride or the calcium salt in the absence of a trapping polymer. In contrast, tetracycline was effectively loaded and trapped in YGP:F200 alginate and YGP:F200L alginate formulations, with about 25-30% of the applied tetracycline load absorbed as the calcium alginate salt. Trapped tetracycline was released from YGP:F200 alginate and YGP:F200L alginate into 0.1M HCl. The trapped tetracycline was partially retained in YGP:F200 alginate and YGP:F200L alginate in PBS for 1 hour at 37 degrees Celsius, about 26.5-51.6% of 0.1M HCl extractable.

In summary, tetracycline was readily trapped as a calcium alginate salt complex in a YGP-alginate-calcium composition, but was not effectively loaded and retained within YGP alone. The tetracycline trapped as a calcium alginate complex in YGP:F200 alginate and YGP:F200L alginate was slowly released in PBS at 37 degrees Celsius and substantially released under acid conditions.

EXAMPLE 14

Efficacy of Tet and YGP:Tet In Increasing in vitro Microbiocidal Killing of J774 Macrophages YGP: alginate—tet was prepared as described in Example 13, above. The numbers of particles of YGP and YGP: alginate—tet per ml in the stock solutions were 9 ×$10^7$/ml and 6×$10^8$/ml, respectively.

TABLE 6

| YGP (1 mg) | Tet (µl) | Water (µl) | 1M $CaCl_2$ (µl) | Loading | | | Release | |
|---|---|---|---|---|---|---|---|---|
| | | | | A355* | % tet | % tet | A355 | |
| | | | | super | bound | w/w | PBS | 0.1M HCl |
| — | — | — | 200 | 0 | — | — | — | — |
| — | 4 | 200 | — | 0.538 | — | — | — | — |
| — | 4 | — | 200 | 0.542 | — | — | — | — |
| YGP | — | — | 200 | 0.01 | — | — | — | — |
| YGP | 4 | 200 | — | 0.56 | 0 | — | — | — |
| YGP | 4 | — | 200 | 0.524 | <1 | — | — | — |
| YGP-F200 alginate | 4 | 200 | — | 0.405 | 24.8 | 9.9 | 3.6 | 4.9 |
| YGP-F200L alginate | 4 | 200 | — | 0.375 | 30.3 | 12.1 | 5.9 | 12.2 |

*1/100 dilution

TABLE 7

S. aureus Killing By J774 Murine Macrophages Loaded With YGP Particles

| YGP Tube | J774 $5 \times 10^5$/ml | DMEM + C | YGP/tet $5 \times 10^7$/ml | µl | Particles/ml | S. aureus Killed | Fold Increased Killing |
|---|---|---|---|---|---|---|---|
| a | 1 ml | 0.1 ml | — | — | — | $<1 \times 10^5$ | 1 |
| b | — | 1.1 ml | — | — | — | $<1 \times 10^5$ | 1 |
| c | 1 ml | — | YGP | 100 | $3 \times 10^7$ | $<1 \times 10^5$ | 1 |
| d | — | 1 ml | YGP | 100 | $3 \times 10^7$ | $<1 \times 10^5$ | 1 |
| e | 1 ml | — | YGP:tet | 100 | $3.75 \times 10^6$ | $1 \times 10^8$ | 100 |
| f | — | 1 ml | YGP:tet | 100 | $3.75 \times 10^6$ | $1 \times 10^6$ | — |
| g | 1 ml | — | YGP:tet | 100 | $7.5 \times 10^6$ | $>1 \times 10^8$ | >10 |
| h | — | 1 ml | YGP:tet | 100 | $7.5 \times 10^6$ | $1 \times 10^7$ | — |
| i | 1 ml | — | YGP:tet | 100 | $1.5 \times 10^7$ | $>1 \times 10^8$ | — |
| j | — | 1 ml | YGP:tet | 100 | $1.5 \times 10^7$ | $>1 \times 10^8$ | — |
| k | 1 ml | — | YGP:tet | 100 | $3 \times 10^7$ | $>1 \times 10^8$ | — |
| l | — | 1 ml | YGP:tet | 100 | $3 \times 10^7$ | $>1 \times 10^8$ | — |
| m | 1 ml | — | tet - 1.25 | 100 | 1.25 µg/ml | $1 \times 10^6$ | — |
| n | — | 1 ml | tet - 1.25 | 100 | 1.25 µg/ml | $1 \times 10^6$ | 1 |
| o | 1 ml | — | tet - 2.5 | 100 | 2.5 µg/ml | $1 \times 10^7$ | 3.3 |
| p | — | 1 ml | tet - 2.5 | 100 | 2.5 µg/ml | $3.3 \times 10^6$ | — |
| q | 1 ml | — | tet - 5 | 100 | 5 µg/ml | $>1 \times 10^8$ | — |
| r | — | 1 ml | tet - 5 | 100 | 5 µg/ml | $>1 \times 10^8$ | — |
| s | 1 ml | — | tet - 10 | 100 | 10 µg/ml | $>1 \times 10^8$ | — |
| t | — | 1 ml | tet - 10 | 100 | 10 µg/ml | $>1 \times 10^8$ | — |

One ml of murine macrophages, J774 ($5 \times 10^5$/ml) was combined with YGP, YGP: alginate—tet or tetracycline of various concentration as summarized in Table 6, above.

The J774 cells were cultured overnight in medium (DMEM containing 10% fetal calf serum without antibiotics or glutamine). The cultures were incubated with medium alone, tetracycline diluted in medium or particles diluted in medium for 1 hour with rotation at 37 degrees Celsius to permit phagocytosis of the particles. The microbial killing assay was set up in 96 well plates. The cultures were diluted in medium and incubated overnight to allow for metabolism and release of tet from phagocytosed YGP: alginate—tet particles. Bacterial challenge was added as indicated in Table 7 and the cultures were incubated 2 hours at 37 degrees Celsius in a $CO_2$ incubator to permit S. aureus phagocytosis and killing by the J774 murine macrophages. After this incubation, 200 µl LB Broth (Luria-Bertani Broth: 1.0% tryptone, 0.5% yeast extract, 1.0% NaCl) was added to each culture to lyze the macrophages. Cultures were incubated at 37 degrees Celsius in an incubator to permit outgrowth of surviving S. aureus. Growth was monitored by change in pH as indicated by phenol red. The effects of YGP, YGP: alginate—tet or tetracycline were compared. The results are provided in the two right-most columns of Table 7.

About $7.5 \times 10^6$ YGP: alginate—tet particles produced an effect on macrophages roughly equivalent to about 2.5 µg/ml tetracycline HCl. The macrophages alone were relatively less effective than macrophages treated with tetracycline in either mode, and about as effective as macrophages treated with empty YGP alone. Macrophages in combination with free tetracycline in solution were not much more effective than tetracycline alone. Macrophages treated with YGP: alginate—tet particles showed significant synergy. In general, the results demonstrate that phagosome delivery of tetracycline into J774 macrophage cells enhances the killing capacity of J774 macrophage cells for S. aureus.

EXAMPLE 15

Loading of Protein into YGP

The utility of the delivery system of the present invention for the retention, transport and delivery of therapeutic peptides or proteins, vaccine antigens or other peptides or proteins was evaluated using the mixed proteins of fetal calf serum. Yeast cell wall particles used were YGP, YGP-PEI and YGP-chitosan prepared as described above. Stock solutions were 45 ng/µl fetal calf serum (FCS) (Fetal Bovine Serum, JRH Biosciences, Lenexa, Kans.), 0.2% PEI (Sigma Chemical Co., St. Louis, Mo.) in TE, 0.05 M phosphate buffer, pH 7.2 (P buffer) and 0.05 M phosphate buffer, pH 7.2, 1 M NaCl (P+ salt buffer).

Four µl of FCS were added to 1 mg of YGP, YGP-P or YGP-CN in microcentrifuge tubes as indicated in Table 8 and the resulting mixture was incubated 60 minutes at room temperature to allow the liquid to be absorbed by the particles. After the incubation, 200 µl phosphate buffer or 200 µl PEI was as indicated in Table 8 and the resulting mixture was incubated 60 minutes at room temperature. After the incubation, 0.5 ml phosphate buffer was added, and after a further 5 minute incubation, the tubes were sonicated to produce single particles. The particles were pelleted by centrifuging at 10,000 rpm for 10 minutes and the supernatants were removed to fresh tubes. 0.5 ml 0.05 M sodium phosphate buffer, pH 7.2+1 M NaCl was added to the pellets, and after a further 5 minute incubation, the tubes were centrifuged at 10,000 rpm for 10 minutes and the high salt elution supernatants were removed to fresh tubes. The protein content of the supernatants was measured by absorbance at 280 nm.

TABLE 8

| Tube | YGP | 1° Load | 2° Load | P buffer (µl) | P + Salt buffer (µl) |
|---|---|---|---|---|---|
| 1 | — | 4 µl FCS | 200 µl P buffer | 500 | 500 |
| 2 | YGP | 4 µl FCS | 200 µl P buffer | 500 | 500 |
| 3 | YGP | 4 µl FCS | 200 µl 2% PEI | 500 | 500 |
| 4 | YGP-PEI | 4 µl FCS | 200 µl P buffer | 500 | 500 |
| 5 | YGP-CN | 4 µl FCS | 200 µl P buffer | 500 | 500 |

The protein loading results are shown in Table 9. YGP particles without a trapping molecule trapped only 5% of the presented protein. YGP particles that were loaded first with FCS protein and then exposed to PEI retained 47% of the protein load. YGP particles that were preloaded with a trapping polymer such as PEI or chitosan before exposure to the protein load such retained 68% and 60%, respectively, of the protein load.

TABLE 9

| Tube | YGP | Pay-load | Trapping Polymer | Unbound Protein (ng) | % Unbound Protein | Bound Protein (ng) | % Bound Protein |
|---|---|---|---|---|---|---|---|
| 1 | — | FCS | P buffer | 180 | 100 | — | — |
| 2 | YGP | FCS | P buffer | 180 | 95 | 10 | 5 |
| 3 | YGP | FCS | 2% PEI | 120 | 63 | 70 | 47 |
| 4 | YGP-PEI | FCS | P buffer | 60 | 32 | 130 | 68 |
| 5 | YGP-CN | FCS | P buffer | 80 | 40 | 120 | 60 |

The results demonstrate that serum proteins are not effectively loaded and trapped into YGP without trapping polymers. Using YGP that were preloaded with trapping polymers before exposure to the payload proteins resulted in increased protein trapping. Alternatively, proteins can be trapped inside YGP by first loading the protein, and then adding a soluble trapping polymer to sequester the protein within the particle.

EXAMPLE 16

Comparison of Various Methods of Loading DNA into YGP

Several methods of loading salmon sperm DNA into YGP, YGP containing low molecular weight (LMW) chitosans or YGP containing high molecular weight (HMW) chitosans were evaluated.

a. Capillary Loading Followed by Ethanol Precipitation

Salmon sperm DNA Sigma, St. Louis, Mo.) was sheared by 40 passes through 18 gauge needle and diluted to a concentration of 0.1 mg/ml in 50 mM TE (Tris-HCl, pH 8, 2 mM EDTA). Loading volumes of the DNA solution were determined and mixed in centrifuge tubes in duplicate with 100 mg aliquots of YGP, YGP: LMW chitosan or YGP: HMW chitosan as in Example 2 and incubated 1 hour. The incubated mixtures were ethanol precipitated by adding 1.5 ml ethanol to each tube. The insoluble products were collected by centrifugation at 2,000 rpm for 10 minutes. 10 ml TE was added to each tube, incubated for 1 hr at 37 degrees Celsius, centrifuged at 2,000 rpm for 10 minutes to sediment the insoluble YGP and the DNA content of the supernatant was determined by absorbance at 260 nm. The amount of DNA remaining in the YGP was calculated.

b. DNA Loading by Absorption

Loading volumes of the DNA solution were mixed in centrifuge tubes in duplicate with 100 mg aliquots of YGP, YGP: LMW chitosan or YGP: HMW chitosan as in Example 4a and incubated 1 hour. 10 ml TE was added to each tube, incubated for 1 hr at 37 degrees Celsius, centrifuged 2,000 rpm for 10 minutes to sediment the insoluble YGP. The DNA content of the supernatant was determined by absorbance at 260 nm. The amount of DNA remaining in the YGP was calculated.

c. DNA Loading by CTAB Trapping

Loading volumes of the DNA solution were mixed in centrifuge tubes in duplicate with 100 mg aliquots of YGP, YGP: LMW chitosan or YGP: HMW chitosan as in Example 4 and incubated 1 hour. The incubated mixtures were precipitated by adding 1.5 ml 2% hexadecyltrimethylammoniumbromide (also known as cetyltrimethylammonium bromide or CTAB) solution to each tube. 10 ml TE was added to each tube, which was incubated for 1 hr at 37 degrees Celsius, and centrifuged at 2,000 rpm for 10 minutes to sediment the insoluble YGP. The DNA content of the supernatant was determined by absorbance at 260 nm. The amount of DNA remaining in the YGP was calculated. The results are presented in Table 10, below.

TABLE 10

| | % DNA bound in YGP | | |
|---|---|---|---|
| Method | YGP | YGP: LMW chitosan | YGP: HMW chitosan |
| Direct Loading | <1% | 32% | 70% |
| Direct Loading + Ethanol | <1% | Not done | Not done |
| Direct Loading CTAB trapping | >99% | >99% | 99% |
| Absorption Loading | <1% | 5% | 12% |

Simple DNA loading or precipitation failed to effectively load and trap DNA into the YGP. In contrast, the use of the cationic trapping polymer, chitosan, resulted in the formation of chitosan-DNA complexes that can trap DNA inside YGP. In addition, the cationic agent CTAB can be effectively used to trap loaded DNA into YGP.

EXAMPLE 17

DNA Loading and Trapping

Fluorescent salmon sperm DNA was prepared by mixing 1 ml of a 1 mg/ml solution of salmon sperm DNA in 0.1 M carbonate buffer pH 9.2 with 100 µl of a 1 mg/ml suspension of DTAF in 10 mM carbonate buffer ph 9.2. After overnight incubation at 37 degrees Celsius, 200 µl 1M Tris-HCl pH 8.3 was added and incubated for 15 minutes at room temperature. Then, 100 µl 1 M NaCl and 3 mls ethanol were added to ethanol precipitate the DNA. After storage at −20C overnight, the ethanol precipitate was collected by centrifugation at 10,000 rpm 15 minutes. The ethanol precipitate was washed with 70% ethanol until supernatant was clear and resuspended in 1 ml TE.

The YGP suspensions were incubated for 30 minutes at room temperature. After the incubation, 0.45 ml 95% ethanol was added to one set (YGP, YGP-P, YGP-Chitosan) of three tubes, 0.2 ml 2% PEI was added to two sets of three tubes and 0.2 ml 2% CTAB was added to another set of three tubes. After 30 minutes incubation at room temperature, 0.2 ml 2% CTAB was added to one set of the PEI tubes and incubation proceeded for a further 30 minutes. Ethanol (1 ml, 95%) was added and the YGPs were stored overnight at −20 degrees Celsius. The YGP suspensions were washed with 70% ethanol and resuspended in 0.5 ml PBS. Results were evaluated by fluorescence microscopy, and are shown in Table 11.

TABLE 11

| Particle | Treatment | YGP pellet | Fluorescence Microscopy Observation |
|---|---|---|---|
| YGP | ethanol | White | Not fluorescent |
| YGP-CN | ethanol | Yellow | Internal particle fluorescence |
| YGP-P | ethanol | Yellow | Internal particle fluorescence |
| YGP | 2% PEI | Yellow | Internal particle fluorescence |
| YGP-CN | 2% PEI | Yellow | Weak internal particle fluorescence |
| YGP-P | 2% PEI | Yellow | Weak internal particle fluorescence |
| YGP | 2% CTAB | Yellow | Internal particle fluorescence |
| YGP-CN | 2% CTAB | Yellow | Strong internal particle fluorescence |

TABLE 11-continued

| Particle | Treatment | YGP pellet | Fluorescence Microscopy Observation |
|---|---|---|---|
| YGP-P | 2% CTAB | Yellow | Strong internal particle fluorescence |
| YGP | 2% PEI/2% CTAB | Yellow | Strong internal particle fluorescence |
| YGP-CN | 2% PEI/2% CTAB | Yellow | Internal particle fluorescence |
| YGP-P | 2% PEI/2% CTAB | Yellow | Internal particle fluorescence |

No significant trapping of fluorescent-labeled DNA occurred if only simple ethanol precipitation without a trapping polymer was used, demonstrating that the prior art technology is not effective as a DNA delivery system. Fluorescent-labeled DNA was clearly being trapped by cationic trapping polymers PEI or chitosan, or with the cationic detergent CTAP inside YGP particles. The best DNA trapping occurred when a combination of trapping polymer and CTAB was used, such as YGP:PEI: DNA:CTAB, YGP:chitosan: DNA: CTAB or YGP:DNA:PEI:CTAB.

EXAMPLE 18

Fluorescently Labeled Plasmid DNA Loading and Trapping

YGP containing pIRES plasmid was prepared for transfection and expression of encoded EGFP in J774 cells, a murine macrophage derived cell line. Cationic trapping agents used included cationic polymers such as polyethylenimine (PEI), CytoPure™, a proprietary, commercially available, water-soluble cationic polymer transfection reagent (Qbiogene, Inc., CA), chitosan and a cationic detergent hexadecyltrim-ethyl-ammoniumbromide (CTAB). A preferred PEI is JetPEI, a commercially available linear polyethylenimine cationic polymer transfection reagent (Qbiogene, Inc., CA).

pIRES-EGFP (Clonetech, CA) contains the internal ribosome entry site (IRES) of the encephalomyocarditis virus (ECMV) between the MCS and the EGFP (enhanced green fluorescent protein) coding region. This permits both the gene of interest (cloned into the MCS) and the EGFP gene to be translated from a single bicistronic mRNA. pIRES-EGFP is designed for the efficient selection (by flow cytometry or other methods) of transiently transfected mammalian cells expressing EGFP and another protein of interest. To optimize the selection of cells expressing high levels of the protein of interest, pIRES-EGFP utilizes a partially disabled IRES sequence (1). This attenuated IRES leads to a reduced rate of translation initiation at the EGFP start codon relative to that of the cloned gene. This enables the selection of those cells in which the mRNA, and hence the target protein, is produced at high levels to compensate for a suboptimal rate of translation of EGFP. This vector can also be used to express EGFP alone or to obtain stably transfected cell lines without time-consuming drug and clonal selection. EGFP is a red-shifted variant of wild-type GFP that has been optimized for brighter fluorescence and higher expression in mammalian cells. (Excitation maximum=488 nm; emission maximum=509 nm) EGFP encodes the GFPmut1 variant, which contains the amino acid substitutions Phe-64 to Leu and Ser-65 to Thr. These mutations increase the brightness and solubility of GFP, primarily due to improved protein folding properties and efficiency of chromophore formation. EGFP also contains an open reading frame composed almost entirely of preferred human codons. This leads to more efficient translation and, hence, higher expression levels in eukaryotic cells, relative to wild type GFP.

Solutions prepared were: pIRES EGFP plasmid DNA, 0.72 µg/µl in water, 0.2% w/v PEI (Sigma) in TE, 2 µl CytoPure (Qbiogene)+48 µl 0.15 M NaCl, 2 µl JetPEI (Qbiogene)+48 µl TE, 0.2% Spermidine in TE, 2% (aq) CTAB and phosphate buffered saline (PBS).

Fluorescent pIRES plasmid DNA was prepared by mixing 1 ml of a 1 mg/ml solution of pIRES DNA in 0.1 M carbonate buffer pH 9.2 with 100 µl of a 1 mg/ml suspension of DTAF in 10 mM carbonate buffer pH 9.2. After overnight incubation at 37 degrees Celsius, 200 µl 1M Tris-HCl pH 8.3 was added and incubated for 15 minutes at room temperature. Then 100 µl 1 M NaCl and 3 ml ethanol were added to ethanol precipitate the DNA. After storage at −20 degrees Celsius overnight, the ethanol precipitate was collected by centrifugation at 10,000 rpm 15 minutes. The ethanol precipitate was washed with 70% ethanol until supernatant was clear and resuspended in 1 ml TE.

The YGP suspensions were incubated for 30 minutes at room temperature. After the incubation, 0.45 ml 95% ethanol was added to one set (YGP, YGP-P, YGP-Chitosan) of three tubes, 0.2 ml 2% PEI was added to two sets of three tubes and 0.2 ml 2% CTAB was added to another set of three tubes. After 30 minutes incubation at room temperature, 0.2 ml 2% CTAB was added to one set of the PEI tubes and incubation proceeded for a further 30 minutes. Ethanol (1 ml, 95%) was added and the YGPs were stored overnight at −20 degrees Celsius. The YGP suspensions were washed with 70% ethanol and resuspended in 0.5 ml PBS.

J774 murine macrophages were plated in six well plates at a density of $2.5 \times 10^5$ cells per well and incubated overnight as described in Example 14. The transfections were performed as summarized in Table 12. The particles were added to the culture medium at a 10 particle per cell ratio and the plates were swirled to distribute particles. The cells were incubated for 4 hours. At end of the incubation period, the culture medium was removed, the cells were washed with PBS and fixed in 0.4% formalin in PBS.

TABLE 12

| Tube | pIRES µg/µl | vol µl | YGP mg | 0.2% PEI in TE | 0.2% Chitosan in Acetate buffer pH 5.5 | 2% CTAB | Ethanol |
|---|---|---|---|---|---|---|---|
| 1 | — | — | 1 | 200 µl | — | 200 µl | 800 µl |
| 2 | — | — | 1 | — | 200 µl | 200 µl | 800 µl |
| 3 | 1.8 | 4 | 1 | 200 µl | — | 200 µl | 800 µl |
| 4 | 1.8 | 4 | 1 | — | 200 µl | 200 µl | 800 µl |

Figure 3A:
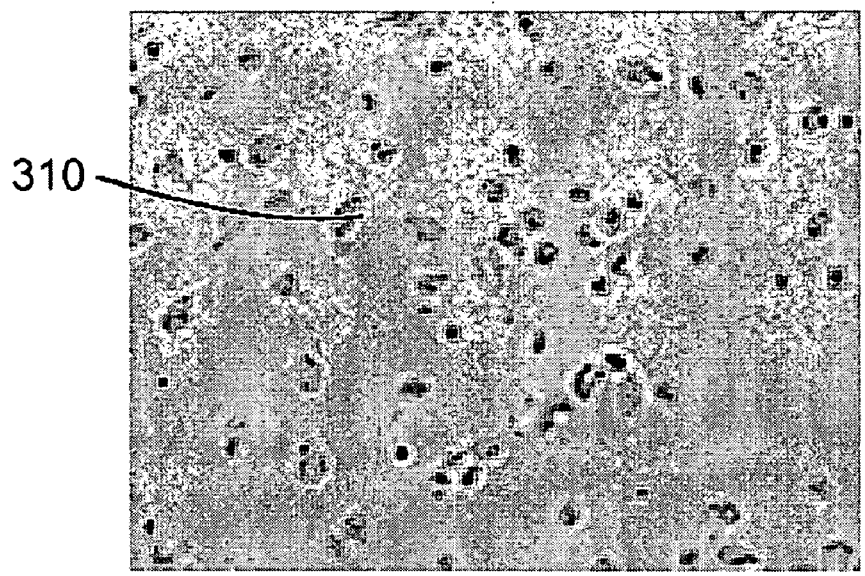
FIG. 3A is a reversed contrast (negative) grayscale image of a color light photomicrograph of cells exposed to YGP particles loaded with fluorescent labeled pIRES plasmid with PEI as the cationic trapping polymer and CTAB as a cationic detergent, indicating a cell 310
Figure 3B:
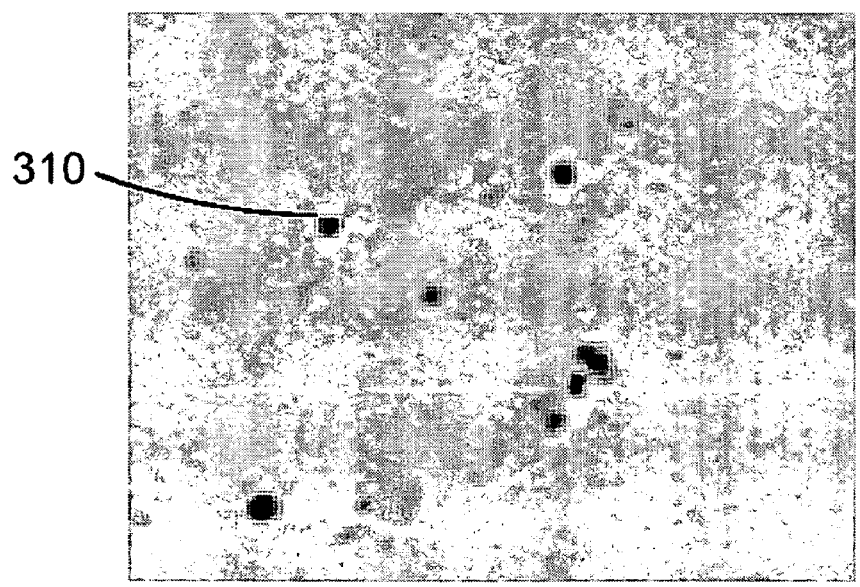
FIG. 3B is a reversed contrast (negative) grayscale image of a color fluorescence photomicrograph of the same field of cells showing bright staining representing fluorescent YGP particles internalized by the same cell 310 indicated in FIG. 3B.

Fluorescent DNA-containing particles and J774 cells incubated with fluorescent DNA-containing particles were evaluated by fluorescence microscopy, and results are summarized in Table 13 and shown in FIGS. 3A and 3B.

TABLE 13

| Particle Type | Treatment | Color of Pellet | Microscopic Examination of Particles |
|---|---|---|---|
| YGP | ethanol | White | No fluorescence |
| YGP-CN | ethanol | Yellow | Intracellular fluorescent particles |
| YGP-P | ethanol | Yellow | Intracellular fluorescent particles |
| YGP | 2% PEI | Yellow | Intracellular fluorescent particles |
| YGP-CN | 2% PEI | Yellow | Intracellular fluorescent particles |
| YGP-P | 2% PEI | Yellow | Intracellular fluorescent particles |

TABLE 13-continued

| Particle Type | Treatment | Color of Pellet | Microscopic Examination of Particles |
|---|---|---|---|
| YGP | 2% CTAB | Yellow | Intracellular fluorescent particles |
| YGP-CN | 2% CTAB | Yellow | Intracellular fluorescent particles |
| YGP-P | 2% CTAB | Yellow | Intracellular fluorescent particles |
| YGP | 2% PEI/2% CTAB | Yellow | FIGs. 3A & 3B; strongly fluorescent Intracellular particles |
| YGP-CN | 2% PEI/2% CTAB | Yellow | Intracellular fluorescent particles |
| YGP-P | 2% PEI/2% CTAB | Yellow | Intracellular fluorescent particles |

FIG. 3A is a reversed contrast (negative) grayscale image of a color light photomicrograph of cells exposed to YGP particles loaded with fluorescent labeled pIRES plasmid with PEI as the cationic trapping polymer and CTAB as a cationic detergent, indicating a cell 310. FIG. 3B is a reversed contrast (negative) grayscale image of a color fluorescence photomicrograph of the same field of cells showing bright staining representing fluorescent YGP particles containing fluorescent plasmid DNA internalized by the same cell 310 indicated in FIG. 3B.

EXAMPLE 19

EGFP Expression By J774 Murine Macrophages Incubated with YGP:pIRES

The pIRES plasmid DNA was not fluorescently labeled in this Example, rather the functional expression of the green fluorescent protein (GFP) encoded by pIRES was used as a demonstration of uptake of loaded yeast cell wall particles, intracellular release of the pIRES DNA and expression of the GFP as evidenced by the production of fluorescence.

The YGP: pIRES formulations were prepared as summarized in Table 14, below. DNA was prepared from dilutions in deionized water of 1 mg/ml stock. The indicated amount of DNA solution was added to YGP and incubated for at least 30 minutes to allow for liquid absorption. The indicated amount of 0.2% PEI in TE or 0.2% chitosan in acetate buffer was added and the mixture was allowed to incubate for 5 minutes before sonication to produce single particles. After a further incubation of at least 30 minutes, the indicated amount of 2% CTAB was added. After an additional 5 minute incubation, the tubes were vortex mixed and incubated again for at least 30 minutes. The indicated amount of 95% ethanol was added. Each tube was then mixed and stored at −20 Celsius overnight. The YGP:pIRES formulated particles were then centrifuged, washed twice in 70% ethanol, collected by centrifugation at 10,000 rpm for 5 minutes, resuspended in 0.5 ml sterile PBS and sonicated to produce single particles. The number of particles per ml was counted and each formulation was and stored at −20 degrees Celsius.

J774 murine macrophages were plated in 6 well plates at a density of $2.5 \times 10^5$ cells per well and incubated overnight as described in Example 14. The transfections were performed as summarized in Table 12, above. The particles were added to the culture medium at a 10 particle per cell ratio and the plates were swirled to distribute particles. The cells were fed daily and incubated for 2 days. At end of the incubation period, the culture medium was removed the cells were washed with PBS and fixed in 0.4% formalin in PBS.

Figure 4A:
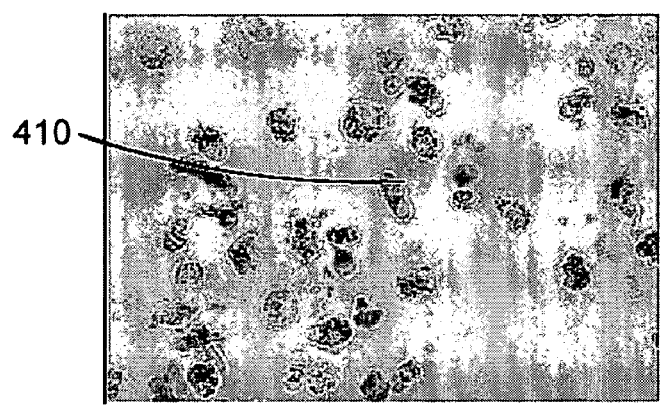
FIG. 4A is a reversed contrast (negative) grayscale image of a color fluorescence photomicrograph of cells, e.g., an indicated cell 410, exposed to fluorescent labeled YGP particles.
Figure 4B:
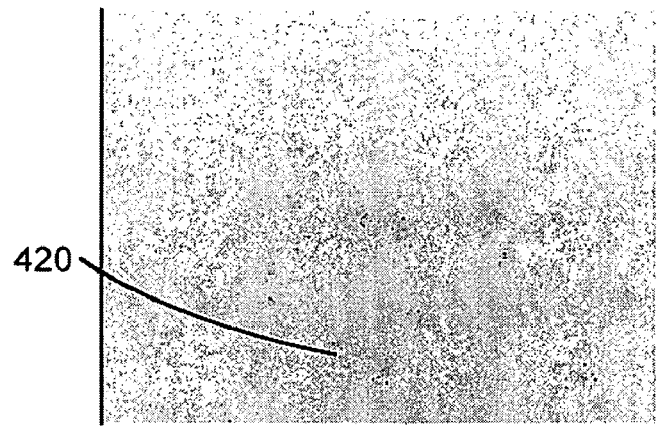
FIG. 4B is a reversed contrast (negative) grayscale image of a color fluorescence photomicrograph of cells, e.g., an indicated cell 420, exposed to YGP particles containing pIRES DNA, a cationic trapping polymer polyethylenimine (PEI) and cationic detergent hexadecyltrimethylammoniumbromide (also known as cetyltrimethylammonium bromide or CTAB) expressing GFP
Figure 4C:
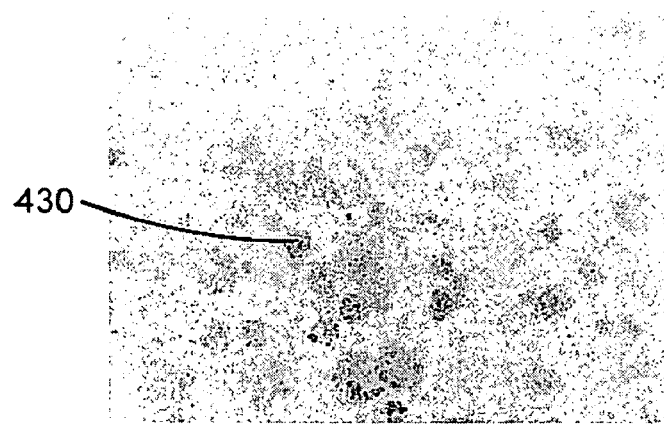
FIG. 4C is a reversed contrast (negative) grayscale image of a color fluorescence photomicrograph of cells, e.g., an indicated cell 430, exposed to YGP particles containing pIRES DNA, a cationic trapping polymer chitosan and cationic detergent CTAB expressing GFP.

The results are summarized in Table 14 and shown in FIGS. 4A-C. Cells were examined using fluorescence microscopy. Eighty nine percent of J774 cells took up YGP-F particles (Table 13, well 1B, FIG. 4A). EGFP expression was evident in >80% of J774 cells as punctate fluorescence in vacuoles in wells 1E (FIG. 4B) and 1F (FIG. 4C).

TABLE 14

| Well | Description | YGP/Cell | volume | Appearance |
|---|---|---|---|---|
| 1A | No Treatment Control | 0 | — | No detectible GFP fluorescent particles |
| 1B | YGPF Particle Uptake Control | 10 | 10 μl 1/10 | FIG. 4A, showing phagocytosis of fluorescent YGFP particles |
| 1C | YGP empty PEI/CTAB Control | 10 | 11 μl 1/10 | No detectible GFP fluorescent particles |
| 1D | YGP empty Chitosan/CTAB Control | 10 | 5 μl 1/10 | No detectible GFP fluorescent particles |
| 1E | YGP pIRES PEI/CTAB | 10 | 10 μl 1/10 | FIG. 4B, showing fluorescent GFP expression in cells |
| 1F | YGP pIRES Chitosan/CTAB | 10 | 6.5 μl 1/10 | FIG. 4C, showing fluorescent GFP expression in cells |

FIG. 4A is a reversed contrast (negative) grayscale image of a color fluorescence photomicrograph of cells, e.g., an indicated cell 410, exposed to fluorescent labeled YGP particles, FIG. 4B is a reversed contrast (negative) grayscale image of a color fluorescence photomicrograph of cells, e.g., an indicated cell 420, expressing GFP from pIRES DNA delivered by YGP with a cationic trapping polymer polyethylenimine (PEI) and cationic detergent hexadecyltrimethylammoniumbromide (also known as cetyltrimethylammonium bromide or CTAB) and FIG. 4C is a reversed contrast (negative) grayscale image of a color fluorescence photomicrograph of cells, e.g., an indicated cell 430, expressing GFP from pIRES DNA delivered by YGP with a cationic trapping polymer chitosan and cationic detergent CTAB.

EXAMPLE 20

Fluorescent DNA, Oligonucleotide and siRNA Oligonucleotide Delivery into J774 Cells Using YGP-Cation Trapping Polymer Technology The following materials were used: YGP:Fluorescent salmon sperm DNA:PEI:CTAB particles, YGP:Fluorescent oligonucleotide:PEI:CTAB particles, and YGP:Fluorescent siRNA:PEI:CTAB. The fluorescent oligonucleotide was an 18 mer synthesized by Sigma Genosys with a fluorescein residue attached to the 5' end:

5' Fluorescein-TTGGTCATCCATGGCTCT 3'. SEQ ID NO: 1

The fluorescent siRNA was a 21 mer non-silencing control siRNA synthesized with a fluorescein residue attached to the 5' end (Qiagen, Valencia, Calif., Catalog No. 1022079):

SEQ ID NO: 2
5' Fluorescein-UUCUCCGAACGUGUCACGUdTdT 3'.

J774 murine macrophages were plated in 6 well plates at a density of $2.5 \times 10^5$ cells per well and incubated overnight as described in Example 14. The transfections were performed as summarized in Table 15. The control and nucleic acid-loaded particles were added to the culture medium and the plates were swirled to distribute particles. The cells were fed daily and incubated for 24 hours. At end of the incubation period, the culture medium was removed the cells were washed with PBS and fixed in 0.4% formalin in PBS.

TABLE 15

| Well | Cells | YGP/Cell Ratio | Particles |
|---|---|---|---|
| 1A | J774 | 0 | — |
| 1B | J774 | 10 | YGPF |
| 1C | J774 | 10 | YGP DNAF |
| 1D | J774 | 10 | YGP oligoF |
| 1E | J774 | 10 | YGP RNAiF |

The results are illustrated in FIGS. 5A-I. Cells were examined using fluorescence microscopy and FACS. 92% of J774 cells took up YGP-F particles (Table 14, well 1B, FIG. 5A). Fluorescent oligonucleotide (SEQ ID NO:1) delivery was evident in >80% of J774 cells as punctate endosomal fluorescence and diffuse cytoplasmic fluorescence. Fluorescent non-silencing siRNA (SEQ ID NO:1) delivery was evident in >80% of J774 cells as punctate endosomal fluorescence and diffuse cytoplasmic fluorescence.

Figure 5A:
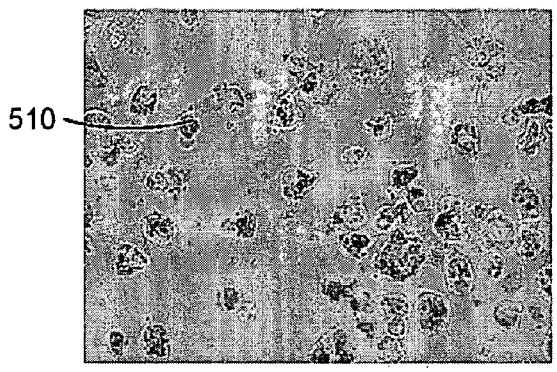
FIG. 5A is a reversed contrast (negative) grayscale image of a color combined light and fluorescence photomicrograph of cells, e.g., an indicated cell 510, exposed to fluorescent labeled YGP particles.
Figure 5B:
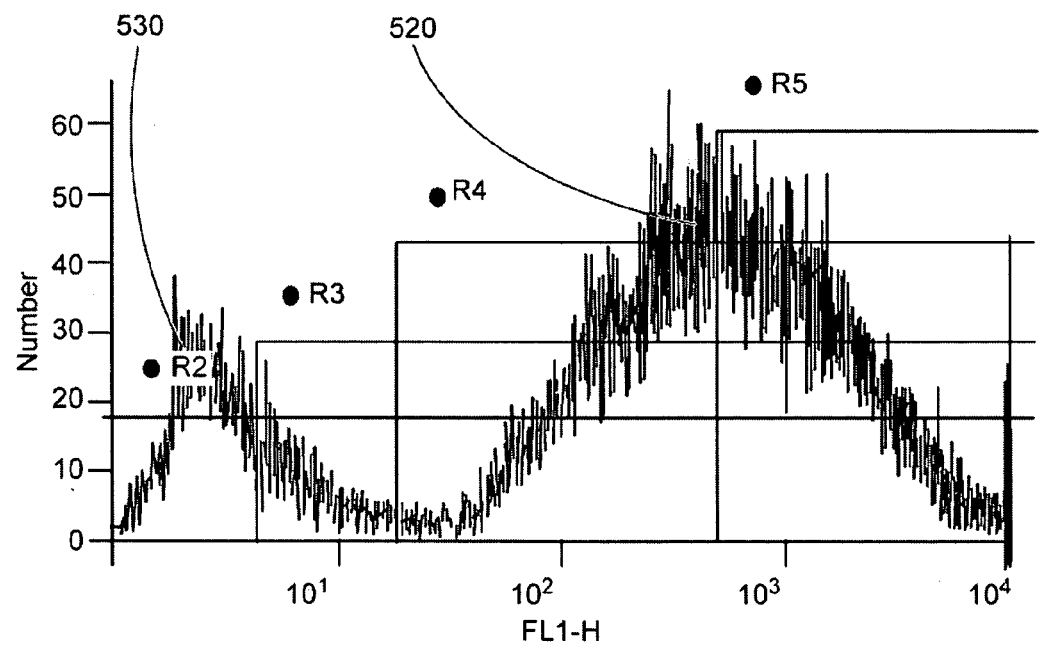
FIG. 5B is a graphic representation of the results of a fluorescence activated cell sorting (FACS) study showing a major peak 520 representing the distribution of signals from cells that have internalized fluorescent labeled YGP particles and a minor peak 530 representing the distribution of signals from cells without fluorescent labeled YGP particles.
Figure 5C:
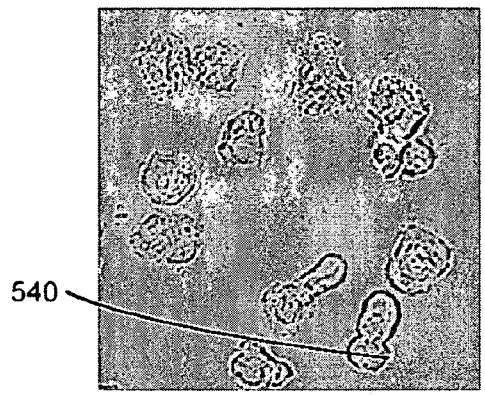
FIG. 5C is a reversed contrast (negative) grayscale image of a color light photomicrograph of cells, e.g., an indicated cell 540, exposed to YGP particles containing fluorescent labeled DNA, a cationic trapping polymer PEI and cationic detergent CTAB.
Figure 5D:
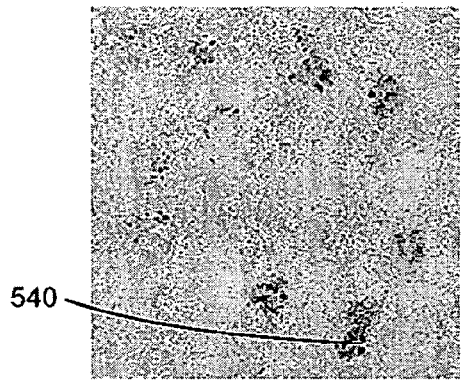
FIG. 5D is a reversed contrast (negative) grayscale image of a color fluorescence photomicrograph of the same field of cells showing the same indicated cell 540.
Figure 5E:
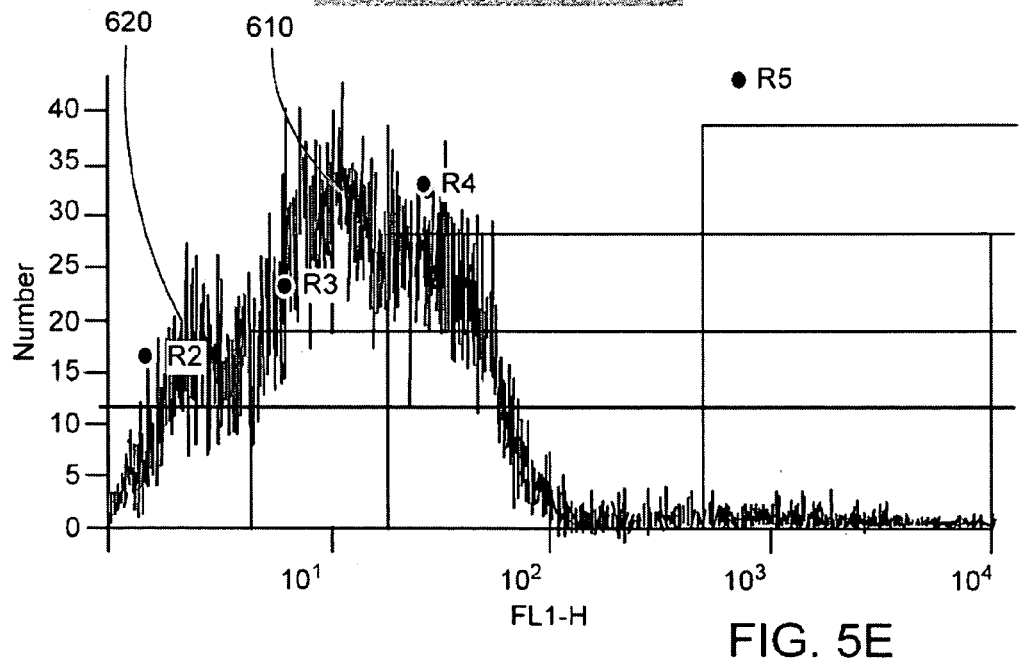
FIG. 5E is a graphic representation of the results of a FACS study showing a major peak 610 representing the distribution of signals from cells that have internalized YGP particles with fluorescent DNA payload and a shoulder 620 representing the distribution of signals from cells without YGP particles.
Figure 5F:
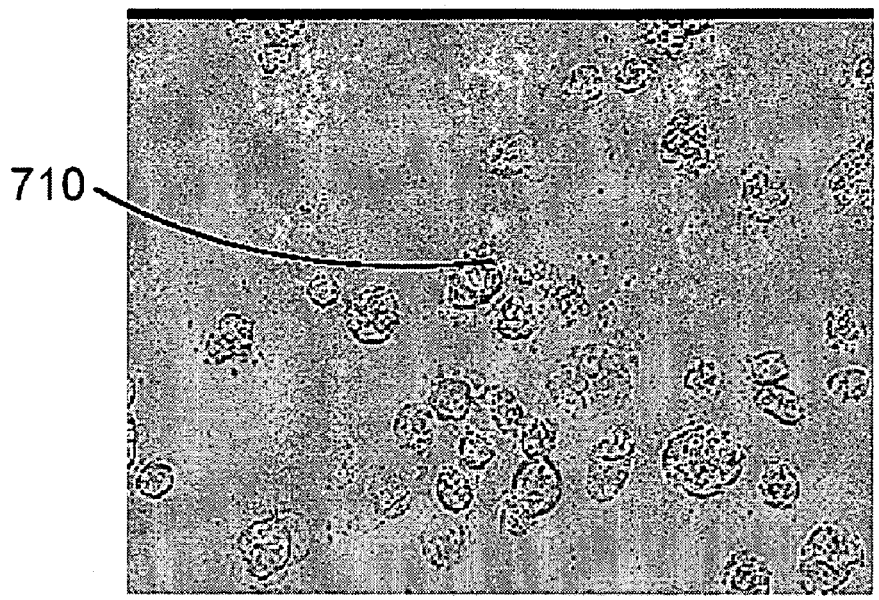
FIG. 5F is a reversed contrast (negative) grayscale image of a color light photomicrograph of cells, e.g., an indicated cell 710, incubated with YGP particles containing fluorescent antisense RNA payload.
Figure 5G:
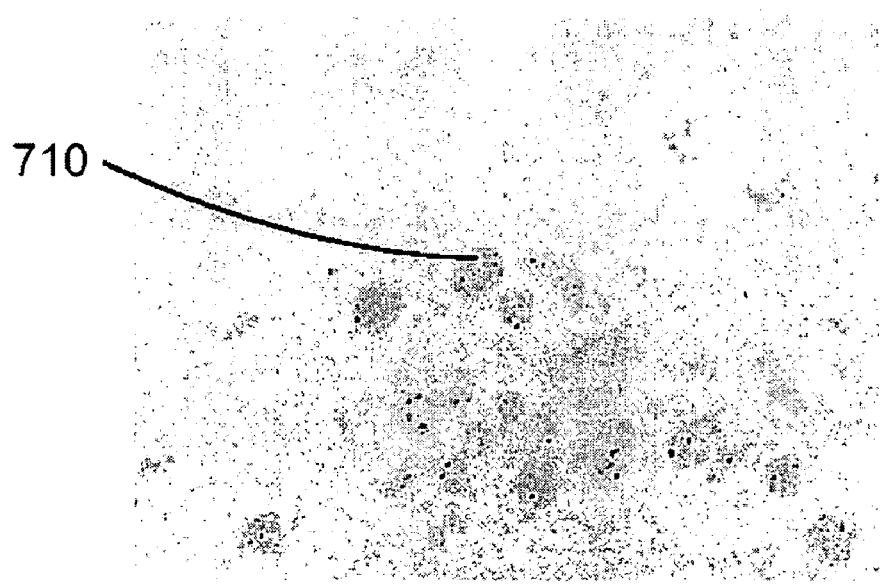
FIG. 5G is a reversed contrast (negative) grayscale image of a color fluorescence photomicrograph of the same field of cells showing the same indicated cell 710.
Figure 5H:
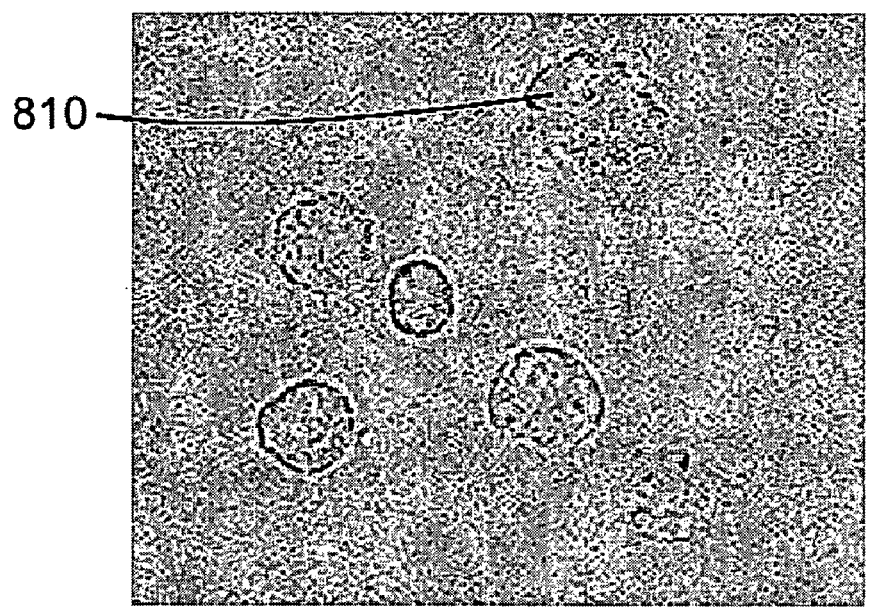
FIG. 5H is a reversed contrast (negative) grayscale image of a color light micrograph of cells, e.g., an indicated cell 810, incubated with YGP particles containing fluorescent labeled siRNA, PEI and CTAB
Figure 5I:
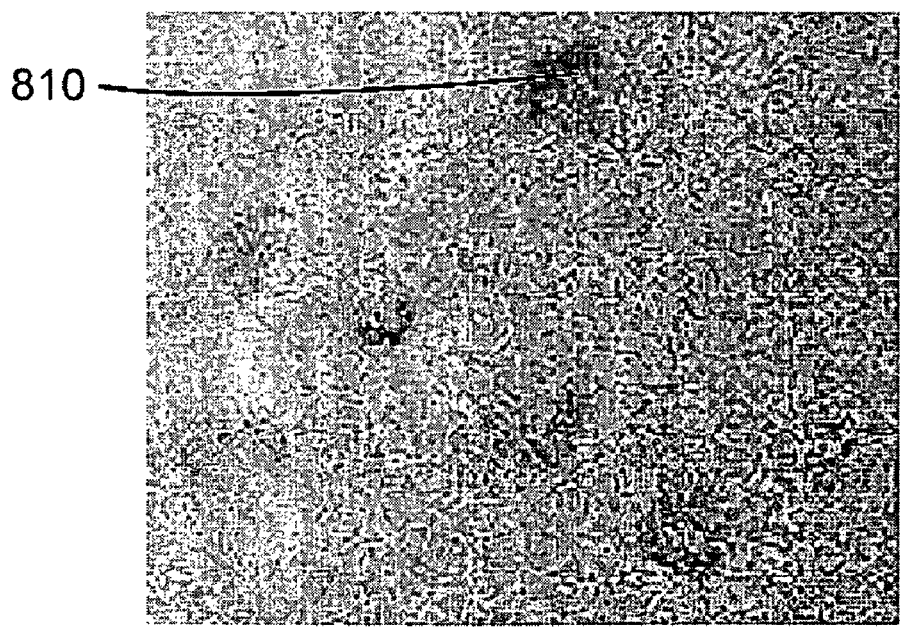
FIG. 5I is a reversed contrast (negative) grayscale image of a color fluorescence photomicrograph of the same field of cells showing the same indicated cell 810 containing internalized YGP particles with fluorescent RNAi payload.

FIG. 5A is a reversed contrast (negative) grayscale image of a color combined light and fluorescence photomicrograph of cells, e.g., an indicated cell 510, exposed to fluorescent labeled YGP particles; FIG. 5B is a graphic representation of the results of a fluorescence activated cell sorting (FACS) study showing a major peak 520 representing the distribution of signals from cells that have internalized fluorescent labeled YGP particles and a minor peak 530 representing the distribution of signals from cells without fluorescent labeled YGP particles; FIG. 5C is a reversed contrast (negative) grayscale image of a color light photomicrograph of cells, e.g., an indicated cell 540, exposed to YGP particles containing fluorescent labeled DNA, a cationic trapping polymer PEI and cationic detergent CTAB; FIG. 5D is a reversed contrast (negative) grayscale image of a color fluorescence photomicrograph of the same field of cells showing the same indicated cell 540, FIG. 5E is a graphic representation of the results of a FACS study showing a major peak 610 representing the distribution of signals from cells that have internalized YGP particles with fluorescent DNA payload and a shoulder 620 representing the distribution of signals from cells without YGP particles; FIG. 5F is a reversed contrast (negative) grayscale image of a color light photomicrograph of cells, e.g., an indicated cell 710, incubated with YGP particles containing fluorescent labeled antisense RNA, PEI and CTAB; FIG. 5G is a reversed contrast (negative) grayscale image of a color fluorescence photomicrograph of the same field of cells showing the same indicated cell 710 containing internalized YGP particles with fluorescent antisense RNA payload; FIG. 5H is a reversed contrast (negative) grayscale image of a color light micrograph of cells, e.g., an indicated cell 810, incubated with YGP particles containing fluorescent labeled siRNA, PEI and CTAB and FIG. 5I is a reversed contrast (negative) grayscale image of a color fluorescence photomicrograph of the same field of cells showing the same indicated cell 810 containing internalized YGP particles with fluorescent RNAi payload.

In summary, fluorescent DNA, oligonucleotide or siRNA payloads loaded into YGP using a cationic trapping polymer efficiently delivers the payload into J774 cells. Payloads are released from the endosomal compartment within 24 hours into the cytoplasm and nuclear compartments.

EXAMPLE 21

YGP-DNA Formulations Deliver a Plasmid DNA (pMFG-GC) Expressing hGC Efficiently into a Murine Macrophage Cell Line J774.

Methods as described above in Example 18 were used to deliver a plasmid DNA (pMFG-GC) expressing hGC into a murine macrophage cell line J774 and demonstrate expression of the gene product, human glucocerbrosidase. Compositions used were prepared as described above and are listed in Table 16, below. In addition, formulations comprising yeast cell wall particles containing pIRES were prepared as described above.

TABLE 16

| [DNA] ug/ul | DNA 0.1 mg/ml | vol μl | YGP mg | 0.2% PE in TE | 2% CTAB | Ethanol | Particles/ml |
|---|---|---|---|---|---|---|---|
| 2 | pMFG-GC | 4 | YGP | 200 | 200 | 800 | 7.3 × 10E8 |
| 2 | pMFG-GC | 4 | YGP-CN | — | 200 | 800 | 6.5 × 10E8 |

The pMFG-GC type vectors used have been described previously (Fabrega, S., et al., Human glucocerebrosidase: heterologous expression of active site mutants in murine null cells. Glycobiology. 2000 November; 10(11):1217-24). The vector comprises human GC cDNA inserted between the Nco I and Bam HI sites of the MFG backbone. MFG vectors, which retain the viral splice donor (SD) and splice acceptor (SA) sites, use the Maloney murine leukemia virus 5' long terminal repeat (5' LTR) to generate a spliced mRNA responsible for expression of the inserted sequence. Human GC cDNA was cloned into the MFG vector such that the start codon was precisely at the start codon of the deleted env gene. When used to transduce mouse bone marrow cells, cultured macrophages exhibited on average, four times the enzymatic activity of control macrophages.

Adherent cells in culture were grown in DMEM (Gibco)+ 10% fetal calf serum and penicillin-streptomycin-glutamine (Gibco) tissue culture media in plastic multiwell plates. At appropriate confluency, the culture media was removed, the cells washed briefly with PBS, and then fixed (with 0.5-1% formalin or paraformaldehyde solution). After removal of fixative, the cells were washed briefly with PBS and then incubated at RT for 1 hr in 0.1% bovine serum albumin/0.05% Tween 20. After removal of the 0.1% bovine serum albumin/ 0.05% Tween 20 solution, the cells were then incubated at 4 degrees Celsius overnight with a rabbit antisera to human glucocerebrosidase (1/1000-1/5000 working dilution; Ginns et. al. Proc. Natl. Acad. Sci. USA. Vol. 79:5607-5610, September 1982) in PBS/0.05% Tween 20.

After the overnight incubation, the antibody solution was removed from the cells, and the cells were washed five times for 3 min with PBS/0.05% Tween 20 with gentle rocking. The cells were then incubated with goat anti-rabbit FITC conjugated antisera (Molecular Probes F2765, fluorescein goat anti-rabbit IgG (H+L), 2 mg/mL; 1/100-1/500 working dilution) for 1-2 hr at RT.

The cells were again washed five times for 3 min with PBS/0.05% Tween 20 with gentle rocking. After removal of the final wash solution, PBS was added to each well and the cell plates were stored at 4 degrees Celsius in the dark until fluorescent microscopic analysis.

TABLE 17

| Well | YGP construction | μl | Day | 1' Antibody | 2' Antibody |
|---|---|---|---|---|---|
| 1A | — | — | 3 | Anti-human glucocerebrosidase | 200 ul goat anti-rabbit IgG-F |
| 1B | YGP-F | 5 | 3 | — | — |
| 1C | YGP:pMFG-GC:PEI:CTAB | 4.8 | 3 | Anti-human glucocerebrosidase | 200 ul goat anti-rabbit IgG-F |
| 1D | YGP-CN:pMFG-GC:PEI:CTAB | 17.9 | 3 | Anti-human glucocerebrosidase | 200 ul goat anti-rabbit IgG-F |

FIGS. 6A-6G are grayscale images of a color photomicrographs of J774 murine macrophage cells showing uptake of yeast cell wall particles containing pMFG-GC expression vectors and expression of human glucocerebrasidase (hGC). Cells were exposed to a YGP formulation or untreated (control), cultured, and adherent cells were formalin fixed. Fixed cells were processed for immunocytochemistry using a primary anti-human GC antibody (rabbit antisera), an appropriate detectible secondary antibody (goat anti-rabbit FITC conjugated antisera), examined by fluorescence microscopy and photographed.

Figure 6A:
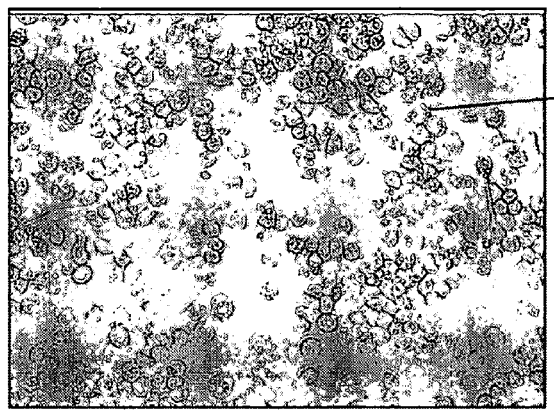
FIGS. 6A-6G are grayscale images of a color photomicrographs of J774 murine macrophage cells showing uptake of yeast cell wall particles containing pMFG-GC expression vectors and expression of human glucocerebrasidase (hGC). Cells were exposed to a YGP formulation or untreated (control), cultured, and adherent cells were formalin fixed. Fixed cells were processed for immunocytochemistry using a primary anti-human GC antibody (rabbit antisera), an appropriate detectable secondary antibody (goat anti-rabbit FITC conjugated antisera), examined by fluorescence microscopy and photographed.

FIG. 6A is a grayscale image of a color transmitted light photomicrograph of J774 cells, e.g., an indicated cell 510, from an untreated control culture.

Figure 6B:
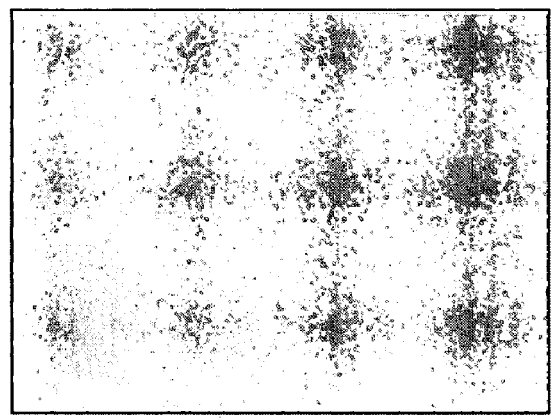

FIG. 6B is a grayscale image of a color fluoescence photomicrograph of the same field of J774 cells showing a lack of fluorescently labeled cells.

Figure 6C:
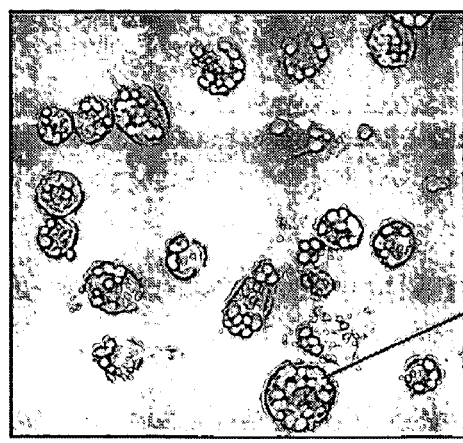

FIG. 6C is a grayscale image of a color combined light and fluorescence photomicrograph of J774 cells exposed to a formulation of fluorescently labeled yeast cell wall particles (YGP-F) showing cells, e.g., cell 912, containing fluorescently labeled particles.

Figure 6D:
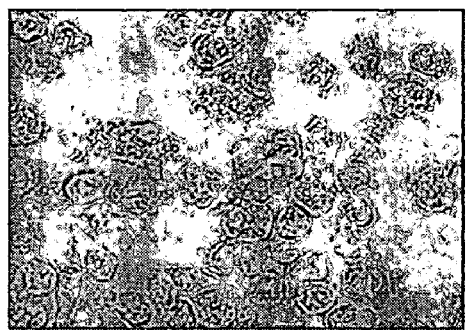
Figure 6E:
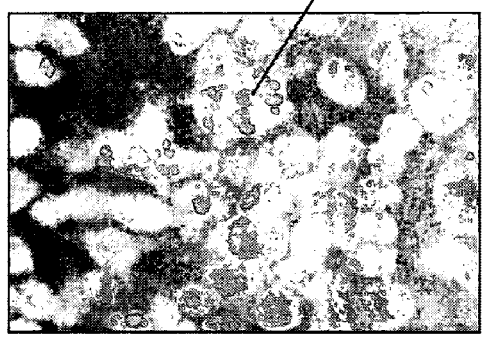

FIGS. 6D and 6E are grayscale images of a color transmitted light photomicrograph and color fluorescence photomicrograph, respectively, of the same field of J774 cells exposed to a formulation of yeast cell wall particles containing pMFG-GC expression vectors (YGP:pMFG-GC:PEI:CTAB) showing expression of human glucocerebrosidase (hGC) by immunoreactivity in fluorescently labeled cells, e.g., cell 914.

Figure 6F:
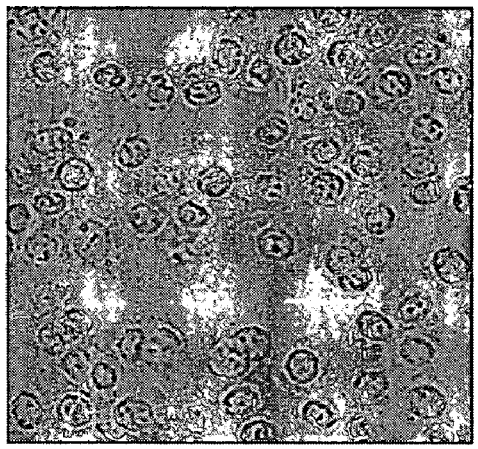
Figure 6G:
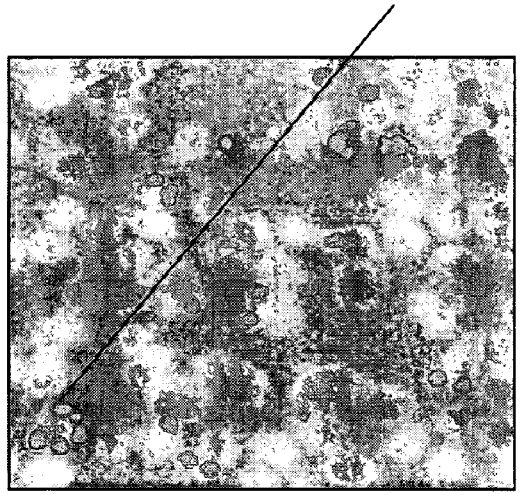
Figure 7A:
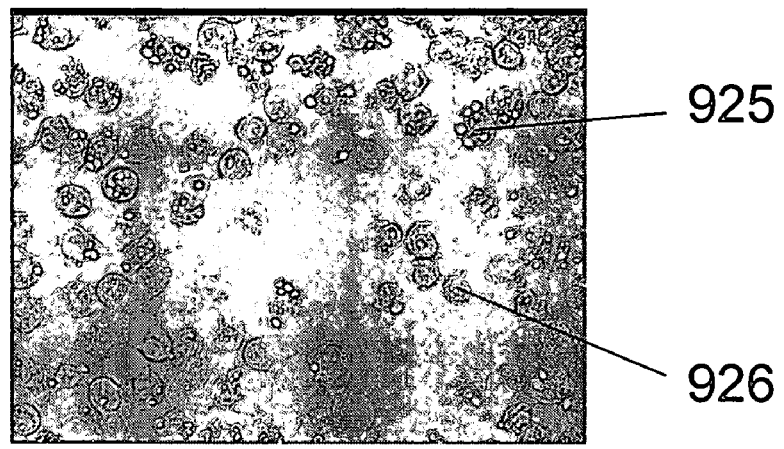
FIG. 7A is a grayscale image of a color combined light and fluorescence photomicrograph of J774 cells exposed to a formulation of fluorescently labeled yeast cell wall particles (YGMP-F) showing cells, e.g., cell 925, containing fluorescently labeled particles and other cells, e.g., cell 926, lacking fluorescently labeled particles.
Figure 7B:
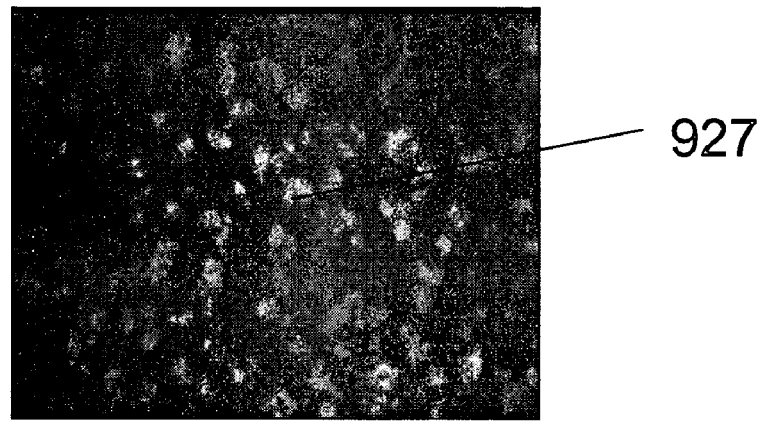
FIG. 7B is a grayscale image of a color fluorescence photomicrograph of J774 cells exposed to a formulation of yeast cell wall particles containing a pIRES expression vector (YGMP-pIRES) showing expression of green fluorescent protein (GFP) by in fluorescently labeled cells, e.g., cell 927.
Figure 7C:
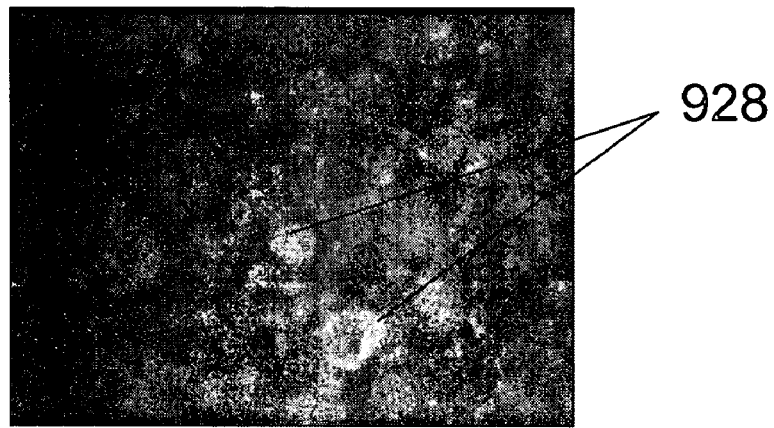
FIG. 7C is a grayscale image of a color fluorescence photomicrograph of J774 cells exposed to a formulation of yeast cell wall particles containing a pMFG-GC expression vector (YGMP-MFG-GC) showing expression of human glucocerebrosidase (hGC) by immunoreactivity in fluorescently labeled cells, e.g., cell 928.

FIGS. 6F and 6G are grayscale images of a color transmitted light photomicrograph and color fluorescence photomicrograph, respectively, of the same field of J774 cells exposed to a formulation of yeast cell wall particles containing pMFG-GC expression vectors (YGP-CN:pMFG-GC:CTAB) showing expression of human glucocerebrosidase (hGC) by immunoreactivity in fluorescently labeled cells, e.g., cell 916.

The general results of these studies can be summarized as follows. Cells of the murine macrophage cell line J774 phagocytosed YGP-F particles efficiently (>90%). The human anti-glucocerebrosidase antibody used selectively stained the recombinant human protein and did not cross-react with endogenous mouse protein. Human glucocerebrosidase expression was detectable as immunoreactivity in >50% of J774 cells treated in vitro with YGP pMFG-GC CTP formulations. Both YGP:MFG-GC:PEI:CTAB and YGP-CN:pMFG-GC:CTAB formulations were effective for delivering plasmid DNA and inducing detectable expression of human glucocerebrosidase in J774 cells. Human glucocerebrosidase appeared to be normally processed and was detected in the endosomal and lysosomal compartments. YGP:CTP formulations are effective at delivering the human glucocerbrosidase gene on pMFG-GC and promoting expression of human glucocerebrosidase in murine J774 macrophage cells.

EXAMPLE 22

Figure 8:
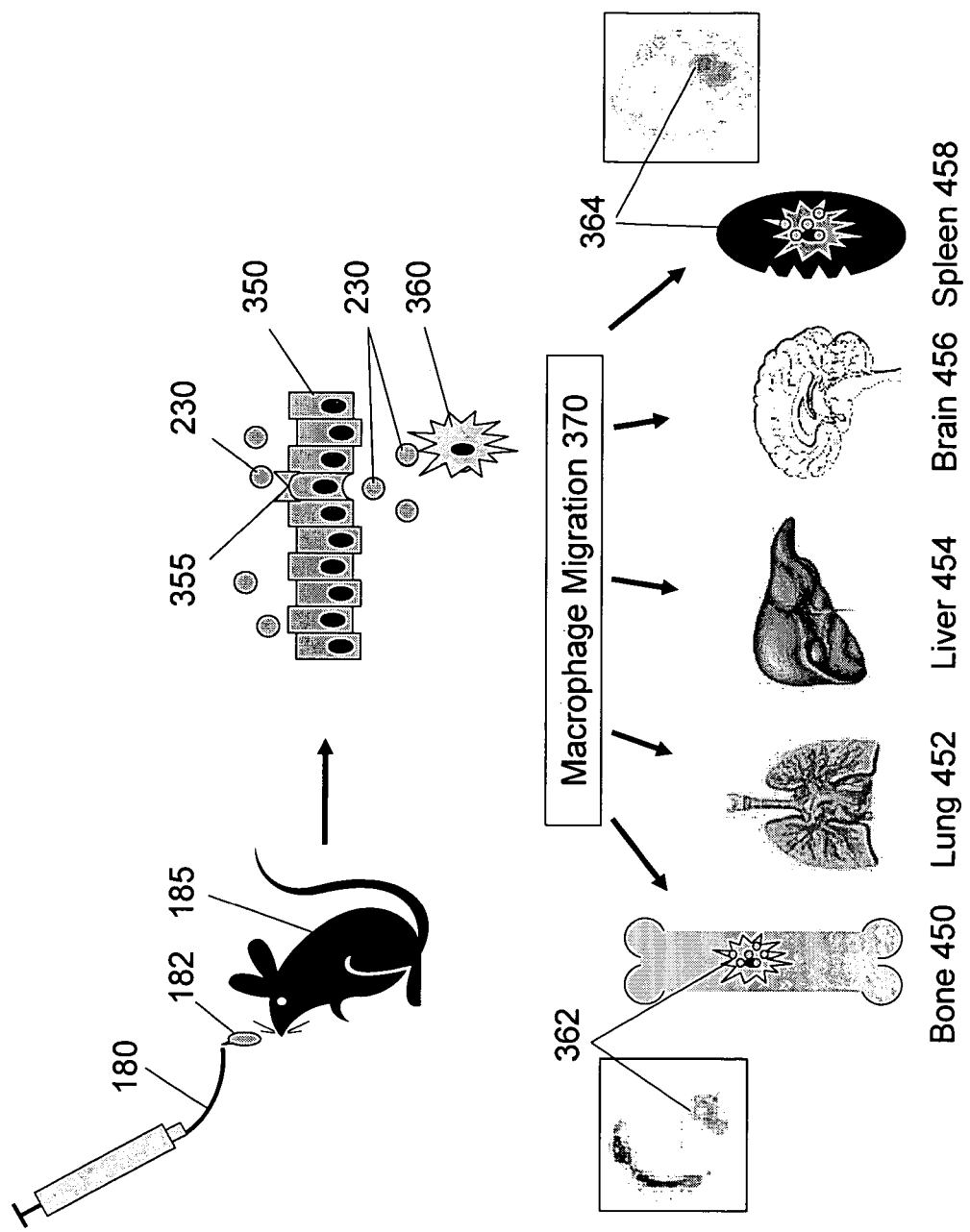
FIG. 8 is a schematic diagram of a preferred embodiment of the method of delivering yeast beta glucan particles (YGP) 230 by macrophage migration 370 to various organs 450, 452, 454, 456, 458 after in vivo oral administration 180. A composition 182 containing yeast beta glucan particles (YGP) 230 is administered orally 180 to a subject 185. The yeast beta glucan particles (YGP) 230 are take up by M cells 355 in the lining of the small intestine and are translocated across the epithelium 350 and are phagocytosed by intestinal macrophages 360. The YGP-containing macrophages migrate 370 to organs and tissues including bone 450, lung 452, liver 454, brain 456 and spleen 458. About 72 hours after oral administration, splenic macrophages 364 that had phagocytosed YGP were observed in the spleen 458 (shown both schematically and in a reversed contrast grayscale image of a color fluorescence photomicrograph). About 90 hours after oral administration, bone marrow macrophages 362 that had phagocytosed YGP were observed in bone 450 (shown both schematically and in a reversed contrast grayscale image of a color fluorescence photomicrograph).

Oral Bioavailability of YGP and YGMP Fluorescent Particles in Wild-Type and Gaucher's Mice FIG. 8 is a schematic diagram of a preferred embodiment of the method of delivering yeast beta glucan particles (YGP) 230 by macrophage migration 370 to various organs 450, 452, 454, 456, 458 after in vivo oral administration 180. A composition 182 containing yeast beta glucan particles (YGP) 230 is administered orally 180 to a subject 185. The yeast beta glucan particles (YGP) 230 are taken up by M cells 355 in the lining of the small intestine and are translocated across the epithelium 350 and are phagocytosed by intestinal macrophages 360. The YGP-containing macrophages migrate 370 to organs and tissues including bone 450, lung 452, liver 454, brain 456 and spleen 458. About 72 hours after oral administration, splenic macrophages 364 that had phagocytosed YGP were observed in the spleen 458 (shown both schematically and in a reversed contrast grayscale image of a color fluorescence photomicrograph). About 90 hours after oral administration, bone marrow macrophages 362 that had phagocytosed YGP were observed in bone 450 (shown both schematically and in a reversed contrast grayscale image of a color fluorescence photomicrograph).

The effect of cell surface carbohydrate composition on oral bioavailability of yeast glucan particles was studied using fluorescently labeled yeast cell wall particles, YGP-F (FITC-labeled yeast glucan particles) and YGMP-F (FITC-labeled yeast glucomannan particles) were prepared as described above. Aliquots (0.1 ml) of YGP-F and YGMP-F were administered to mice (C57B1/6 wild type and Gaucher model mice) by oral gavage and subcutaneous injection for 5 days. Brain, liver, bone marrow, small intestine and a section of spleen from each animal were fixed and examined by fluorescence microscopy to determine the extent of fluorescent yeast cell wall particle uptake. An aliquot of spleen was placed on ice and processed to produce single cell suspensions. Splenic cells were plated at ~$10^6$ cells per 12 well plate and incubated for 24 hours to allow for attachment. After washing away unbound cells, the wells are scored for adherent cells (macrophages) with internalized fluorescent particles by fluorescence microscopy.

Yeast cell wall particles were also shown to be useful and effective for in vivo delivery (oral and parenteral routes) of the human glucocerbrosidase gene in pMFG-GC constructs, producing expression of human glucocerebrosidase in splenic macrophage cells. Formulations incorporating MFG-GC plasmid DNA expressing human GC into yeast glucan particles (YGP) and yeast glucan-mannan particles (YGMP) in the form of cationic polymer-DNA nanocomplexes were prepared as described above. The data show that these YGP-DNA and YGMP-DNA microparticles become bioavailable through receptor mediated uptake into tissue, mucosal and gut associated lymphatic tissue (GALT) macrophages when administered orally or parenterally. Direct receptor mediated uptake into tissue macrophages via carbohydrate receptor binding to the particle surface glucan and mannan polysaccharides occurs when the DNA loaded microparticles are systemically administered. Upon phagocytosis by cells, the particles are engulfed into endosomes where the cationic polymer releases the DNA, swelling the endosome and releasing the DNA into the cytoplasm where it migrates to the nucleus. The released DNA is processed by cellular machinery to produce normal human GC enzyme.

Two mouse models of Gaucher disease were used. The first Gaucher mouse was produced by injecting C57/B1 mice with 100 mg/kg of conduritol beta-epoxide, (CBE, 7-oxabicyclo [4.1.0]heptane-2,3,4,5-tetrol), intraperitoneally daily for 3 weeks. Three weeks of treatment of 3 month old C57/B1 mice with CBE produced an approximately 50% and 500% increase in the amount of glucosylceramide in systemic tissues and brain, respectively. There was a drastic reduction in β-glucosidase activity in CBE treated mice, but the levels of other hydrolytic enzymes (α-mannosidase, β-hexosaminidase, α-galactosidase, α-glucosidase and β-glucuronidase) were not significantly different from that of control mice. No weight or behavioral differences occurred in 3 month old treated mice. In contrast, 1 day old infant C57/B1 mice treated with 100 mg/kg CBE IP daily for 3 weeks had a significant difference in growth compared to controls. Expressed as percentages of total body weight there was no difference for brain, liver, and kidney, but the spleen weight was 60% of control. The CBE treated infant mice manifested tail arching, a potentiated high amplitude action tremor and minimal startle response, but normal swimming and righting response, all suggestive of CNS gray matter involvement. There was a 50% and 300% increase in glucocerebroside in liver tissue and brain, respectively.

Similar to the treated 3 month old mice, the treated infant mice had drastically reduced β-glucosidase activity. However, while α-glucosidase and β-galactosidase were close to normal, activity of hexosaminidase and mannosidase were elevated. These mice have provided an opportunity to study the pathogenesis of Gaucher disease, but the short lived effects of CBE injection makes these mice less useful for studying the longer term effects of enzyme and gene replacement therapy A transgenic mouse model of Gaucher disease was used in which amino acid substitutions were made in murine glucocerebrosidase that produced a significant reduction in endogenous GC expression to a level less than half that of the enzyme activity in normal littermates. Assay of glucocerebrosidase activity in mouse samples was performed using 4-methylumbellerferyl-glucopyranoside (4MUGP), a fluorescently labeled substrate. The point mutations, analogous to those found in the more mildly affected Gaucher disease patients, were introduced into a genomic clone of murine glucocerebrosidase by PCR mutagenesis. The modified clones were inserted into an appropriate vector and transfected into RW4 murine embryonic stem (ES) cells by electroporation. ES clones containing the correctly targeted mutation in one allele of the glucocerebrosidase gene were injected into blastocysts from C57BL/6 mice using standard techniques which were then transferred to foster mice. Male offspring from these injections were test-bred against C57BL/6 females, and the progeny were screened by PCR and Southern analyses for transmission of the mutant glucocerebrosidase allele.

Long lived murine models of human Gaucher phenotypes are valuable for developing new therapeutic strategies. Previously, a knockout mouse was created by targeted disruption of the glucocerebrosidase gene that is a murine model of type 2 Gaucher disease. These homozygous affected mice have no glucocerebrosidase activity, store lipid in macrophages, have icthyotic skin, and die within 24 hours of birth. The ultrastructure of the storage material in lysosomes closely resembles that of the human patients. Further studies used a single insertion mutagenesis procedure to introduce mutations associated with two known human phenotypes. These insertional RecNcil mutation mice had low enzyme activity and accumulated glucosylceramide, while the L444P mice had higher enzyme levels. However both these insertional mutation Rec-Ncil and L444P mice died within 48 hours.

Figure 9A:
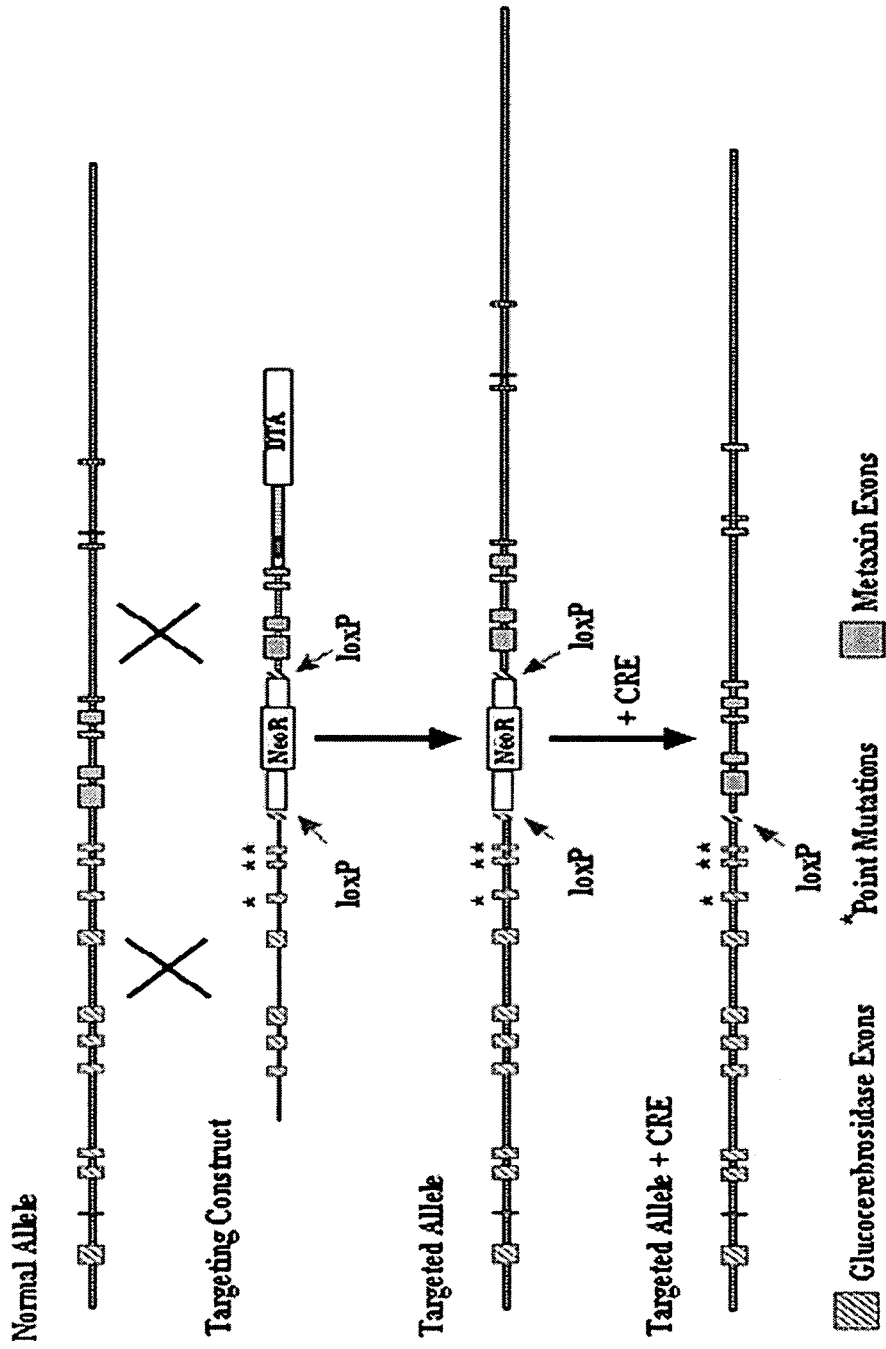
FIG. 9A and FIG. 9B are schematic illustrations of thee use of a replacement vector that contains loxP to generate a longer lived mouse model of Gaucher disease carrying the L444P, R463C And N370S Point Mutations.
Figure 9B:
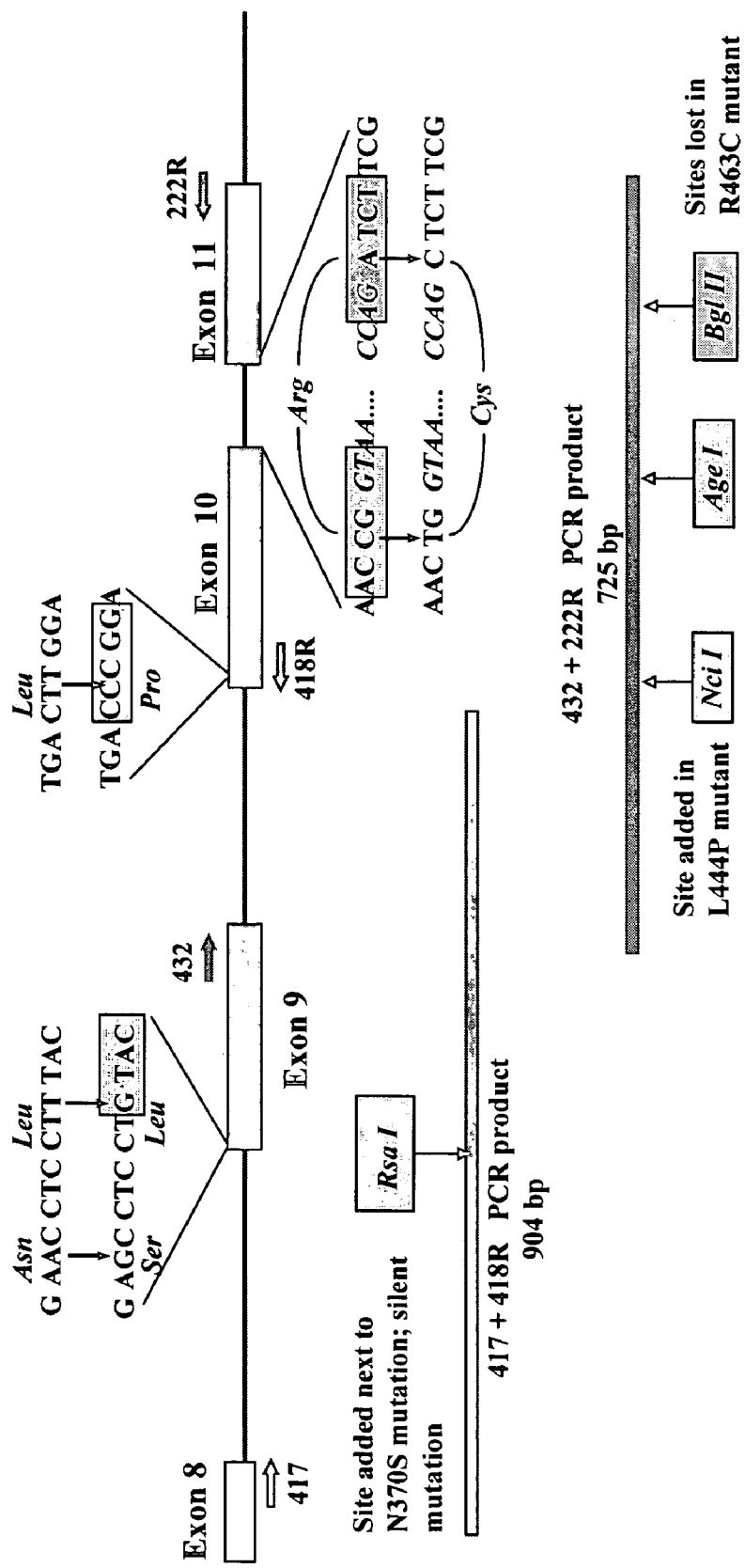
Figure 10A:
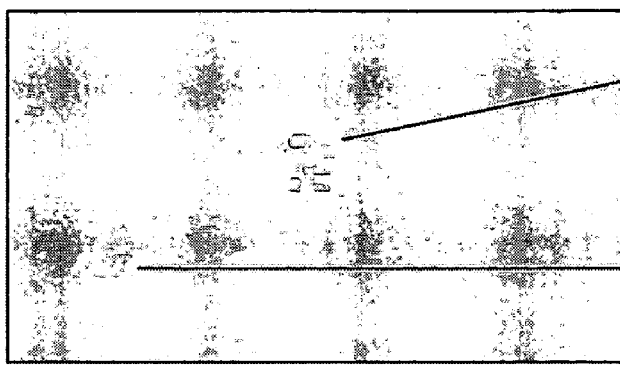
FIGS. 10A-10D are grayscale images of color transmitted light photomicrographs (FIG. 10A and FIG. 10C) and color fluorescence photomicrograph (FIG. 10B and FIG. 10D) of splenic macrophage cells isolated from mice fed fluorescent labeled YGP particles. Aliquots (0.1 ml) of YGP-F and YGMP-F were administered to mice (C57B1/6 wild type and Gaucher mutant mice) by oral gavage or subcutaneous injection showing non-fluorescent macrophages 920 and fluorescent macrophages 922, 924.
Figure 10B:
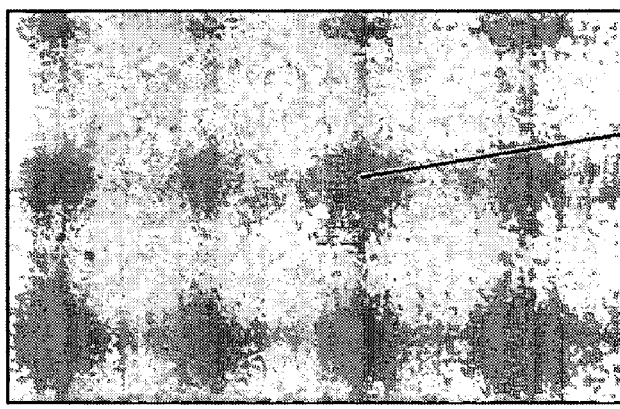
Figure 10C:
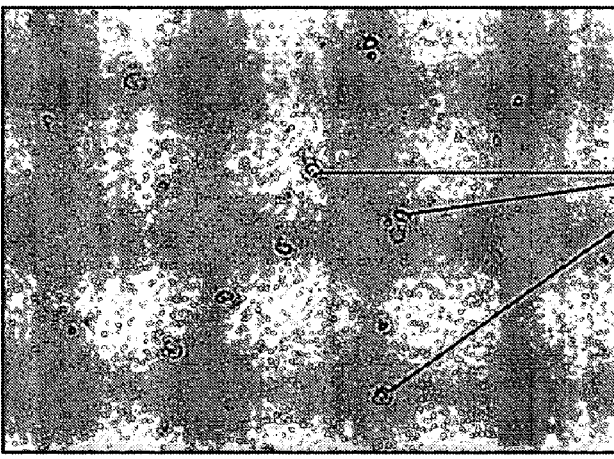
Figure 10D:
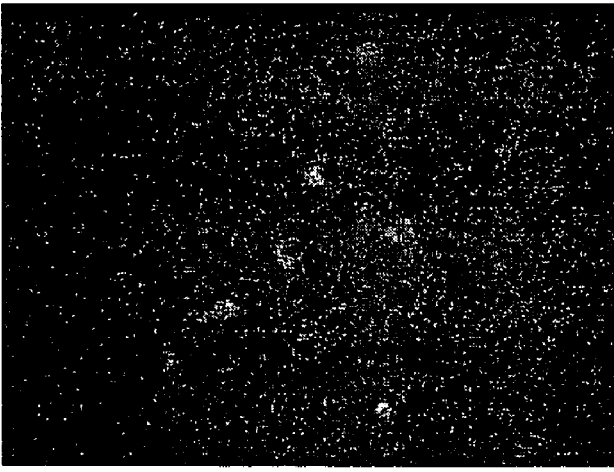

The L444P, R463C and N370S mutations comprise three of the mutations most frequently found in Gaucher patients. The L444P mutation is found in higher frequency in patients having neurologic abnormalities. The use of a replacement vector that contains loxP to generate a longer lived mouse model of Gaucher disease carrying the L444P, R463C and N370S point mutations is illustrated schematically in FIG. 9A and FIG. 9B. A replacement targeting vector using positive/negative selection was constructed containing a neomycin resistance (NeoR) cassette flanked by loxP sequences inserted into the intergenic regions between murine metaxin (MX) and glucocerebrosidase (GC). The L444P mutation was introduced into a genomic clone of murine glucocerebrosidase by PCR mutagenesis. In this way, the normal murine GC sequence in the beginning of exon 9 was changed from TGACTTGGA (SEQ ID NO: 3) to TGACCCGGA (SEQ ID NO: 4), resulting in the amino acid substitution of proline for leucine and introducing a NciI restriction site. This change in sequence was confirmed in the construct by both restriction digest and direct sequence analyses. The final construct contained a 4.0 kb 5' GC homologous arm and a 1.4 kb 3' MX homologous arm. A diphtheria toxin A (DTA) cassette was placed downstream as a negative selectable marker as shown in FIG. 9A.

After linearization, this construct was introduced into RW4 murine embryonic stem (ES) cells by electroporation and the ES cells were subjected to drug selection in culture with G418 as previously described. The correct gene targeting event in G418 resistant individual clones was identified by Southern blot and PCR analysis. Cells from ES clones containing the correctly targeted L444P mutation in one allele of the glucocerebrosidase gene were injected into blastocysts from C57BL/6 mice and then transferred to foster mice. Male offspring from these injections having more than 30% coat color chimerism were test-bred against C57BL/6 females, and progeny were screened by PCR and Southern analyses for transmission of the mutant L444P glucocerebrosidase allele. When the L444P mutation was transmitted, the DNA fragment visualized by an exon 9 probe on Southern analysis and the exon 9 PCR amplified product of 725 bp (forward primer: 5'CTACCATCTTGGCCACTTCAG (SEQ ID NO:5); reverse primer: 5'GCACAGGAGCGAACTCTTTCC, SEQ ID NO: 6) were both cleaved with Nci1. Two lines of mice containing the L444P mutant allele were identified, and the DNA sequence confirmed by direct sequencing of PCR amplified DNA containing the mutation introduced into exon 9. Mice heterozygous for the L444P mutant glucocerebrosidase gene were mated and homozygous mutant progeny were identified by Southern blot and PCR analysis. In addition, heterozygous L444P mice were mated to mice carrying a transgene for CRE DNA recombinase, resulting in the excision of the NeoR marker, leaving only a 34 bp loxP sequence. As expected, the targeted L444P mutation was transmitted in a Mendelian fashion. Assay of glucocerebrosidase activity in mouse tail samples using 4-methylumbellerferyl-glucopyranoside (4MUGP), a fluorescently labeled substrate, demonstrated that in homozygous mutant mice the glucocerebrosidase activity was approximately 35% of the enzyme activity in normal littermates.

FIGS. 10A-10D are grayscale images of color transmitted light photomicrographs (FIG. 10A and FIG. 10C) and color fluorescence photomicrograph (FIG. 10B and FIG. 10D) of splenic macrophage cells isolated from mice fed fluorescent labeled YGP particles. Aliquots (0.1 ml) of YGP-F and YGMP-F were administered to mice (C57B1/6 wild type and Gaucher mutant mice) by oral gavage or subcutaneous injection showing non-fluorescent macrophages 920 and fluorescent macrophages 922, 924.

Brain, liver, bone marrow, small intestine and a section of spleen from each animal were fixed and examined by fluorescent microscopy to determine the extent of fluorescent yeast cell wall particle uptake. An aliquot of spleen was placed on ice and processed to produce single cell suspensions. Splenic cells were plated at ~$10^6$ cells per 12 well plate and incubated for 24 hours to allow for attachment. After washing away unbound cells, the wells were scored for adherent cells (macrophages) with internalized fluorescent particles by fluorescent microscopy.

The treatments were generally well tolerated. Fluorescent microscopic analysis of adherent splenic macrophages demonstrated the presence of fluorescent yeast cell wall particles in all treated animals. These results demonstrate that both YGP-F and YGMP-F are orally bioavailable and systemically distributed by macrophages. Analysis of feces demonstrated presence of fluorescent particles indicating that oral absorption was incomplete. Both the wild type and the Gaucher model mice were competent to take up yeast cell wall particles administered orally.

Oral and subcutaneous administration in vivo of formulations comprising yeast cell wall particles containing a pIRES expression vector was effective in producing expression of green fluorescent protein in murine splenic macrophages. FIGS. 11A-11D are grayscale images of a color fluorescence photomicrographs of splenic macrophage cells isolated from mice treated in vivo showing uptake of yeast cell wall particles containing pIRES expression vectors and expression of green fluorescent protein (GFP). The isolated cells were cultured to appropriate confluency, and adherent cells were formalin fixed, examined using fluorescence microscopy and photographed.

FIG. 11A is a grayscale image of a color fluorescence photomicrograph of splenic macrophage cells isolated from a wild type mouse that received oral gavage in vivo of PBS (control treatment) showing a lack of fluorescent macrophages.

FIG. 11B is a grayscale image of a color fluorescence photomicrograph of splenic macrophage cells isolated from a wild type mouse that received a subcutaneous injection in vivo of 0.1 ml of a YGP-pIRES formulation providing 100 ng of plasmid DNA per dose showing a fluorescent GFP expressing macrophage 930.

FIG. 11C is a grayscale image of a color fluorescence photomicrograph of splenic macrophage cells isolated from a wild type mouse that received an oral dose in vivo of 0.1 ml of a YGP-pIRES formulation providing 100 ng of plasmid DNA per dose showing a fluorescent GFP expressing macrophage 931.

FIG. 11D is a grayscale image of a color fluorescence photomicrograph of splenic macrophage cells isolated from a wild type mouse that received an oral dose in vivo of 0.1 ml of a YGMP-pIRES formulation providing 100 ng of plasmid DNA per dose showing a fluorescent GFP expressing macrophage 932.

Oral and subcutaneous administration in vivo of formulations comprising yeast cell wall particles containing containing a pMFG-GC expression vector prepared as described above was effective in producing expression of human glucocerebrosidase in murine splenic macrophages. FIGS. 12A-12M are images of photomicrographs of immunostained splenic macrophage cells isolated from mice treated in vivo showing uptake of yeast cell wall particles containing pMFG-GC expression vectors and expression of human glucocerebrosidase (hGC). The isolated cells were cultured to appropriate confluency, and adherent cells were formalin fixed. Fixed cells were processed for immunocytochemistry using a primary anti-human GC antibody (rabbit antisera), an appropriate detectable secondary antibody (goat anti-rabbit FITC conjugated antisera), examined using fluorescence microscopy and photographed.

FIG. 12A is an image of a color fluorescence photomicrograph of immunostained splenic macrophage cells isolated from a wild type mouse that received oral gavage in vivo of PBS (control treatment) showing a lack of hGC expressing fluorescent immunostained macrophages.

FIGS. 12B & 12C are images of a color transmitted light photomicrograph (12B) and a color fluorescence photomicrograph (12C) of immunostained splenic macrophage cells isolated from a wild type mouse that received a subcutaneous injection in vivo of 0.1 ml of a YGP-pMFG-GC formulation providing 100 ng of plasmid DNA per dose showing a hGC expressing fluorescent immunostained macrophage 935.

FIG. 12D is an image of a color fluorescence photomicrograph of immunostained splenic macrophage cells isolated from a L444P −/− mutant mouse that received a subcutaneous injection in vivo of 0.1 ml of a YGP-pMFG-GC formulation providing 100 ng of plasmid DNA per dose showing a hGC expressing fluorescent immunostained macrophage 936.

FIG. 12E is an image of a color fluorescence photomicrograph of immunostained splenic macrophage cells isolated from a R463C −/− mutant mouse that received a subcutaneous injection in vivo of 0.1 ml of a YGP-pMFG-GC formulation providing 100 ng of plasmid DNA per dose showing a hGC expressing fluorescent immunostained macrophage 937.

FIGS. 12F & 12G are images of a color transmitted light photomicrograph (12F) and a color fluorescence photomicrograph (12G) of immunostained splenic macrophage cells isolated from a wild type mouse that received an oral dose in vivo of 0.1 ml of a YGP-pMFG-GC formulation providing 100 ng of plasmid DNA per dose showing hGC expressing fluorescent immunostained macrophages, e.g., macrophage 938.

FIGS. 12H & 12I are images of a color transmitted light photomicrograph (12H) and a color fluorescence photomicrograph (12I) of immunostained splenic macrophage cells isolated from a L444P −/− mutant mouse that received 30 days of treatment of an oral dose in vivo of 0.1 ml of a YGP-pMFG-GC formulation providing 100 ng of plasmid DNA per dose showing hGC expressing fluorescent immunostained macrophages, e.g., macrophage 940.

FIG. 12J is an image of a color fluorescence photomicrograph of immunostained splenic macrophage cells isolated from a R463C −/− mutant mouse that received an oral dose in vivo of 0.1 ml of a YGP-pMFG-GC formulation providing 100 ng of plasmid DNA per dose showing hGC expressing fluorescent immunostained macrophages, e.g., macrophage 941.

FIG. 12K is an image of a color fluorescence photomicrograph of immunostained splenic macrophage cells isolated from a wild type mouse that received an oral dose in vivo of 0.1 ml of a YGMP-pMFG-GC formulation providing 100 ng of plasmid DNA per dose showing hGC expressing fluorescent immunostained macrophages, e.g., macrophage 942.

FIG. 12L is an image of a color fluorescence photomicrograph of immunostained splenic macrophage cells isolated from a L444P −/− mutant mouse that received an oral dose in vivo of 0.1 ml of a YGMP-pMFG-GC formulation providing 100 ng of plasmid DNA per dose showing hGC expressing fluorescent immunostained macrophages, e.g., macrophage 943.

FIG. 12M is an image of a color fluorescence photomicrograph of immunostained splenic macrophage cells isolated from a R463C −/− mutant mouse that received an oral dose in vivo of 0.1 ml of a YGMP-pMFG-GC formulation providing 100 ng of plasmid DNA per dose showing hGC expressing fluorescent immunostained macrophages, e.g., macrophage 944.

EXAMPLE 23

Systemic Effects of Oral Administration of YGP and YGMP Particles in Wild-Type and Gaucher's Mice The availability of these long lived point mutation Gaucher mice having biochemical and phenotypic abnormalities similar to Gaucher patients having the same mutation provided a means to test the efficacy of the orally administered gene therapy in correcting the systemic and central nervous system pathology observed in Gaucher disease.

The clinical manifestations of disease in Gaucher mice can be worsened and accelerated by short courses of intraperitoneal (IP) treatment with the glucosidase inhibitor conduritol β-epoxide (CBE, 7-oxabicyclo[4.1.0]heptane-2,3,4,5-tetrol). As previously described in a chimeric mouse model, glucocerebrosidase inhibitors such as CBE and hemolytic agents like phenylhydrazine could be administered to Gaucher mice to further compromise the residual mutant enzyme's ability to degrade lipid, and thereby, leading to increased storage of lipid and more severe and earlier clinical manifestations.

In vivo treatment by oral or subcutaneous administration resulted in the uptake of both YGP & YGMP based formulation in splenic macrophages of both wild type mice and Gaucher model mutant mice. Such treatment resulted in expression of recombinant hGC in isolated splenic macrophages, as measured by detectable increases in hGC immunologically cross-reactive material. The treatment further resulted in an observable amelioration of Gaucher-like symptoms in treated Gaucher model mice, indicating that systemic treatment using the formulations of the present invention had desirable therapeutic results.

The L444P mutant mice were compared to wild type mice and heterozygotes using blood counts, organ size and glucocerebrosidase activity. Complete blood counts were measured for the C57/BL6 (wild-type), transgenic heterozygous, and homozygous mutant animals, and the mean counts were similar, as shown in Table 18, below. The size of the brain, liver, and spleen for wild type (wt), heterozygous (het), and homozygous mutant animals (four of each) were measured. Table 19 provides the mean organ weights.

TABLE 18

| Blood Counts | | |
|---|---|---|
| Blood count | Wild-type Mice | L444P Mice |
| WBC | 6.6 ± 3.4 | 5.8 ± 2.9 |
| Hematocrit | 38.8 ± 4.1 | 39.4 ± 1.1 |
| Platlets | 301,000 ± 35,070 | 308,000 ± 19,500 |

TABLE 19

| Organ Size | | | |
|---|---|---|---|
| Tissue | Wild-type Mice | Heterozygote Mice | L444P Mice |
| brain | 0.45 g | 0.50 g | 0.39 g |
| liver | 1.30 g | 1.30 g | 1.25 g |
| spleen | <0.1 g | <0.1 g | <0.1 g |

All tissues tested in the L444P mutant mice were found to be deficient in glucocerebrosidase activity, as assayed using 4-methylumbelliferyl-B-D-glucopyranoside (4MU-Glu). The glucocerebrosidase activity in the tissues of the untreated L444P Gaucher mice was significantly lower than that of controls: spleen (10%), liver (28%), lung (8%), bone marrow (11%) and brain (65%). Treatment with YGP formulations (2 mice) and YGMP formulations (3 mice) supplemented liver glucocerebrosidase enzyme activity, where the average glucocerebrosidase enzyme activities in untreated L444P Gaucher mice (n=7), L444P Gaucher mice receiving oral glucocerebrosidase gene therapy (n=5) and wild-type mice (n=6) was 12 percent, 29 percent and 100 percent of wild-type mouse glucocerebrosidase specific activity, respectively.

In preliminary studies comparing the effect of YGP and YGMP compositions, the oral administration of YGP-pMFG-GC formulations (a daily oral dose of 0.1 ml of a YGP-pMFG-GC formulation providing 100 ng of plasmid DNA per dose for 14 days and 5 doses per week for 56 days) to a L444P Gaucher mouse produced an increase in glucocerebrosidase activity (normalized to the activity in the corresponding tissues of a wild type mouse) in lung and brain, and a smaller increase in spleen, compared to the activity in tissues of an untreated L444P Gaucher mouse, as shown in Table 20, below.

TABLE 20

| | Spleen | Liver | Lung | Brain |
|---|---|---|---|---|
| Untreated | 10.7 | 27.8 | 7.7 | 66.7 |
| YGP Treated | 16 | 27 | 41 | 85 |
| Wild-Type | 100 | 100 | 100 | 100 |

The oral administration of YGMP-pMFG-GC formulations to a L444P Gaucher mouse produced a somewhat greater increase in glucocerebrosidase activity as shown in Table 21 compared to the increase seen after treatment with the YGP-pMFG-GC formulation. The increase also showed a different tissue-dependent pattern of increase in glucocerebrosidase activity. Table 21, below, shows the results of the average glucocerebrosidase activity determined in spleen, liver, lung and brain tissue of an untreated L444P mouse, and a wild type mouse (C57B1/6) compared to that of a L444P Gaucher mouse that received a daily oral dose of 0.1 ml of a YGP-pMFG-GC formulation providing 100 ng of plasmid DNA per dose for 14 days and 5 doses per week for 56 days, normalized to the activity in the corresponding tissues of the wild type mouse.

TABLE 21

|  | Spleen | Liver | Lung | Brain |
|---|---|---|---|---|
| Untreated | 10.7 | 27.8 | 7.7 | 66.7 |
| YGMP Treated | 86.7 | 92.6 | 61.7 | 97.3 |
| Wild-Type | 100 | 100 | 100 | 100 |

The oral administration of YGMP-pMFG-GC formulations to a R463C mutant mice also produced a tissue-dependent pattern of increase in glucocerebrosidase activity as shown in Table 22, below. Treatment produced little change in the glucocerebrosidase activity in the spleen, a substantial increase in glucocerebrosidase activity in the lung, and an intermediate increase in the liver Table 22 shows the results of the average glucocerebrosidase activity determined in spleen, liver and lung tissue of an untreated R463C mouse, and a wild type mouse (C57B1/6) compared to that of a R463C Gaucher mouse that received a daily oral dose of 0.1 ml of a YGP-pMFG-GC formulation providing 100 ng of plasmid DNA per dose for 14 days and 5 doses per week for 56 days, normalized to the activity in the corresponding tissues of the wild type mouse.

TABLE 22

|  | Spleen | Liver | Lung |
|---|---|---|---|
| Untreated | 30 | 17 | 29 |
| YGMP Treated | 30 | 74 | 100 |
| Wild-Type | 100 | 100 | 100 |

Some mice were made severely symptomatic R463C Gaucher mouse following a course of conduritol β-epoxide (100 mg/kg/day IP for 14 days). After conduritol β-epoxide (100 mg/kg/day IP for 14 days) there was a major difference in phenotype and clinical course between wild type (wt) mice and R463C Gaucher mice. In the Gaucher mice, severe clinical manifestations and pathology remained after seven days of recovery following a 14 treatment with conduritol β-epoxide. Following a course of conduritol β-epoxide (100 mg/kg/day IP for about 2 weeks) L444P Gaucher mice are severely symptomatic. L444P Gaucher mice that had received conduritol β-epoxide (100 mg/kg/day IP for 14 days) followed by at least 70 days of oral administration of 0.1 ml of a YGP-pMFG-GC formulation providing 100 ng of plasmid DNA per dose are less severely ill than those mice that did not receive the YGP-pMFG-GC formulation treatment.

R463C Gaucher mouse become more symptomatic following a course of conduritol β-epoxide (100 mg/kg/day IP for 16 days). R463C Gaucher mouse that had received conduritol β-epoxide (100 mg/kg/day IP for 16 days) followed by at least seventy days of oral administration of 0.1 ml of an YGP-pMFG-GC formulation providing 100 ng of plasmid DNA per dose are clinically more healthy than those that did not receive the YGP-pMFG-GC formulation.

Figure 13:
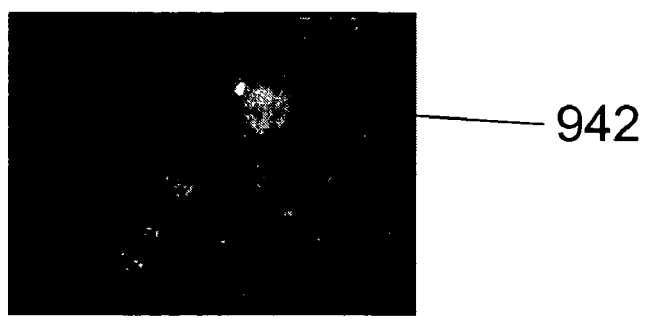
FIG. 13 is a graphic presentation of data from a study showing the increased survival seen in CBE treated R463C Gaucher mice following glucocerebrosidase expression gene therapy in a preferred embodiment of the present invention.
Figure 13:
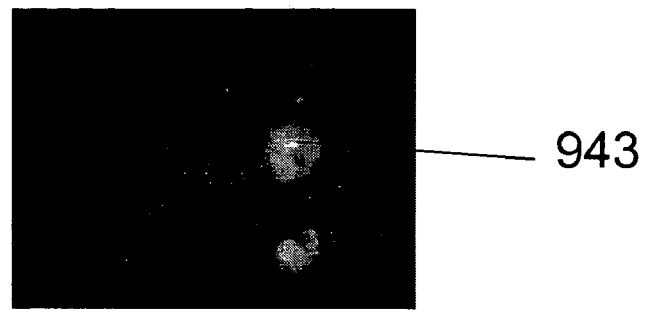
Figure 13:
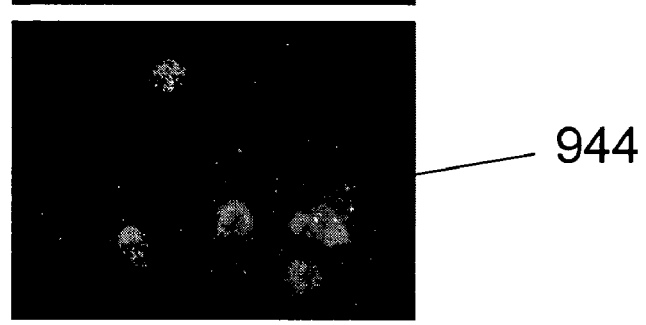
Figure 13:
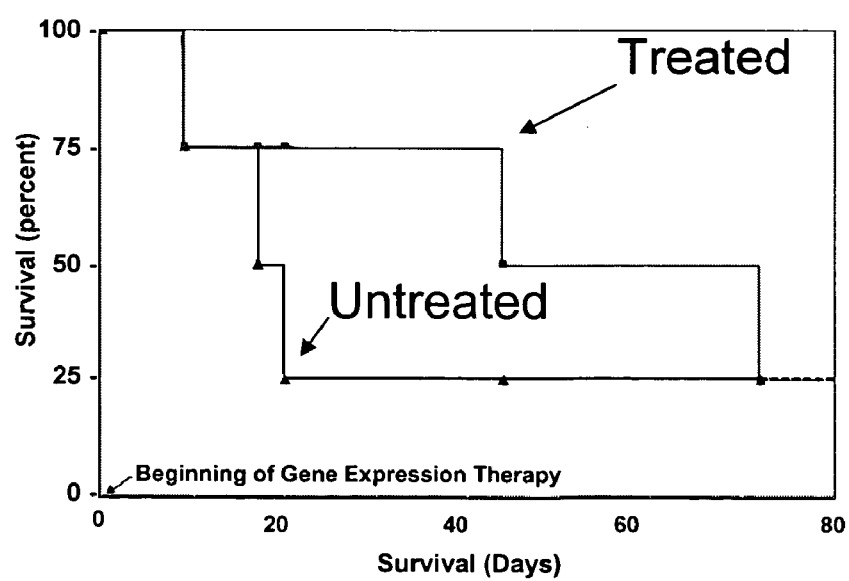

Treatment increased the survival of R463C Gaucher mice. FIG. 13 is a graphic presentation of data from a study showing the increased survival seen in CBE treated R463C Gaucher mice following glucocerebrosidase gene therapy in a preferred embodiment of the present invention.

The claims should not be read as limited to the described order or elements unless stated to that effect. Therefore, all embodiments that come within the scope and spirit of the following claims and equivalents thereto are claimed as the invention.

What is claimed:

1. A therapeutic delivery system comprising: an extracted yeast cell wall defining an internal space and comprising about 6 to about 90 weight percent beta-glucan; a payload trapping molecule and a payload molecule selected from the group consisting of a nucleic acid, a peptide, a protein and a mixture thereof in an amount effective to supplement the function of a deficient lysosomal enzyme, wherein the deficient lysosomal enzyme results in an affected lysosomal function, and wherein the affected lysosomal function is a defective degradation of sphingolipid components related to a lysosomal storage disorder selected from the group consisting of Gaucher disease type 1, Gaucher disease type 2 and Gaucher disease type 3; wherein the payload molecule and the payload trapping molecule are soluble in the same solvent system; wherein the payload trapping molecule is contained within the internal space defined by the extracted yeast cell wall; and wherein the payload trapping molecule is present in an amount sufficient to facilitate retention of the payload molecule within the extracted yeast cell wall.

2. The therapeutic delivery system of claim 1 wherein the payload trapping molecule is selected from the group consisting of chitosan, polyethylenimine, poly-L-lysine, alginate, xanthan, hexadecyltrimethylammoniumbromide and mixtures thereof.

3. The therapeutic delivery system of claim 1 wherein the extracted yeast cell wall further comprises more than 30 weight percent mannan.

4. The therapeutic delivery system of claim 1 wherein extracted yeast cell wall further comprises more than 50 weight percent chitin.

5. The therapeutic delivery system of claim 1 wherein the payload molecule is a nucleic acid comprising a nucleotide sequence which encodes the deficient lysosomal enzyme or a functional equivalent thereof.

6. The therapeutic delivery system of claim 5 wherein the nucleic acid is an expression vector comprising a control element operatively linked to the nucleotide sequence encoding the deficient lysosomal enzyme or functional equivalent thereof.

7. The therapeutic delivery system of claim 1 wherein the payload molecule is a protein which is the deficient lysosomal enzyme or a functional equivalent thereof.

8. The therapeutic delivery system of claim 1 wherein the payload molecule is a nucleic acid comprising a nucleotide sequence which encodes a lysosomal enzyme activator protein or a functional equivalent thereof.

9. The therapeutic delivery system of claim 1 wherein the payload molecule is a peptide which is an enzymatic fragment of the deficient lysosomal enzyme or a functional equivalent thereof.

10. The therapeutic delivery system of claim 1 wherein the payload molecule is a protein which is a lysosomal activator protein or a functional equivalent thereof.

11. The therapeutic delivery system of claim 8 wherein the nucleic acid is an expression vector comprising a control element operatively linked to the nucleotide sequence encoding the lysosomal enzyme activator protein or functional equivalent thereof.

12. The therapeutic delivery system of claim 1, wherein the payload molecule is a peptide which is an enzymatic fragment of a lysosomal enzyme activator protein or a functional equivalent thereof.

13. The therapeutic delivery system of any one of claims 5-7 and 9 wherein the deficient lysosomal enzyme is human glucocerebrosidase.

14. The therapeutic delivery system of any one of claims 8, 11, 10 and 12 wherein the lysosomal enzyme activator protein is selected from the group consisting of saprosin A, saprosin B, saprosin C and saprosin D.

15. A pharmaceutical composition comprising the therapeutic delivery system of any one of claims 1, 5, 7 and 9 and a pharmaceutically acceptable excipient.

16. A method of making a therapeutic delivery system comprising the steps of: providing an extracted yeast cell wall defining an internal space and comprising about 6 to about 90 weight percent beta-glucan;
contacting the extracted yeast cell wall with a payload molecule selected from the group consisting of a nucleic acid, a peptide, a protein and a mixture thereof in an amount effective to supplement the function of a deficient lysosomal enzyme, wherein the deficient lysosomal enzyme results in an affected lysosomal function, and wherein the affected lysosomal function is a defective degradation of sphingolipid components related to a lysosomal storage disorder selected from the group consisting of Gaucher disease type 1, Gaucher disease type 2 and Gaucher disease type 3; contacting the extracted yeast cell wall with a payload trapping molecule wherein the payload molecule and the payload trapping molecule are soluble in the same solvent system; wherein the payload trapping molecule is contained within the internal space defined by the extracted yeast cell wall;
and wherein the payload trapping molecule is present in an amount sufficient to facilitate retention of the payload molecule within the extracted yeast cell wall to form the therapeutic delivery system.

17. The method of claim 16 wherein the payload trapping molecule is selected from the group consisting of chitosan, polyethylenimine, poly-L-lysine, alginate, xanthan, hexadecyltrimethylammoniumbromide and mixtures thereof.

18. The method of claim 16 wherein the extracted yeast cell wall further comprises more than 30 weight percent mannan.

19. The method of claim 16 wherein the extracted yeast cell wall further comprises more than 50 weight percent chitin.

20. The method of claim 16 wherein the payload molecule is a nucleic acid comprising a nucleotide sequence which encodes the deficient lysosomal enzyme or functional equivalent thereof.

21. The method of claim 20 wherein the nucleic acid is an expression vector comprising a control element, operatively linked to the nucleotide sequence encoding the deficient lysosomal enzyme or functional equivalent thereof.

22. The method of claim 16 wherein the payload molecule is a protein which is the deficient lysosomal enzyme or a functional equivalent thereof.

23. The method of claim 16 wherein the payload molecule is a peptide which is an enzymatic fragment of the deficient lysosomal enzyme or functional equivalent thereof.

24. The method of any one of claims 20-22 and 23 wherein the deficient lysosomal enzyme is human glucocerebrosidase.

25. The method of claim 16 wherein the payload molecule is a nucleic acid comprising a nucleotide sequence which encodes a lysosomal enzyme activator protein or a functional equivalent thereof.

26. The method of claim 8 wherein the nucleic acid is an expression vector comprising a control element operatively linked to the nucleotide sequence encoding the lysosomal enzyme activator protein or functional equivalent thereof.

27. The method of claim 16 wherein the payload molecule is a protein which is a lysosomal activator protein or a functional equivalent thereof.

28. The method of claim 16, wherein the payload molecule is a peptide which is an enzymatic fragment of a lysosomal enzyme activator protein or a functional equivalent thereof.

29. The method of any one of claims 25-28 wherein the lysosomal enzyme activator protein is selected from the group consisting of saprosin A, saprosin B, saprosin C and saprosin D.

30. The therapeutic delivery system of claim 1, wherein the therapeutic delivery system is an oral therapeutic delivery system.

31. The method of claim 16, wherein the therapeutic delivery system is an oral therapeutic delivery system.

* * * * *